United States Patent
Takaku et al.

(10) Patent No.: US 11,499,175 B2
(45) Date of Patent: Nov. 15, 2022

(54) MUTANT TYPE 2-DEOXY-SCYLLO-INOSOSE SYNTHASE

(71) Applicants: THE NIIGATA INSTITUTE OF SCIENCE AND TECHNOLOGY, Niigata (JP); MITSUI CHEMICALS, INC., Tokyo (JP)

(72) Inventors: Hiroaki Takaku, Niigata (JP); Harutake Yamazaki, Niigata (JP); Mitsufumi Wada, Chiba (JP); Daisuke Miyazawa, Funabashi (JP)

(73) Assignee: MITSUI CHEMICALS, INC., Tokyo (JP)

( * ) Notice: Subject to any disclaimer, the term of this patent is extended or adjusted under 35 U.S.C. 154(b) by 243 days.

(21) Appl. No.: 16/497,970

(22) PCT Filed: Mar. 15, 2018

(86) PCT No.: PCT/JP2018/010349
§ 371 (c)(1),
(2) Date: Sep. 26, 2019

(87) PCT Pub. No.: WO2018/180568
PCT Pub. Date: Oct. 4, 2018

(65) Prior Publication Data
US 2021/0002687 A1  Jan. 7, 2021

(30) Foreign Application Priority Data

Mar. 27, 2017  (JP) .............................. JP2017-061572

(51) Int. Cl.
| | | |
|---|---|---|
| C12N 9/88 | (2006.01) | |
| C12N 15/60 | (2006.01) | |
| C12N 1/21 | (2006.01) | |
| C12P 7/26 | (2006.01) | |
| C12P 7/02 | (2006.01) | |
| C12P 21/02 | (2006.01) | |
| C12N 15/63 | (2006.01) | |

(52) U.S. Cl.
CPC .............. *C12P 21/02* (2013.01); *C12N 15/63* (2013.01); *C12P 7/26* (2013.01); *C12Y 402/03124* (2015.07)

(58) Field of Classification Search
None
See application file for complete search history.

(56) References Cited

U.S. PATENT DOCUMENTS

| | | | |
|---|---|---|---|
| 2010/0015672 A1 | 1/2010 | Takagi et al. | |
| 2012/0100584 A1* | 4/2012 | Konishi | C12P 7/26 435/148 |

FOREIGN PATENT DOCUMENTS

| | | |
|---|---|---|
| EP | 2 412 807 A1 | 2/2012 |
| JP | 2000236881 A | 9/2000 |
| JP | 2005053899 A | 3/2005 |
| JP | 2013135697 A | 7/2013 |
| JP | 2014064513 A | 4/2014 |
| KR | 10-1019759 B1 | 3/2011 |
| WO | 2006109479 A1 | 10/2006 |
| WO | 2010053052 A1 | 5/2010 |

OTHER PUBLICATIONS

Singh et al., Curr. Protein Pept. Sci. 18:1-11,2017 (Year: 2017).*
Zhang et al., Structure 26:1474-1485, 2018 (Year: 2018).*
GenBank Database Accession No. WP_171682933, 1 page, Jul. 2021 (Year: 2021).*
Hirayama et al., "Role of Glutamate 243 in the Active Site of 2-deoxy-scyllo-inosose Synthase from Bacillus Circulans," Bioorganic Medicinal Chemistry, (Jan. 1, 2007), vol. 15, No. 1, pp. 418-423.
Niigata University of Pharmacy and Applied Life Sciences, Faculty of Applied Life Sciences, Annual Research Report 2014, (Sep. 1, 2015), with partial English translation. (76 pages).
Office Action (Notice of Preliminary Rejection) dated Sep. 1, 2020, by the Korean Intellectual Property Office n corresponding Korean Patent Application No. 10-2019-7029474 with partial English translation of the Office Action. (8 pages).
Hirayama, et al., "Biosynthesis of 2-Deoxystreptamine-containing Antibiotics in Streptoalloteichus hindustanus JCM 3268: Characterization of 2-Deoxy-scyllo-inosose Synthase", The Journal of Antibiotics, vol. 59, (2006), pp. 358-361.
International Search Report (PCT/ISA/210) dated Jun. 12, 2018, by the Japanese Patent Office as the International Searching Authority for International Application No. PCT/JP2018/010349.
Kakinuma, et al., "An expeditious chemo-enzymatic route from glucose to catechol by the use of 2-deoxy-scyllo-inosose synthase", Tetrahedron Letters, vol. 41, (2000), pp. 1935-1938.
Kharel, et al., "A gene cluster for biosynthesis of kanamycin from Streptomyces kanamyceticus: comparison with gentamicin biosynthetic gene cluster", Science Direct, vol. 429, Issue 2, Sep. 15, 2004, pp. 204-214.
Kharel, et al., "Isolation and characterization of the tobramycin biosynthetic gene cluster from Streptomyces tenebrarius", FEMS Microbiology Letters, vol. 230, (2004), pp. 185-190.
Kogure, et al., "Efficient production of 2-deoxy-scyllo-inosose from D-glucose by metabolically engineered recombinant *Escherichia coli*", Journal of Biotechnology, vol. 129, Issue 3, May 1, 2007, pp. 502-509.

(Continued)

*Primary Examiner* — David Steadman
(74) *Attorney, Agent, or Firm* — Buchanan, Ingersoll & Rooney PC

(57) ABSTRACT

A polypeptide includes, in the amino acid sequence of SEQ ID NO: 1 or a similar sequence, at least one specific amino acid substitution on at least one of the 14th, 37th, 209th, 293rd, and 319th amino acid residues from the N-terminal of the amino acid sequence of SEQ ID NO: 1. A polynucleotide, an expression cassette, a vector, and a transformant include a base sequence encoding the amino acid sequence of the polypeptide. A method of producing the polypeptide and a method of producing 2-deoxy-scyllo-inosose are also provided.

13 Claims, 22 Drawing Sheets
Specification includes a Sequence Listing.

(56) References Cited

OTHER PUBLICATIONS

Kudo et al., Biosynthesis of 2-Deoxystreptamine by Three Crucial Enzymes in Streptomyces fradiae NBRC 12773, The Journal of Antibiotics, vol. 58, (2005), pp. 766-774.
Kudo, et al., "Molecular Cloning of the Gene for the Key Carbocycle-forming Enzyme in the Biosynthesis of 2-Deoxystreptamine-containing Aminocyclitol Antibiotics and its Comparison with Dehydroquinate Synthase", Journal of Antibiotics, vol. 52, No. 6, Jun. 1999, pp. 559-571.
Subba, et al., "The Ribostamycin Biosynthetic Gene Cluster in Streptomyces ribosidificus Comparision with Butirosin Biosynthesis", Molecules and Cells, vol. 20, No. 1, (2005), pp. 90-96.
Takaku, et al., "Research Projects and annual reports", Sep. 1, 2015, 8 pages.
Tamegai, et al., "Roles of a 20 kDa Protein Associated with a Carbocycle-Forming Enzyme Involved in Aminoglycoside Biosynthesis in Primary and Secondary Metabolism", Biosci. Biotechnol. Biochem, vol. 74, (2010), pp. 1215-1219.
Unwin, et al., "Gene Cluster in Micromonospora echinospora ATCC15835 for the Biosynthesis of the Gentamicin C Complex", The Journal of Antibiotics, vol. 57, No. 7, Jul. 2004, pp. 436-445.
Wakisaka, et al., "Acquiring highly active mutants of aromatic compound precursor synthesis enzymes by evolutionary engineering techniques and improving efficiency of precursor synthesis", JSBBA Annual Meeting Report, Mar. 5, 2011, vol. 2011, 7 pages.
Written Opinion (PCT/ISA/237) dated Jun. 12, 2018, by the Japanese Patent Office as the International Searching Authority for International Application No. PCT/JP2018/010349.
Konishi, K. et al., "*Paenibacillus* sp. variant DOI synthase-2 enzyme, SEQ ID:4." XP002800695, retrieved from EBI accession No. GSP:AYJ79980, Nov. 25, 2010, (1 page).
Konishi, K. et al., "*Paenibacillus* sp. variant DOI synthase-3 enzyme, SEQ ID:6." XP002800694, retrieved from EBI accession No. GSP:AYJ79984; Database Geneseq [Online], Nov. 25, 2010, (1 page).
Extended European Search Report dated Nov. 3, 2020, issued by the European Patent Office in corresponding European Application No. 18777395.7-1118, (8 pages).

\* cited by examiner

Δpgi Δzwf Δpgm strain pGAP-btrC/pGAD-btrC

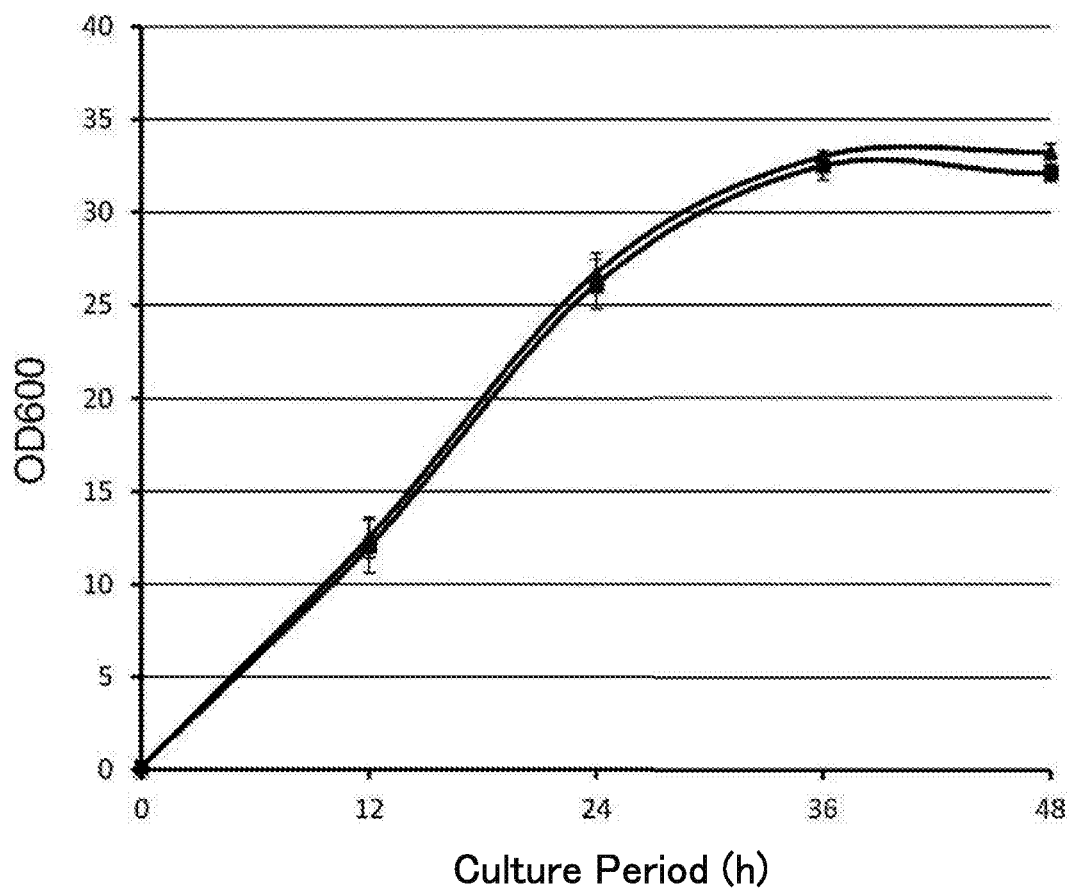

MUTANT TYPE 2-DEOXY-SCYLLO-INOSOSE SYNTHASE

SEQUENCE LISTING

Incorporated by reference herein in its entirety is a computer-readable sequence listing submitted on Sep. 26, 2019, via EFS-Web and identified as follows: One (7,742 byte ASCII (Text)) file named "MT-F03216-01_SequenceListing.txt" created on Jun. 17, 2019.

TECHNICAL FIELD

The present disclosure relates to, for example, a modified 2-deoxy-scyllo-inosose (hereinafter referred to as "DOI") synthase, a gene that encodes the modified DOI synthase, an expression cassette that includes the gene, a vector that includes the expression cassette, a transformant that includes the vector, a method of producing a modified DOI synthase using the transformant, and a method of producing DOI.

BACKGROUND ART

Many of familiar products in our daily life, such as plastics and detergents, are manufactured using fossil resources as raw materials. Six-membered carbocyclic compounds for use as raw materials for these chemical products are produced from crude oil in the petrochemical industry. However, when conventional petrochemical processes in which raw materials for chemical products are produced from crude oil are used, global scale problems may arise such as exhaustion of a limited crude oil resource and an accompanying price hike, and global warming due to the emission of a large amount of carbon dioxide.

DOI, which is a chiral compound having a six-membered carbocyclic skeleton, is a very important intermediate material for the synthesis of various useful chemicals such as pharmaceuticals, agricultural chemicals, oxidation inhibitors and perfumes. DOI can be synthetically converted to a dihydric phenol such as catechol or hydroquinone or hydroxyhydroquinone. For example, Kakinuma et al., Tetrahedron Letters, vol. 41(2000), p. 1935 discloses synthetic conversion of DOI to catechol. Catechol is used as a raw material for medicines for the nerve system, a raw material for flavors, or as an antioxidant for hair care products. Hydroquinone is used as a material for, for example, hemostatic agents and analgesics, or used in cosmetics such as skin whitening agents. There is a high worldwide demand for catechol and hydroquinone. DOI can also be converted to carbaglucose, which is a pseudosugar, and is a versatile intermediate raw material. For example, Japanese Patent Application Laid-open (JP-A) No. 2005-053899 discloses synthesis of carbaglucose using DOI as a raw material.

2-deoxystreptamine-containing aminoglycoside-based antibiotics are used as a large number of important chemotherapeutic drugs in clinical medicine. It has been found that one of the enzymes involved in the biosynthesis process of 2-deoxystreptamine-containing aminoglycoside-based antibiotics is an enzyme that converts a carbohydrate as a starting material into a carbocycle. This enzyme has been purified from a microorganism belonging to Bacillus circulans, which is a butirosin-producing bacterium, and catalyzes multi-step reactions using glucose 6-phosphate as a substrate and nicotinamide adenine dinucleotide ($NAD^+$) as a coenzyme, thereby finally resulting in biosynthesis of DOI. Kudo et al., J. Antibiot., vol. 52(1999), p. 559 and Japanese Patent Application Laid-Open (JP-A) No. 2000-236881 describe that a DOI synthase gene (btrC, which encodes an enzyme that catalyzes a conversion reaction from glucose 6-phosphate into DOI) from microorganisms belonging to Bacillus circulans was cloned, and that a large amount of a recombinant DOI synthase was obtained by expressing the gene in Escherichia coli, followed by purification. Furthermore, Japanese Patent Application Laid-Open (JP-A) No. 2014-064513 discloses that DOI can be synthesized via a two-step enzymatic reaction in which (i) hexokinase or polyphosphate glucokinase and (ii) DOI synthase are allowed to act on glucose, or via a one-step enzymatic reaction in which DOI synthase is allowed to act on glucose 6-phosphate. Furthermore, Hirayama et al., J. Antibiot., vol. 58(2005), p. 766 discloses a DOI synthase from Streptomyces fradiae, Subba et al., Mol. Cells, vol. 20(2005), p. 90 discloses a DOI synthase from Streptomyces ribosidificus, Kharel et al., Arch. Biochem. Biophys., vol. 429(2004), p. 204 discloses a DOI synthase from Streptomyces kanamyceticus, J. Antibiot., vol. 57(2004), p. 436 discloses a DOI synthase from Micromonospora echinospora, Kharel et al., FEMS Microbiol. Lett., vol. 230 (2004), p. 185 discloses a DOI synthase from Streptomyces tenebrarius, and Hirayama et al., J. Antibiot., vol. 59(2006), p. 358 discloses a DOI synthase from Streptoalloteichus hindustanus.

In addition, Japanese Patent Application Laid-Open (JP-A) No. 2013-135697 discloses a heat-resistant DOI synthase having a specific amino acid sequence, and Tamegai et al., Biosci. Biotechnol. Biochem. vol. 74(2010), p. 1215 describes a role of BtrC2 protein that accompanies DOI synthase of Bacillus circulans. WO 2006/109479 and Kogure et al., J. Biotechnol. vol. 129(2007), p. 502 disclose an expression cassette having a gene of DOI synthase, and an attempt has been made to increase the production amount by an engineered alteration of intracellular carbohydrate metabolism. WO 2010/053052 discloses a DOI-producing Escherichia coli which has at least a gene encoding sucrose hydrolase (CscA) among sucrose non-PTS genes, and in which a 2-deoxy-scyllo-inosose (DOI) production system has been added or enhanced, and which preferably further has a sugar uptake ability enhancing system.

SUMMARY OF THE INVENTION

Technical Problem

The techniques described in the above-mentioned patent documents and non-patent documents do not relate to an attempt to enhance a DOI synthase activity by modifying the amino acid sequence of DOI synthase. Enhancement of an enzymatic activity by enzyme modification is also an effective means for construction of a system capable of producing DOI with high efficiency using a DOI synthase. An improvement of the efficiency of production of DOI would enable more cost-effective DOI production in a large amount in a short time. A method for enhancing the enzymatic activity includes modifying an amino acid at an active center that binds to a substrate of the enzyme and selecting a high activity enzyme. There is also an evolutional engineering method including rapid and artificial in vitro introduction of mutations in a gene encoding an enzyme of interest and selection of a gene encoding an enzyme modified to have the desired activity from among a large number of mutant genes. The latter method is applied to alterations of, for example, enzymes for detergents and enzymes for production of biodegradable plastics. However, application of such techniques to alteration of DOI synthase is not known.

The present inventors focused on the activity of DOI synthase, and conceived of an idea that production of a large amount of DOI in a short time may be enabled by efficiently converting glucose 6-phosphate into DOI using a DOI synthase having an improved DOI synthesis activity. In view of the above circumstances, an object of an embodiment according to the present disclosure is provision of a modified DOI synthase having a higher DOI synthesis activity than a wild-type DOI synthase consisting of an amino acid sequence of SEQ ID NO: 1, a gene that encodes the modified DOI synthase, an expression cassette that includes the gene, a vector that includes the expression cassette, a transformant that includes the vector, a method of producing a modified DOI synthase using the transformant, and a method of producing DOI.

Technical Solution

As a result of intensive study for the purpose of achieving the above object, the present inventors have succeeded in altering a DOI synthase into an enzyme having a higher DOI synthesis activity by using an evolutionary engineering method. Moreover, the present inventors have also succeeded in producing DOI using a transformant that includes a gene encoding a modified enzyme obtained by the above method, with a higher efficiency than that achieved by conventional means.

According to the present disclosure, the following aspects (1) to (9) are provided.

(1) A polypeptide comprising at least one amino acid mutation selected from the group consisting of the following (a) to (e) in an amino acid sequence of the following (A1) or (A2):

(A1) an amino acid sequence of SEQ ID NO: 1;

(A2) an amino acid sequence of a polypeptide having an enzymatic activity that produces 2-deoxy-scyllo-inosose from glucose 6-phosphate, the amino acid sequence (A2) having a sequence identity of 80% or higher with the amino acid sequence of SEQ ID NO: 1, (a) an amino acid mutation in which an amino acid residue corresponding, in terms of alignment, to an asparagine residue that is a 14th amino acid residue from the N-terminal in the amino acid sequence of SEQ ID NO: 1 is substituted with threonine;

(b) an amino acid mutation in which an amino acid residue corresponding, in terms of alignment, to a tyrosine residue that is a 37th amino acid residue from the N-terminal in the amino acid sequence of SEQ ID NO: 1 is substituted with phenylalanine;

(c) an amino acid mutation in which an amino acid residue corresponding, in terms of alignment, to an alanine residue that is a 290th amino acid residue from the N-terminal in the amino acid sequence of SEQ ID NO: 1 is substituted with threonine;

(d) an amino acid mutation in which an amino acid residue corresponding, in terms of alignment, to a tryptophan residue that is a 293rd amino acid residue from the N-terminal in the amino acid sequence of SEQ ID NO: 1 is substituted with arginine;

(e) an amino acid mutation in which an amino acid residue corresponding, in terms of alignment, to a histidine residue that is a 319th amino acid residue from the N-terminal in the amino acid sequence of SEQ ID NO: 1 is substituted with arginine.

(2) The polypeptide according to aspect (1), wherein the polypeptide comprises at least one of the amino acid mutation (d) or (e) in the amino acid sequence (A1) or (A2).

(3) The polypeptide according to aspect (1), wherein the polypeptide comprises the amino acid mutation (d), and at least one amino acid mutation selected from the group consisting of the amino acid mutations (a), (b), (c) and (e), in the amino acid sequence (A1) or (A2).

(4) A polynucleotide comprising a base sequence encoding an amino acid sequence of the polypeptide according to any one of aspects (1) to (3).

(5) An expression cassette comprising the polynucleotide according to aspect (4), a promoter sequence linked upstream of the polynucleotide, and a terminator sequence linked downstream of the polynucleotide.

(6) A vector, comprising the expression cassette according to aspect (5).

(7) A transformant that is transformed with the vector according to aspect (6).

(8) A method of producing a polypeptide having an enzymatic activity that produces 2-deoxy-scyllo-inosose from glucose 6-phosphate, the method comprising culturing the transformant according to aspect (7).

(9) A method of producing 2-deoxy-scyllo-inosose, the method comprising contacting the polypeptide according to any one of aspects (1) to (3), the transformant according to aspect (7), a culture product of the transformant, or a processed product of the transformant or the culture product, with glucose or glucose 6-phosphate, thereby converting the glucose or glucose 6-phosphate into 2-deoxy-scyllo-inosose.

Advantageous Effect of Invention

According to the present disclosure, a modified DOI synthase having a higher DOI synthesis activity than a wild-type DOI synthase consisting of an amino acid sequence of SEQ ID NO: 1, a gene that encodes the modified DOI synthase, an expression cassette that includes the gene, a vector that includes the expression cassette, a transformant that includes the vector, a method of producing a modified DOI synthase using the transformant, and a method of producing DOI can be provided.

BRIEF DESCRIPTION OF THE DRAWINGS

FIG. 14A shows a time course of turbidity of the culture medium during cultivation (2×YT+3% glucose+4% mannitol, 30 mL, 30° C.) of an *Escherichia coli* GI724ΔpgiΔzwfΔpgm strain that harbors pGAPP-btrC (■) and an *Escherichia coli* GI724ΔpgiΔzwfΔpgm strain that harbors pGAPP-btrC (H319R) (▲).

MODES FOR CARRYING OUT INVENTION

According to the present disclosure, a modified DOI synthase having a higher DOI synthesis activity than a wild type DOI synthase consisting of an amino acid sequence of SEQ ID NO: 1, a gene that encodes the modified DOI synthase, an expression cassette that includes the gene, a vector that includes the expression cassette, a transformant that includes the vector, a method of producing a modified DOI synthase using the transformant, and a method of producing DOI can be provided.

The modified DOI synthase according to the present disclosure enables improvement of the DOI production speed due to a high DOI synthesis activity of the modified DOI synthase, and enables efficient conversion of glucose 6-phosphate into DOI in a short time. According to the method of producing a modified DOI synthase according to the present disclosure, a modified synthase having a high DOI synthesis activity can be produced by expressing a modified DOI synthase gene in a host cell. Moreover, the method of producing DOI according to the present disclosure enables production of DOI from glucose with high efficiency, using the modified DOI synthase gene.

Figure 1:
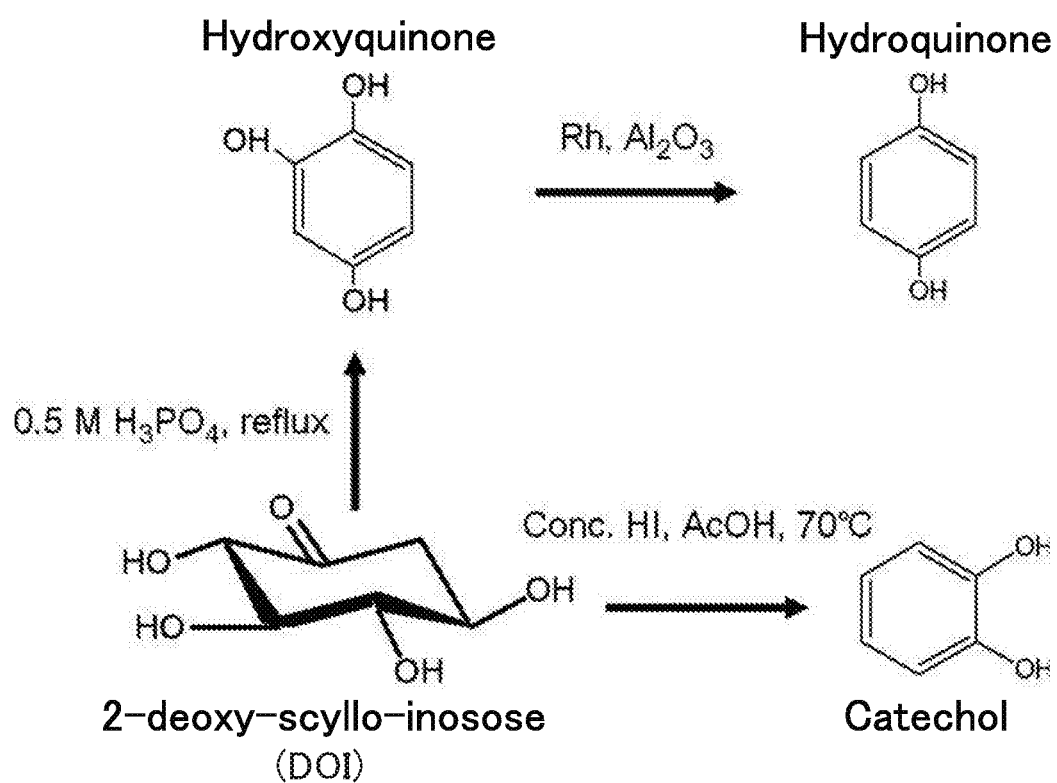
FIG. 1 illustrates aromatic compounds that can be synthetically converted from DOI.

As described above, DOI can be synthetically converted to a dihydric phenol such as catechol or hydroquinone, or to hydroxyhydroquinone (see FIG. 1). According to one embodiment of the present disclosure, DOI, which is expected to be widely used as a raw material for production of medicines and industrial products, can be produced in a large amount in a simple manner with high efficiency. From the DOI produced, it is also possible to produce, for example, 1,2,4-trihydroxybenzene, which is expected to be widely used as a raw material for production of medicines and industrial products.

<Modified DOI Synthase>

The modified DOI synthase according to the present disclosure is a polypeptide comprising at least one amino acid mutation selected from the group consisting of the following (a) to (e) in the amino acid sequence of the following (A1) or (A2):

(A1) an amino acid sequence of SEQ ID NO: 1

(A2) an amino acid sequence of a polypeptide having an enzymatic activity that produces 2-deoxy-scyllo-inosose from glucose 6-phosphate, the amino acid sequence (A2) having a sequence identity of 80% or higher with the amino acid sequence of SEQ ID NO: 1, (a) an amino acid mutation in which an amino acid residue corresponding, in terms of alignment, to an asparagine residue that is a 14th amino acid residue from the N-terminal in the amino acid sequence of SEQ ID NO: 1 is substituted with threonine;

(b) an amino acid mutation in which an amino acid residue corresponding, in terms of alignment, to a tyrosine residue that is a 37th amino acid residue from the N-terminal in the amino acid sequence of SEQ ID NO: 1 is substituted with phenylalanine;

(c) an amino acid mutation in which an amino acid residue corresponding, in terms of alignment, to an alanine residue that is a 290th amino acid residue from the N-terminal in the amino acid sequence of SEQ ID NO: 1 is substituted with threonine;

(d) an amino acid mutation in which an amino acid residue corresponding, in terms of alignment, to a tryptophan residue that is a 293rd amino acid residue from the N-terminal in the amino acid sequence of SEQ ID NO: 1 is substituted with arginine;

(e) an amino acid mutation in which an amino acid residue corresponding, in terms of alignment, to a histidine residue that is a 319th amino acid residue from the N-terminal in the amino acid sequence of SEQ ID NO: 1 is substituted with arginine.

The modified DOI synthase having an amino acid residue substitution or amino acid residue substitutions at the specific amino acid residue or residues has an improved DOI synthesis activity due to the amino acid residue substitution or amino acid residue substitutions. Although the modified DOI synthase according to the present disclosure can be expressed as a polypeptide having an amino acid sequence obtained by introducing at least one amino acid mutation selected from the group consisting of the following (a) to (e) into the amino acid sequence of (A1) or (A2), the passage "obtained by introducing at least one amino acid mutation selected from the group consisting of the following (a) to (e) into the amino acid sequence of (A1) or (A2)" in this expression is used only for the purpose of specifying the final amino acid sequence, and limits neither the starting-point amino acid sequence nor the actual process of altering the sequence.

The amino acid sequence of SEQ ID NO: 1 is the amino acid sequence of DOI synthase from *Bacillus circulans*, and is encoded by btrC gene. The modified DOI synthase has an amino acid sequence different from the amino acid sequence of SEQ ID NO: 1, and is also referred to as a mutant DOI synthase in the present disclosure. The amino acid sequence of SEQ ID NO: 1 is shown in Table 1 below.

TABLE 1

| | | | | | | | | | | | | | | |
|---|---|---|---|---|---|---|---|---|---|---|---|---|---|---|
| Met 1 | Thr | Thr | Lys | Gln 5 | Ile | Cys | Phe | Ala | Asp 10 | Arg | Cys | Phe | Asn | Phe 15 | Ala |
| Phe | Gly | Glu | His 20 | Val | Leu | Glu | Ser | Val 25 | Glu | Ser | Tyr | Ile | Pro 30 | Arg | Asp |
| Glu | Phe | Asp 35 | Gln | Tyr | Ile | Met | Ile 40 | Ser | Asp | Ser | Gly | Val 45 | Pro | Asp | Ser |
| Ile | Val | His 50 | Tyr | Ala | Ala | Glu | Tyr 55 | Phe | Gly | Lys | Leu | Ala 60 | Pro | Val | His |
| Ile | Leu | Arg 65 | Phe | Gln | Gly 70 | Gly | Glu | Glu | Tyr | Lys 75 | Thr | Leu | Ser | Thr | Val 80 |
| Thr | Asn | Leu | Gln | Glu 85 | Arg | Ala | Ile | Ala | Leu 90 | Gly | Ala | Asn | Arg | Arg 95 | Thr |
| Ala | Ile | Val | Ala 100 | Val | Gly | Gly | Gly | Leu 105 | Thr | Gly | Asn | Val | Ala 110 | Gly | Val |
| Ala | Ala | Gly 115 | Met | Met | Phe | Arg | Gly 120 | Ile | Ala | Leu | Ile | His 125 | Val | Pro | Thr |
| Thr | Phe 130 | Leu | Ala | Ala | Ser | Asp 135 | Ser | Val | Leu | Ser | Ile 140 | Lys | Gln | Ala | Val |
| Asn | Leu 145 | Thr | Ser | Gly | Lys | Asn 150 | Leu | Val | Gly | Phe | Tyr 155 | Tyr | Pro | Pro | Arg 160 |
| Phe | Val | Phe | Ala | Asp 165 | Thr | Arg | Ile | Leu | Ser 170 | Glu | Ser | Pro | Pro | Arg 175 | Gln |

TABLE 1-continued

```
Val Lys Ala Gly Met Cys Glu Leu Val Lys Asn Met Leu Ile Leu Glu
            180                 185                 190

Asn Asp Asn Lys Glu Phe Thr Glu Asp Asp Leu Asn Ser Ala Asn Val
        195                 200                 205

Tyr Ser Pro Lys Gln Leu Glu Thr Phe Ile Asn Phe Cys Ile Ser Ala
    210                 215                 220

Lys Met Ser Val Leu Ser Glu Asp Ile Tyr Glu Lys Lys Lys Gly Leu
225                 230                 235                 240

Ile Phe Glu Tyr Gly His Thr Ile Gly His Ala Ile Glu Leu Ala Glu
                245                 250                 255

Gln Gly Gly Ile Thr His Gly Glu Ala Ile Ala Val Gly Met Ile Tyr
                260                 265                 270

Ala Ala Lys Ile Ala Asn Arg Met Asn Leu Met Pro Glu His Asp Val
            275                 280                 285

Ser Ala His Tyr Trp Leu Leu Asn Lys Ile Gly Ala Leu Gln Asp Ile
        290                 295                 300

Pro Leu Lys Ser Asp Pro Asp Ser Ile Phe His Tyr Leu Ile His Asp
305                 310                 315                 320

Asn Lys Arg Gly Tyr Ile Lys Leu Asp Glu Asp Asn Leu Gly Met Ile
                325                 330                 335

Leu Leu Ser Gly Val Gly Lys Pro Ala Met Tyr Asn Gln Thr Leu Leu
                340                 345                 350

Thr Pro Val Arg Lys Thr Leu Ile Lys Glu Val Ile Arg Glu Gly Leu
            355                 360                 365
```

The enzymatic activity that produces 2-deoxy-scyllo-inosose from glucose 6-phosphate can be measured by:

allowing a 50 mM phosphate buffer (pH 7.7) solution that contains 5 mM glucose 6-phosphate, 5 mM β-NAD$^+$, 0.2 mM CoCl$_2$.6H$_2$O, and 10 μg of DOI synthase to be assayed to react at 46° C. for 5 minutes, subjecting, after the reaction, the reaction solution to phenol-chloroform treatment, thereby removing proteins, quantifying DOI by HPLC, using 10 μL of the aqueous layer fraction after centrifugation as a sample; and calculating the activity.

In addition, the amount of DOI synthesized by 1 mg of DOI synthase per minute is defined as "specific activity".

The condition of HPLC is as follows:

Column: PHENOMENEX KINETEX XB-C18 100 Å (manufactured by Phenomenex)

Eluent: H$_2$O/methanol (80/20)

Flow rate: 0.7 mL/min

Column temperature: 40° C.

Detection: UV 262 nm

Injection volume: 2 μL

The sequence identity of amino acid sequences can be evaluated using, for example, BLAST (registered trademark, National Library of Medicine) program with default parameters.

In the amino acid sequence (A1) or (A2), the amino acid residue corresponding, in terms of alignment, to an amino acid residue at a specific position in the amino acid sequence of SEQ ID NO: 1 is an amino acid residue in the amino acid sequence (A1) or (A2) that is found to correspond to the amino acid residue at a specific position in SEQ ID NO: 1 when the amino acid sequence of SEQ ID NO: 1 and the amino acid sequence (A1) or (A2) are aligned using, for example, the BLAST (registered trademark, National Library of Medicine) program (default parameters).

The sequence identity of the amino acid sequence (A2) with respect to the amino acid sequence of SEQ ID NO: 1 may be 85% or higher, 90% or higher, or 95% or higher.

The amino acid sequence (A2) may be an amino acid sequence that includes a sequence modification in the amino acid sequence of SEQ ID NO: 1, the sequence modification being within a range in which DOI synthase activity is not lost. That is, the amino acid sequence (A2) may be an amino acid sequence obtained by introducing a sequence modification into the amino acid sequence of SEQ ID NO: 1, the sequence modification being within a range in which DOI synthase activity is not lost. Examples of the sequence modification include insertion, deletion, or substitution of an amino acid residue, and addition of an additional amino acid residue to the N-terminal of the amino acid sequence or the C-terminal of the amino acid sequence or both. When at least one of insertion, deletion or substitution of an amino acid residue is present, each of the insertion, deletion and substitution, if any, occurs, for example, at from 1 to 30 amino acid residues, or from 1 to 20 amino acid residues, or from 1 to 10 amino acid residues, or from 1 to 5 amino acid residues, and the total number of insertions, deletions and substitutions of amino acid residues is, for example, from 1 to 50 amino acid residues, or from 1 to 30 amino acid residues, or from 1 to 10 amino acid residues, or from 1 to 5 amino acid residues. When amino acid residues are added to the terminal or terminals, the number of amino acid residues added is, for example, from 1 to 50 amino acid residues per terminal, or from 1 to 30 amino acid residues per terminal, or from 1 to 10 amino acid residues per terminal, or from 1 to 5 amino acid residues per terminal. The additional amino acid residues may form a signal sequence for, for example, extracellular secretion. Examples of the signal sequence include *Escherichia coli* OmpA signal sequence.

The amino acid mutations (a) to (e) each increase DOI synthase activity. The modified DOI synthase according to the present disclosure may comprise one of the amino acid mutations (a) to (e), or comprise two or more of the amino acid mutations (a) to (e). For example, the modified DOI synthase may have two, three, four, or five of the amino acid mutations of (a) to (e). In one embodiment, the modified DOI synthase comprises at least one of the amino acid mutations (d) and (e), and may further comprise at least one of the amino acid mutations (a) to (c). In another embodiment, the modified DOI synthase comprises an amino acid mutation of (d), and further comprises at least one of the amino acid mutations (a), (b), (c) and (e). In still another embodiment, the modified DOI synthase comprises the amino acid mutation (d) and further comprises at least one of the amino acid mutations (a), (b) and (e). In this case, the modified DOI synthase may further comprise the amino acid mutation (c). In yet another embodiment, the modified DOI synthase comprises the amino acid mutation of (d) and further comprises at least one of the amino acid mutations (a) and (e). In this case, the modified DOI synthase may further comprise at least one of the amino acid mutations (b) and (c). In still another embodiment, the modified DOI synthase comprises the amino acid mutation (d) and the amino acid mutation (e). In this case, the modified DOI synthase may further comprise at least one of the amino acid mutations (a) to (c).

The polypeptide having a sequence identity of 80% or higher with the amino acid sequence of SEQ ID NO: 1 and having an enzymatic activity that produces 2-deoxy-scyllo-inosose from glucose 6-phosphate has an enzyme-function-related structure that is highly similar to that in the amino acids in SEQ ID NO: 1. Therefore, each of the amino acid mutations (a) to (e) also exerts an effect in terms of elevating the DOI synthase activity also when applied to the polypeptide having a sequence identity of 80% or higher with the amino acid sequence of SEQ ID NO: 1 and having an enzymatic activity that produces 2-deoxy-scyllo-inosose from glucose 6-phosphate.

As described above, the modified DOI synthase having an improved DOI synthase activity can be obtained by incorporating one or more of the amino acid mutations (a) to (e). The modified DOI synthase preferably has a higher DOI synthesis activity than that of a DOI synthase having the amino acid sequence of SEQ ID NO: 1 (also referred to as "wild type DOI synthase" in the present disclosure). The modified DOI synthase has a DOI synthesis activity that is preferably at least 1.1 times higher than that of the DOI synthase having the amino acid sequence of SEQ ID NO: 1, more preferably at least 1.2 times higher than that of the DOI synthase having the amino acid sequence of SEQ ID NO: 1, more preferably at least 1.3 times higher than that of the DOI synthase having the amino acid sequence of SEQ ID NO: 1, more preferably at least 1.4 times higher than that of the DOI synthase having the amino acid sequence of SEQ ID NO: 1, more preferably at least 1.5 times higher than that of the DOI synthase having the amino acid sequence of SEQ ID NO: 1, more preferably at least 1.6 times higher than that of the DOI synthase having the amino acid sequence of SEQ ID NO: 1, more preferably at least 1.7 times higher than that of the DOI synthase having the amino acid sequence of SEQ ID NO: 1, and even more preferably at least 1.8 times higher than that of the DOI synthase having the amino acid sequence of SEQ ID NO: 1.

The amino acid mutations (a) to (e) have been obtained by modification of DOI synthase via evolutionary engineering.

<Modification of DOI Synthase Via Evolutionary Engineering>

Modification via evolutionary engineering refers to a technique of modifying a protein molecule of interest, the technique including artificially inducing a mutation in vitro in a gene encoding the protein of interest, and selecting a protein that has been modified to have the desired property.

The introduction of random mutations into the enzyme gene of interest can be carried out by subjecting a microorganism harboring the enzyme gene of interest to treatment with an alkylating reagent (for example, N-methyl-N'-nitro-N-nitrosoguanidine), treatment with oxidative deamination reagent (for example, nitrous acid) for nucleic acid bases, irradiation with a radiation (for example, ultraviolet light or X-ray), or random mutagenesis using PCR.

The introduction of random mutations using PCR can be performed by error-prone PCR, which includes accumulating errors in sequences of amplified DNA fragments by performing PCR reactions using a DNA fragment containing the enzyme gene of interest as a template, under conditions in which the accuracy of DNA replication by DNA polymerase is reduced in the amplification process of the gene. In error-prone PCR, the accuracy of DNA polymerase is reduced and mutations can be introduced by, for example, adding manganese ions to the reaction solution, or making the concentrations of the four deoxyribonucleic acids (dNTPs) unbalanced.

For example, in the case of introducing a mutation into a DOI synthase gene (btrC) from *Bacillus circulans* by error prone PCR, PCR may be performed using a plasmid carrying the gene (for example, pLEX-btrC described in WO 2006/109479) or a DNA fragment carrying the gene as a template, and primers for amplifying the gene, under conditions in which the accuracy of the DNA polymerase is reduced. The conditions in which the accuracy of the DNA polymerase is reduced are, for example, the conditions described in Example 1 described later.

Moreover, the group of modified enzyme genes obtained by introduction of random mutations may be screened using, as an indicator, the presence or absence of improved function in terms of the property of interest. For example, the DOI synthesis activity of a group of modified enzymes expressed by the group of modified enzyme genes may be measured, and modified enzymes having an improved DOI synthesis activity than that before mutation may be selected. In this way, modified enzymes having an improved activity in terms of the property of interest can be obtained. The obtained genes encoding the modified enzymes may further be subjected to introduction of random mutations, and screened in the same manner as that described above, as a result of which modified enzymes having a further improved activity in terms of the property of interest can be obtained.

Modification by evolutionary engineering makes it possible to obtain a modified enzyme having an improved property even when the position of the active center of the enzyme is unknown. Such an improvement can be cumulatively achieved by modification by evolutionary engineering, based on an amino acid mutation at an amino acid residue position of which relationship with function is not known in advance, or any combination of two or more of such an amino acid mutation. Therefore, the modification that the DOI synthase according to the present disclosure comprises, and the improvement of the DOI synthesis activity achieved by the modification, cannot be predicted by those skilled in the art.

<Gene Encoding Modified DOI Synthase>

The gene encoding the modified DOI synthase according to the present disclosure may be any nucleic acid that encodes the modified DOI synthase. The nucleotide sequence of a nucleic acid that encodes a particular amino acid sequence can be altered within the limits of codon degeneracy. In this case, it is preferable, from the viewpoint of gene expression efficiency, to use codons of which use frequently in the microorganism serving as the host of the recombinant microorganism is high. According to the present disclosure, a polynucleotide is provided which has a base sequence encoding an amino acid sequence of the modified DOI synthase.

The nucleotide sequence of the gene may also be designed from the amino acid sequence that the nucleotide sequence should encode, based on the codon table. The designed nucleotide sequence may be prepared by modifying a known nucleotide sequence using genetic recombination technology, or by chemically synthesizing the nucleotide sequence.

Examples of methods for modifying nucleotide sequences include site-directed mutagenesis (Kramer, W. and Frita, H. J., *Methods in Enzymology*, vol. 154 (1987), p. 350), recombinant PCR (PCR Technology, Stockton Press (1989)), a method of chemically synthesizing a DNA of a specific region, a method of subjecting a gene to hydroxyamine treatment, subjecting a strain that carries the gene to ultraviolet irradiation treatment or to treatment with a chemical agent such as nitrosoguanidine or nitrous acid, and a method using a commercially available mutagenesis kit.

Various host-vector systems may be used to express a gene that comprise random mutations in the gene of interest. A system such as a bacterium or yeast may be used as the host-vector system. The host-vector system is not particularly limited as long as the system is capable of efficiently expressing and producing the gene having random mutations. The PCR fragment obtained, to which mutations have been introduced, is ligated to an expression vector that has a promoter and a terminator necessary for expression and that can be expressed in a host, and is introduced into the host.

<Modified DOI Synthase Gene Expression Cassette>

The gene expression cassette according to the present disclosure is not particularly limited as long as the gene encoding the aforementioned modified DOI synthase can be expressed in the after-mentioned host cell using the gene expression cassette. The gene expression cassette may include, in addition to the nucleic acid sequence encoding the modified DOI synthase, one or more of, for example, a promoter, an enhancer, RBS (ribosome binding site), or a terminator. The gene expression cassette preferably includes, in addition to the nucleic acid sequence encoding the modified DOI synthase, a promoter located upstream of the nucleic acid sequence and a terminator located downstream of the nucleic acid sequence. For example, in a large-scale protein expression system in which *Escherichia coli* is used as a host cell, a configuration may be adopted in which DNA sequences such as a promoter, an enhancer, and RBS (ribosome binding site) are linked to the upstream side (5'-terminal side) of the DNA sequence encoding the modified DOI synthase, and in which a DNA sequence of, for example, a terminator is linked to the downstream side (3'-terminal side) of the DNA sequence encoding the modified DOI synthase. These elements are not particularly limited as long as they have a sequence that exerts a desired function in *Escherichia coli*. Promoters include constitutive expression promoters and inducible expression promoters. Either type of promoter may be used in the DOI gene expression cassette according to the present disclosure. When *Escherichia coli* is used as the host cell, a promoter with which expression can be induced by an inducer such as IPTG (isopropylthio galactopyranoside) may be used.

For example, in the case of using *Escherichia coli*, examples of the promoter include lactose operon promoter, tryptophan operon promoter, a fusion promoter of the above two promoters, λ-phage promoter, the promoter of glyceraldehyde 3-phosphate dehydrogenase, the promoter of glutamate decarboxylase gene, gadA promoter, and alcohol dehydrogenase (ADH1) promoter. The terminator is not particularly limited, and examples of usable terminators include rrn terminator and AspA terminator.

Moreover, the ribosome binding site is, for example, AGGAG of Shine-Dalgano (SD) sequence. The enhancer to be used may be a known enhancer.

<Modified DOI Synthase Gene Expression Vector>

The modified DOI synthase gene expression vector according to the present disclosure is not particularly limited as long as the modified DOI synthase gene expression vector includes a gene encoding the aforementioned modified DOI synthase and is capable of expression in the after-mentioned host cell. The modified DOI synthase gene expression vector preferably includes the aforementioned modified DOI synthase gene expression cassette.

For example, in the case of using *Escherichia coli*, various expression vectors for efficient gene expression have been constructed. The modified DOI synthase expression vector can be constructed by connecting the mutated gene to be located at downstream of lactose operon promoter, tryptophan operon promoter, a fusion promoter of the above two promoters, λ phage promoter, the promoter of glyceraldehyde 3-phosphate dehydrogenase gene, the promoter of glutamate decarboxylase gene, gadA promoter, alcohol dehydrogenase (ADH1) promoter, or the like, and connecting a terminator to be located downstream of the mutated gene. The terminator to be used is not particularly limited, and may be, for example, rrn terminator or AspA terminator.

A vector for genetic recombination constructed from a phage or plasmid capable of autonomous reproduction in a host cell is suitable as the vector. In the case of using, for example, *Escherichia coli* as the host cell, examples of the phage include Lambda gt10 and Lambda gt11. In the case of using, for example, *Escherichia coli* as a host cell, examples of the plasmid include pBTrp2, pBTac1, and pBTac2 (manufactured by Boehringer Mannheim), pKK233-2 (manufactured by Pharmacia), pSE280 (manufactured by Invitrogen), pGEMEX-1 (manufactured by Promega), pQE-8 and pQE-30 (manufactured by QIAGEN), pBluescript II SK (+) and pBluescript II SK (−) (manufactured by Stratagene), pET-3 (manufactured by Novagen), pUC18, pSTV28, pSTV29, and pUC118 (manufactured by Takara Shuzo Co., Ltd.), pLEX (manufactured by Invitrogen), pQE80L (manufactured by QIAGEN), and pBR322.

The modified DOI synthase gene expression vector may include a promoter for transcription of a DNA encoding the modified DOI synthase. Examples of the promoter include the promoters described above. In addition, the modified DOI synthase gene expression vector may include a ribosome binding sequence. The ribosome binding sequence is, for example, the Shine-Dalgarno sequence, and it is preferable to use a plasmid in which the distance between the SD sequence and the start codon is adjusted to an appropriate distance (for example, from 6 to 18 nucleotides).

In order to perform transcription and translation efficiently, the N-terminal of the protein of interest may be fused to the N-terminal part of another protein encoded by the expression vector.

Although the presence of a terminator is not essential for expression of the protein of interest, a terminator is preferably disposed directly downstream of the structural gene.

For cloning, a vector DNA fragment may be obtained by cleaving the vector as described above with the restriction enzyme or restriction enzymes used for cutting out the DNA to be inserted. However, the restriction enzyme or restriction enzymes to be used need not be the same restriction enzyme or restriction enzymes as the restriction enzyme or restriction enzymes used for cutting out the DNA to be inserted. The method used for combining the DNA fragment to be inserted and the vector DNA fragment may be a method using a known DNA ligase. For example, the sticky end of the DNA fragment to be inserted and the sticky end of the vector DNA fragment. may be allowed to anneal, and then an appropriate DNA ligase may be used to prepare a recombinant DNA formed from the inserted DNA fragment and the vector DNA fragment. After annealing, the DNA fragments may be transferred to a host cell such as a microorganism, if necessary, and the recombinant DNA may be formed using a DNA ligase within the living organism.

The introduction of the recombinant DNA according to the present disclosure into a host cell may be performed using general methods known in the fields of molecular biology, bioengineering and genetic engineering described in, for example, Sambrook, J. et al., "Molecular Cloning: A Laboratory Manual, 3rd Edition" (Cold Spring Harbor Laboratory Press, (2001)). Examples thereof include a method in which a competent cell is used, and a method in which electroporation is used.

By introducing the expression vector, which has been prepared as described above, into a host that allows replication and maintenance of the expression vector, a transformant that expresses the modified DOI synthase gene can be obtained. Then, the properties of the DOI synthase expressed by the obtained transformant may be checked, to verify the modification to the enzyme.

<Transformant>

The transformant according to the present disclosure is a transformant that includes the modified DOI synthase gene expression vector according to the present disclosure.

The host cell used for producing the transformant is not limited as long as the recombinant DNA can stably and autonomously replicate in the cell and features imparted by the foreign DNA can be demonstrated. The host cell is preferably a cell of a microorganism. The cell of the microorganism may be either a cell of a eukaryotic organism (for example, yeast) or a cell of a prokaryotic organism. An example of the host cell is a cell of *Escherichia coli*, but the host cell is not particularly limited to a cell of *Escherichia coli*. Examples of a cell that can be used as the host cell include: a cell of bacterium, for example, a cell of a bacterium belonging to the genus *Escherichia*, a cell of a bacterium belonging to the genus *Bacillus* such as *Bacillus subtilis*, or a cell of a bacterium belonging to the genus *Pseudomonas*; a cell of yeast such as the genus *Saccharomyces, Pichia* or *Candida*; and a cell of filamentous fungus such as the genus *Aspergillus*.

Figure 2:
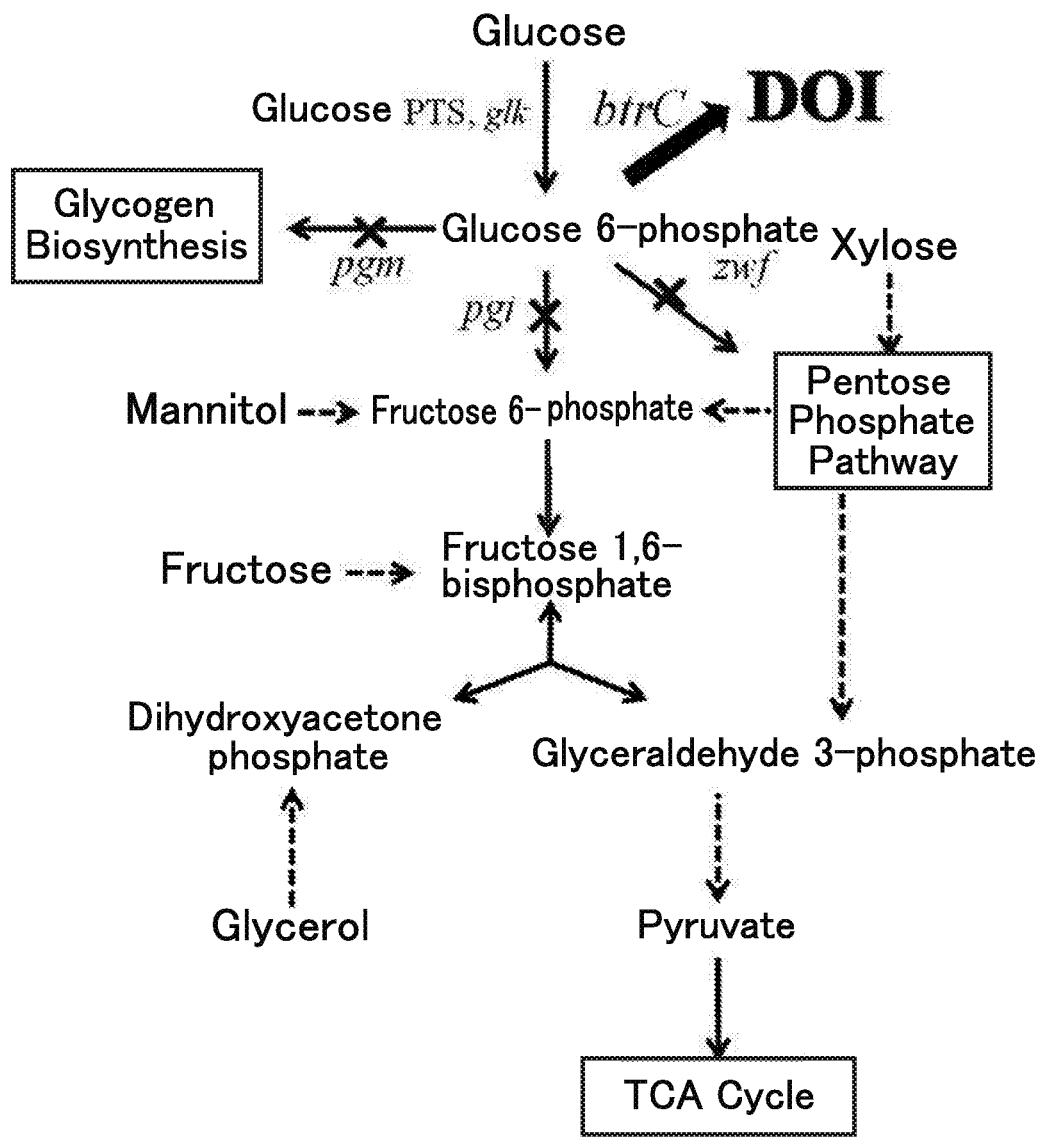
FIG. 2 illustrates a ΔpgiΔzwfΔpgm strain, which has been metabolically engineered to disrupt phosphoglucose isomerase gene (pgi) belonging to the glycolytic pathway, glucose 6-phosphate dehydrogenase gene (zwf) belonging to the pentose phosphate pathway, and phosphoglucomutase gene (pgm) positioned on the way to the glycogen biosynthetic pathway, such that glucose 6-phosphate is preferentially utilized by a DOI synthase (a protein encoded by btrC gene).
Figure 3A:
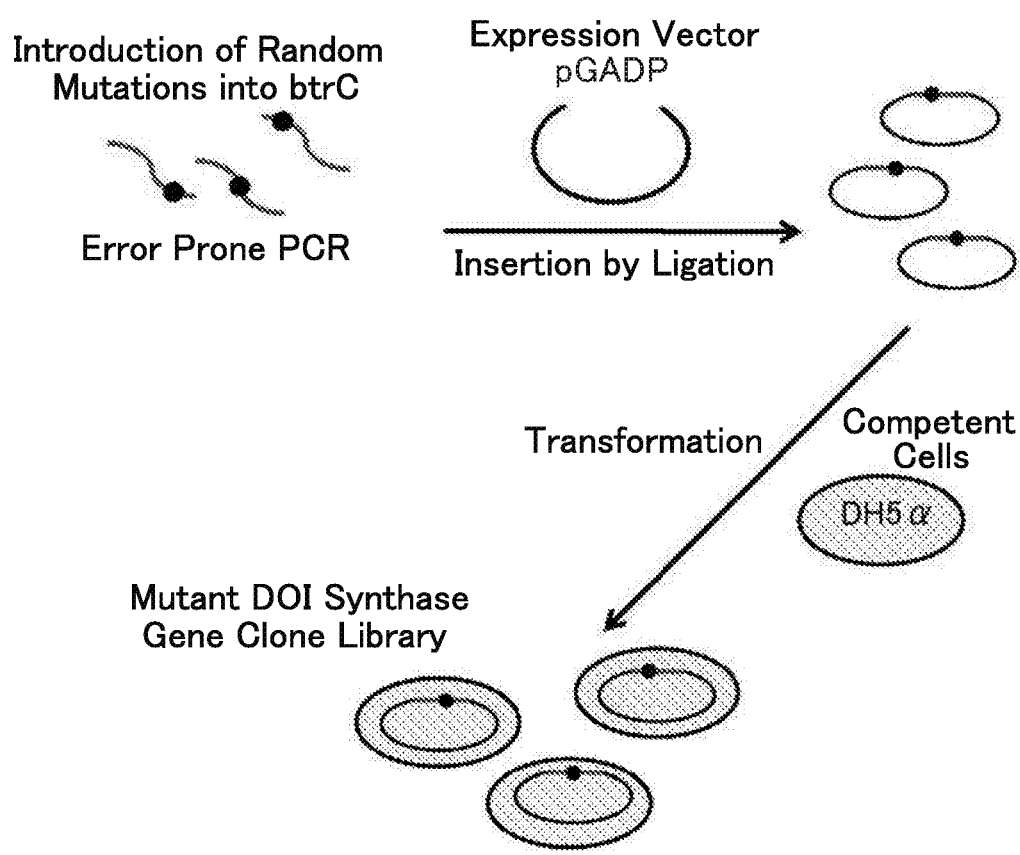
FIG. 3A illustrates preparation of a mutant DOI synthase gene clone library in the process from the preparation of a mutant DOI synthase gene clone library using error prone PCR to isolation of DOI-high-production mutant DOI synthase gene clones (first-stage, second-stage, and third-stage selections).
Figure 3B:
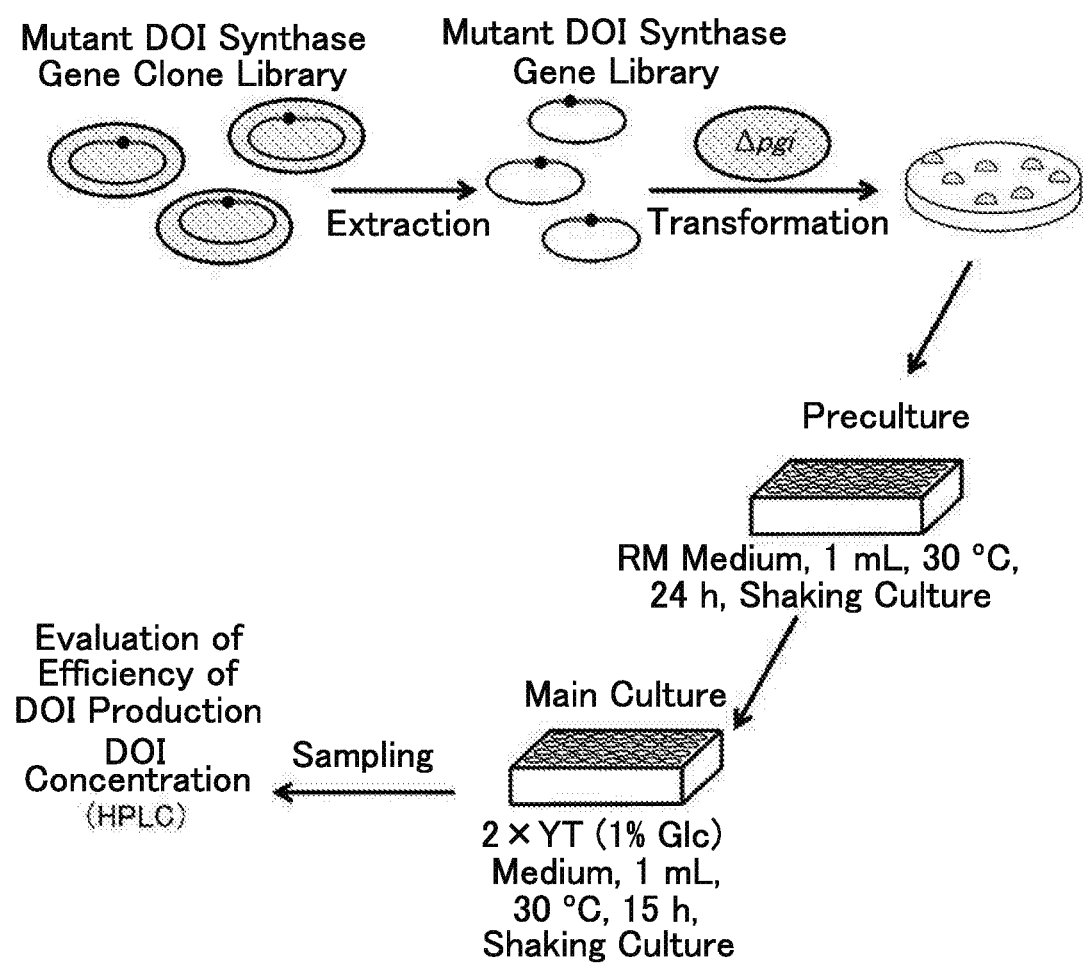
FIG. 3B illustrates first-stage selection in the process from the preparation of a mutant DOI synthase gene clone library using error prone PCR to isolation of DOI-high-production mutant DOI synthase gene clones.
Figure 3C:
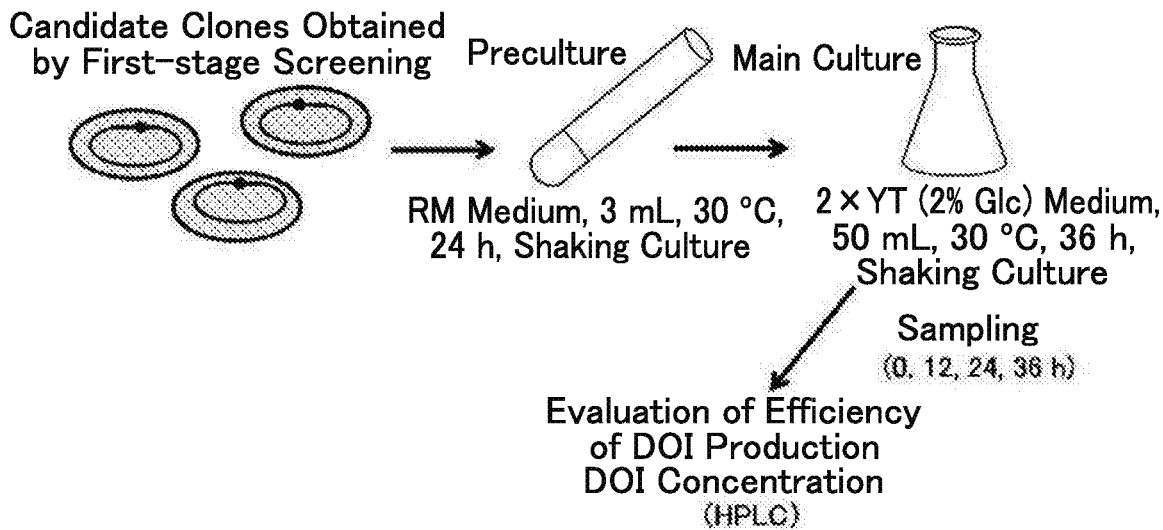
FIG. 3C illustrates second-stage selection in the process from the preparation of a mutant DOI synthase gene clone library using error prone PCR to isolation of DOI-high-production mutant DOI synthase gene clones.
Figure 3D:
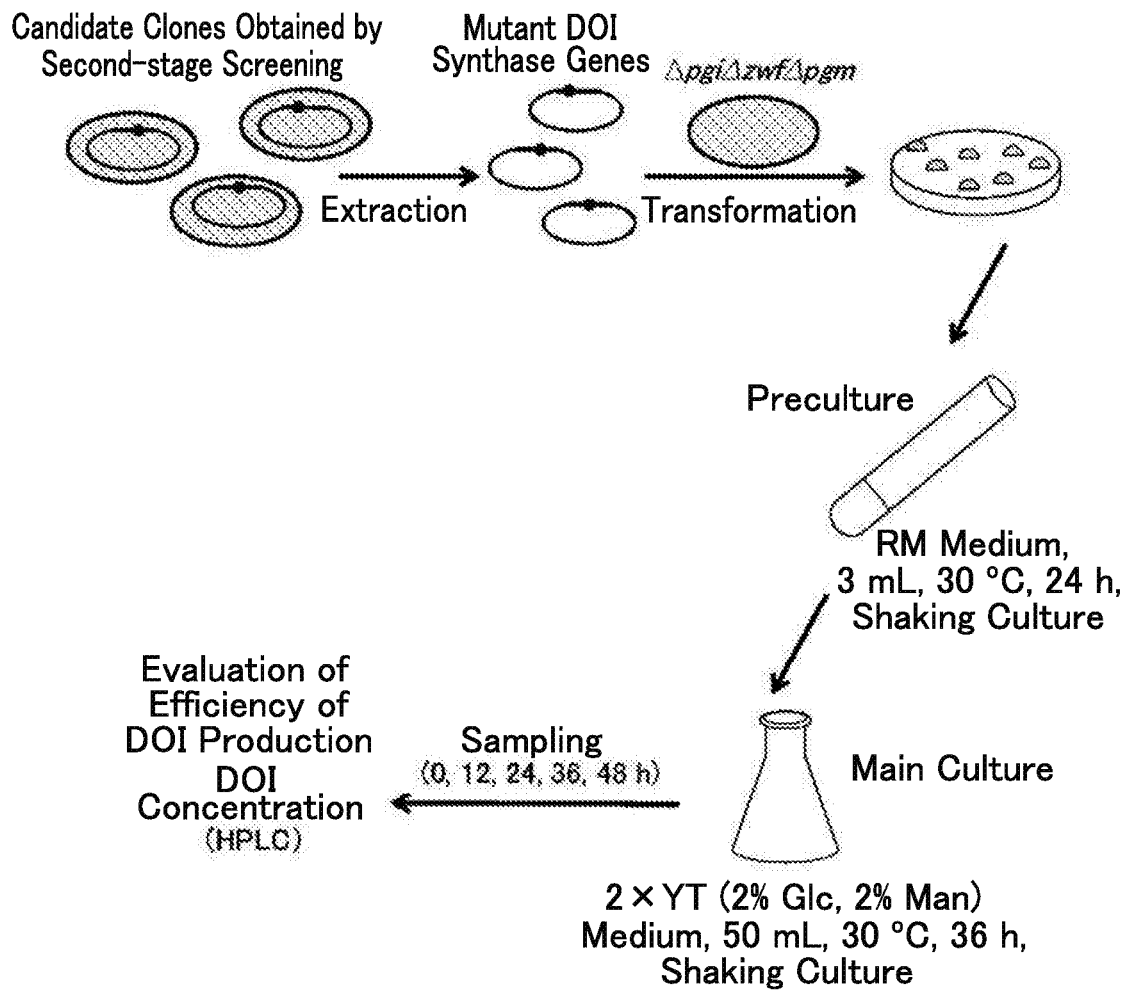
FIG. 3D illustrates third-stage selection in the process from the preparation of a mutant DOI synthase gene clone library using error prone PCR to isolation of DOI-high-production mutant DOI synthase gene clones.

The host cell is preferably a host cell that accumulates a large amount of glucose 6-phosphate, which is a substrate for DOI synthase. Examples of such a host cell include: an *Escherichia coli* strain having disruption of pgi gene, which encodes glucose phosphate isomerase (for example, *Escherichia coli* GI724Δpgi strain described in WO 2006/109479); an *Escherichia coli* strain having disruption of pgi gene and zwf gene, which encodes glucose 6-phosphate dehydrogenase (for example, *Escherichia coli* MG1655ΔpgiΔzwf strain described in WO 2010/053052); and an *Escherichia coli* strain having disruption of pgi gene, zwf gene and pgm gene, which encodes phosphoglucomutase (see FIG. 2) (for example, *Escherichia coli* GI724ΔpgiΔzwfΔpgm strain described in WO 2006/109479).

The host cell is preferably a cell having a gene encoding an enzyme that produces glucose 6-phosphate from glucose, such as glk.

The host cell may be further provided with the ability to import extracellular glucose itself into cells. In order to impart the ability, a gene encoding a glucose transport promoting protein, for example, may further be introduced. Examples of the gene encoding a glucose transport promoting protein include glf from *Zymomonas mobilis*. The host cell may further be provided with improved ability to utilize fructose and sucrose. In order to impart the ability, for example, a sucrose hydrolase gene may further be introduced. The sucrose hydrolase gene is, for example, cscA from *Escherichia coli* 0-157. An example of a vector carrying such a gene is the plasmid vector pGAP-btrC-cscA-glf described in WO 2010/053052.

The method used for transferring the recombinant DNA into the host cell is, for example, a competent cell method involving calcium treatment or an electroporation method in the case of, for example, using *Escherichia coli* as the host cell. The competent cell that can be used is, for example, a competent cell of *Escherichia coli* DH5α. When the transformant obtained in this manner is cultured, the transformant stably produces the modified DOI synthase. The conditions for culturing the transformant are the same as the conditions for culturing the original host microorganism, and known conditions may be used.

Various carbon sources, nitrogen sources, inorganic salts and organic nutrient sources are optionally used in the cultivation of the transformant. Examples of carbon sources that can be used include glucose, sucrose, molasses, oils and fats. Examples of the nitrogen sources include ammonia, ammonium salts such as ammonium chloride, ammonium sulfate and ammonium phosphate, peptone, meat extract, and yeast extract. Examples of the inorganic salts include monopotassium phosphate, dipotassium phosphate, magnesium phosphate, magnesium sulfate, and sodium chloride. Examples of other organic nutrient sources include amino acids such as glycine, alanine, serine, threonine and proline, and vitamins such as vitamin B1, vitamin B12 and vitamin C.

Either a synthetic culture medium or a natural culture medium may be used as long as the culture medium includes appropriate amounts of carbon sources, nitrogen sources, minerals and other nutrients. Examples of culture media include LB liquid culture medium, RM liquid culture medium, 2×YT liquid culture medium, L agar culture medium, and RMM liquid culture medium. Further examples include an LB agar plate. In the case of cultivation of a transformant transformed with an expression vector containing a selection marker: for example, when the selection marker is drug resistance, a culture medium containing the drug corresponding to the drug resistance is used, and, when the selection marker is auxotrophy, a culture medium free of the nutrient corresponding to the auxotrophy is used.

The culture conditions may be appropriately selected in accordance with the type of culture medium and the culture method, and there is no particular limitation as long as the conditions allow growth of the transformant.

The culture temperature may be any temperature at which the transformant can grow. The pH during cultivation may be any pH at which the transformant can grow. The culture period is not particularly limited as long as the DOI synthase can efficiently be produced during the culture period.

The culture temperature may be a temperature in the range of, for example, from 20° C. to 45° C., and may be a temperature in the range of from 25° C. to 35° C., and may be a temperature in the range of from 24° C. to 37° C. The pH of the culture medium may be selected, for example, from the range of from 4 to 8, and the pH of the culture medium may be in the range of from 5 to 8, and may be in the range of from 6.5 to 8. Culturing may be performed aerobically or anaerobically, depending on the type of microorganism.

The culture period is, for example, from 1 hour to 7 days. The culture period may be from 6 hours to 60 hours, and may be from 12 hours to 30 hours. The culture period may be set to maximize the production amount of the modified DOI synthase. For example, when cultivation is carried out under aerobic conditions at a pH of from 6 to 8 and a temperature of from 25° C. to 40° C. with an appropriate control of the pH and the temperature, the time required for the cultivation may be set to 48 hours or less. The culture period may be in the range of from 0.5 hours to 30 hours.

The cultivation may be carried out in a liquid culture medium that includes the above-described components for cultivation, using a general cultivation method such as shaking culture, aeration culture under agitation, continuous culture or fed-batch culture.

The transformant obtained is cultured under conditions in which the transformant can produce DOI, and the status concerning the production amount of DOI in the culture liquid is checked. For example, the status concerning the production amount of DOI may be checked using a gas chromatograph mass spectrometer or a high performance liquid chromatograph analyzer. The analysis of the production amount may be performed with reference to Kogure et al., *J. Biotechnol.* vol. 129(2007), p. 502.

The expression vector is extracted from a transformant that exhibited an altered status concerning the DOI production amount in the above analysis, and the base sequence of the gene that encodes the enzyme is determined. The expected amino acid sequence of the enzyme is compared with the amino acid sequence of the wild type enzyme, thereby identifying which amino acids are contributing to the alteration in the properties of the enzyme.

When plural amino acid substitutions are found on the expected amino acid sequence of the enzyme having altered properties, the degree of contribution of each amino acid substitution in terms of the alteration of the properties of the enzyme can be examined by replacing any one amino acid by another amino acid using site-directed mutagenesis.

The alteration in the enzymological properties of the mutant enzymes obtained above may be confirmed by determining, for example, the specific activity, substrate specificity, optimum temperature, and optimum pH of each mutant enzyme after isolation and purification of the mutant enzyme, and comparing the determined properties with those of the wild type enzyme.

The modified DOI synthase produced by the transformant may be used in the form of a culture liquid containing the transformant in the culture product that has been collected as it is. Alternatively, the modified DOI synthase may be used after collecting the transformant from the obtained culture product using a means such as filtration or centrifugation. The collected transformant may be disrupted by a mechanical method or an enzymatic method such as lysozyme, and a chelating agent such as ethylenediaminetetraacetic acid (EDTA) and/or a surfactant may be added, if necessary, to solubilize the polypeptide, in which case the modified DOI synthase can be separated and collected in the form of a solution.

<Method of Producing Modified DOI Synthase>

The method of producing a polypeptide having a DOI synthesis activity (the modified DOI synthase) according to the present disclosure includes culturing the transformant according to the present disclosure. The culture medium, culture conditions, cultivation method and other details used for culturing the transformant are as described in the description of the transformant according to the present disclosure. The culture conditions are not particularly limited as long as the host cells can grow and produce the protein having a DOI synthesis activity under the conditions.

By culturing the transformant according to the present disclosure, the gene encoding the modified DOI synthase on the vector according to the present disclosure is expressed to produce the modified DOI synthase. For example, the modified DOI synthase can be obtained by cultivation in an appropriate culture medium at a pH in the range of from 6 to 8 and a temperature in the range of from 25° C. to 40° C. for 48 hours or less under aerobic conditions.

The modified DOI synthase produced is included in at least one of a cell of the transformant (for example, a cell of *Escherichia coli*) or the culture medium. The cell of the transformant and the culture medium may be used, as they are, for a DOI synthesis reaction without purification, or the modified DOI synthase may be purified from the culture medium. In the latter case, the modified DOI synthase contained in the cells can also be collected by homogenizing or lysing the cells. Alternatively, the cells may be separated from the culture medium by, for example, centrifugation, and the separated cells may be used in a DOI synthesis reaction, or the separated cells may be stored after drying, freezing or lyophilization. Alternatively, the separated cells may be homogenized or lysed, and the released DOI synthase may be used, as it is, in a DOI synthesis reaction, or the released DOI synthase may be purified. For the purification of the enzyme, a general purification method such as centrifugation, salting out, desalting, chromatography, electrophoresis, or ultrafiltration may be used under appropriately adjusted conditions. For example, the DOI synthase can be purified by cell lysis using Lysis buffer, immobilization of the DOI synthase on Ni-NTA agarose, and elution of the DOI synthase using an elution buffer.

<Method of Manufacturing DOI>

The method of producing DOI according to the present disclosure includes: contacting the modified DOI synthase according to the present disclosure, the transformant according to the present disclosure, the culture product of the transformant, or a processed product of the transformant or the culture product with glucose or glucose 6-phosphate, thereby converting glucose or glucose 6-phosphate to DOI.

The culture product of the transformant refers to a product obtained by culturing the transformant, the culture product including cells, surrounding culture medium, and the like. It is not essential to use the culture product. For example, dried or frozen cells of the transformant, which have been prepared in advance, may directly be added to the reaction system.

The culture medium, culture condition, cultivation method, and other details for obtaining the culture product of the transformant are the same as the above-described culture medium, culture conditions, cultivation method and the like that can be used for the cultivation of the transformant. The culture conditions are not particularly limited as long as the host cells can grow and produce a protein having a DOI synthesis activity under the conditions.

In addition, the processed product of the transformant refers to a product obtained by subjecting the transformant to a freely selected treatment with a proviso that the activity of the modified DOI synthase produced by the transformant is not lost by the treatment. The treatment is, for example, a treatment that includes at least one selected from the group consisting of heat treatment, cooling treatment, mechanical crushing, ultrasonication treatment, freeze-thaw treatment, drying treatment, treatment of increasing or decreasing pressure, osmotic pressure treatment, autolysis, treatment with a surfactant, and treatment with an enzyme (for example, cell lysis treatment). Even if the transformant itself is killed by the treatment, the processed product can be used in the reaction as long as the activity of the enzyme produced by the transformant remains.

The processed product of the culture product refers to a product obtained by subjecting the culture product of the transformant to a freely selected treatment with a proviso that the activity of the modified DOI synthase produced by the transformant is not lost by the treatment. The treatment is, for example, a treatment that includes at least one selected from the group consisting of heat treatment, cooling treatment, mechanical crushing of cells, ultrasonication treatment, freeze-thaw treatment, drying treatment, treatment of increasing or decreasing pressure, osmotic pressure treatment, cell autolysis, treatment with a surfactant, treatment with an enzyme (for example, cell crushing treatment), cell separation treatment, purification treatment and extraction treatment. For example, cells of the transformant may be separated from the culture medium or the like, and the separated cells may be added to the reaction system. For the separation, a means such as filtration or centrifugation can be used. Alternatively, purification treatment may be performed to separate the modified DOI synthase from contaminants, and the enzyme-containing solution obtained by the purification treatment may be added to the reaction system. Alternatively, an extract obtained by extracting the culture product using an organic solvent such as methanol or acetonitrile or a mixed solvent of an organic solvent and water may be added to the reaction system. The purified product or extract may be free of transformant cells. Even if cells of the transformant are absent, the purified product or extract can be used in the reaction as long as the enzymatic activity remains.

The crushing or lysis treatment of the cells such as those described above can be carried out by disrupting the cell membrane of the transformant according to a known method such as lysozyme treatment, freeze-thaw, or ultrasonication.

The contact between glucose or glucose 6-phosphate and the transformant according to the present disclosure, the culture product of the transformant, or the processed product of the transformant or the culture product is preferably performed under the following conditions.

The contact is preferably performed in a solution that includes glucose or glucose 6-phosphate as a substrate. Of course, it is permissible for the solution to include both glucose and glucose 6-phosphate. The reaction is preferably carried out in the presence of a coenzyme such as NAD or NADP, from the viewpoint of, for example, the reaction efficiency.

The reaction conditions are not particularly limited as long as the reaction proceeds under the conditions. For example, the pH of the solution is not particularly limited as long as the enzymatic activity of the modified DOI synthase is retained, and the pH at the time of the reaction is, for example, preferably in the range of from 4.0 to 9.0, preferably in the range of from 5.0 to 8.0, and more preferably in the range of from 6.0 to 8.0. The temperature of the solution is also not particularly limited as long as the enzymatic activity of the modified DOI synthase is retained, and the temperature is preferably in the range of from 10° C. to 50° C., more preferably in the range of from 20° C. to 45° C., and still more preferably in the range of from 30° C. to 42° C.

As the medium of the solution, water, an aqueous medium, an organic solvent, or a mixture liquid of (i) water or an aqueous medium and (ii) an organic solvent is used. The aqueous medium that may be used is, for example, a buffer solution such as a phosphate buffer solution, a HEPES (N-2-hydroxyethyl piperazine-N-ethanesulfonic acid) buffer solution, and a tris [tris (hydroxymethyl) aminomethane] hydrochloride buffer solution. The organic solvent may be any organic solvent that does not inhibit the reaction, and examples of the organic solvent that can be used include acetone, ethyl acetate, dimethyl sulfoxide, xylene, methanol, ethanol, and butanol. The solution may alternatively be a liquid culture medium.

The contact between glucose or glucose 6-phosphate and the transformant, the culture product of the transformant, or the processed product of the transformant or the culture product according to the present disclosure is preferably carried out under shaking or stirring. For example, the contact may be carried out in a solution. For example, glucose or glucose 6-phosphate may be added, in the form of a substrate solution or in the form of a solid, to a solution that includes the transformant, the culture product of the transformant, or the processed product of the transformant or the culture product.

An acid or an alkali may be added at the start of the reaction or at some time in the reaction, so as to maintain the pH of the reaction solution in an appropriate range. Examples of alkalis that can be added to the reaction solution include alkali metal hydroxides such as lithium hydroxide, sodium hydroxide and potassium hydroxide, and other substances that dissolve in water to shift the pH to be basic, such as ammonium hydroxide, calcium hydroxide, dipotassium phosphate and disodium phosphate, potassium pyrophosphate, and ammonia. Examples of acids that can be added to the reaction solution include hydrochloric acid, sulfuric acid, nitric acid, acetic acid, and phosphoric acid.

The contact may be performed, for example, in the air atmosphere or in a deoxygenated atmosphere. The deoxygenated atmosphere can be achieved by substitution with an inert gas, pressure reduction, boiling, or any combination thereof. It is preferable to use at least substitution with an inert gas, in other words, an inert gas atmosphere. Examples of the inert gas include nitrogen gas, helium gas, argon gas, and a carbon dioxide gas, and the inert gas is preferably nitrogen gas.

In a preferred embodiment, the transformant, the culture product of the transformant, or the processed product of the transformant or the culture product to be used includes the modified DOI synthase. Therefore, as a result of the above contact, the modified DOI synthase co-present in the reaction solution acts to produce DOI with high production efficiency. It is not essential that the processed product of the transformant or the processed product of the culture product include the transformant in the living state. From the viewpoint that the substance involved in the reaction can continuously be supplied by metabolism, the processed product of the transformant or the processed product of the culture product preferably includes the transformant in the living state.

With regard to the timing of the addition, the transformant, the culture product of the transformant, or the processed product of the transformant or the culture product may be added at once at the start of the reaction, or added in portions during the reaction, or continuously added during the reaction. Similarly, glucose or glucose 6-phosphate, which serves as a raw material, may be added at once at the start of the reaction, or added in portions during the reaction, or continuously added during the reaction.

The concentration of glucose or glucose 6-phosphate in the reaction solution is, for example, from 0.1% by mass to 20% by mass, or from 0.5% by mass to 15% by mass, or from 2% by mass to 10% by mass.

Examples of the method that can be used for contacting glucose or glucose 6-phosphate with the transformant, the culture product of the transformant, or the processed product of the transformant or the culture product include: a method including adding the transformant, the culture product of the transformant, or the processed product of the transformant or the culture product to a solution containing glucose or glucose 6-phosphate, and allowing the reaction to proceed while stirring; a method including adding the transformant, the culture product of the transformant, or the trait processed product of the transformant or the culture product to a solution containing glucose or glucose 6-phosphate, and allowing the reaction to proceed while agitating; and a method including sufficiently mixing, in a solution, pyridoxine or a salt thereof and the transformant, the culture product of the transformant, or the processed product of the transformation or the culture product with sufficiently, and thereafter allowing the solution to stand, thereby allowing the reaction to proceed. From the viewpoint of reaction efficiency, the method is preferably which includes adding the transformant, the culture product of the transformant, or the processed product of the transformant or the culture product to a solution containing glucose or glucose 6-phosphate, and allowing the reaction to proceed while agitating.

There is no particular restriction on reaction vessels that can be used for the reaction. The reaction vessel is preferably a reaction vessel that can agitate the solution that includes pyridoxine or a salt thereof and the added transformant, culture product of the transformant, or processed product of the transformant or the culture product to achieve sufficient mixing, and that has a temperature control function enabling the temperature to be maintained within the optimum temperature range of the modified DOI synthase.

The contact period of the transformant, the culture product of the transformant, or the processed product of transformant or the culture product with glucose or glucose 6-phosphate (reaction time) is not particularly limited as long as the enzymatic activity of the modified DOI synthase is retained. The contact period may be, for example, from 30 minutes to 100 hours, and may be from 2 hours to 50 hours. In addition, the reaction may be performed in a batch manner, or in a semi-batch manner in which one of (i) the substrate or (ii) the microorganism, the culture product, or the processed product, or both, is/are added one or more times during the reaction, or in a continuous manner. In the case of the semi-batch manner or the continuous manner, since an operation, such as supply of one of (i) a new raw material or (ii) the transformant, the culture product, or the processed product, or both, is performed, the upper limit of the reaction time is not particularly limited. For example, glucose or glucose 6-phosphate may be added continuously.

In one embodiment, the method of producing DOI comprises culturing the transformant according to the present disclosure in a culture medium. The culture medium is preferably a liquid culture medium, and preferably includes glucose or glucose 6-phosphate. In the case of a transformant having an improved fructose utilization ability imparted by, for example, introduction of cscA, the culture medium may further include fructose. With regard to culture media, culture conditions, cultivation methods, and the like that can be used, the above-described culture media, culture conditions, cultivation methods and the like that can be used in the cultivation of the transformant can be applied. For example, 2×YT liquid culture medium or the like can be used. The culture medium may be made to include a desired concentration of glucose or glucose 6-phosphate by adding glucose or glucose 6-phosphate to the culture medium. The culture temperature is, for example, in the range of from 25° C. to 35° C., and the culture period is, for example, from 5 hours to 30 hours. The concentration of glucose or glucose 6-phosphate in the culture medium is, for example, from 0.1% by mass to 20% by mass, or from 0.5% by mass to 15% by mass, or from 1.5% by mass to 10% by mass. DOI is produced in the cultivation due to the presence of the transformant.

The transformant may be precultured prior to cultivation for DOI production (hereinafter also referred to as "main culture"). The culture medium used for the pre-culture may be a culture medium that is different from the culture medium used for the cultivation for DOI production. The difference in culture medium may comprise a difference in basal medium, and may comprise a difference in the concentration of glucose or glucose 6-phosphate. With regard to the culture medium, culture conditions, cultivation method and the like used for the pre-culture, the above-described culture media, culture conditions, cultivation methods and the like that can be used for cultivation of the transformant may be applied. The culture medium used for the pre-culture may be a culture medium that includes neither glucose nor glucose 6-phosphate. Examples of the culture medium used for the pre-culture include RM liquid culture medium and RMM liquid culture medium, and further include 2×YT liquid culture medium. The pre-culture may be performed until the state of the transformant becomes stable. The pre-culture period is, for example, from 3 to 48 hours, and may be from 8 to 30 hours. The pre-cultured transformant may be added, together with the surrounding culture medium, to the culture medium for the main culture, or added to the culture medium for the main culture after the transformant is separated from the culture medium used for the pre-culture by, for example, centrifugation. Usually, the culture liquid amount of the main culture may be made greater than the culture liquid amount of the preculture, for example, at least 10 times greater than the culture liquid amount of the preculture by volume, or at least 20 times greater than the culture liquid amount of the preculture by volume.

The main culture may be carried out in a batch manner, or in a semi-batch manner in which glucose or glucose 6-phosphate is added one or more times during the reaction, or in a continuous manner in which glucose or glucose 6-phosphate is continuously added. In the case of the semi-batch manner or the continuous manner, since an operation such as supply of a new raw material is performed, the upper limit of the reaction time is not particularly limited.

According to the above method, DOI can be produced at high production efficiency by using glucose or glucose 6-phosphate as a raw material and the transformant, the culture product, or the processed product of the transformant or the culture product according to the present disclosure. The DOI obtained by the above method can be converted, for example, to catechol, which can be used as a raw material for medicines for the nerve system, a raw material for flavors, or an antioxidant for hair care products, or to hydroquinone, which can be used as raw materials for hemostatic agents and analgesics, or used in cosmetics such as skin whitening agents. By dehydrating the DOI obtained by the above method, 1,2,4-trihydroxybenzene (THB) can be obtained. Furthermore, by converting the hydroxyl groups of THB obtained by the above method to glycidyl ethers, 1,2,4-triglycidyloxybenzene (TGB) can be obtained. TGB has excellent heat resistance, and is a low-viscosity liquid at normal temperature. TGB can be used over a wide range such as sealing materials for electronic parts, circuit substrates, adhesives, coating materials, paints, and matrix resins for composite materials.

In the present specification, the term "process" encompasses not only an independent process, but also a process that cannot be clearly distinguished from other processes as long as the intended purpose of the process is achieved. Further, in the present specification, a numerical range expressed using "to" indicates a range including numerical values noted before and after "to" as the minimum and maximum values.

When the amount of a particular component in a composition is indicated in the present specification and there are plural substances corresponding to the particular component in the composition, the indicated amount refers to the total amount of the plural substances present in the composition.

EXAMPLES

Hereinafter, embodiments will be specifically described by reference to examples, but the technical scope of present disclosure is not to be limited by these examples. In the examples, "%" used to indicate the content or addition amount of a substance represents "% by mass" unless specified otherwise.

Example 1

<Construction of Mutant DOI Synthase Gene Clone Library by Error Prone PCR>

Processes from preparation of mutant DOI synthase gene clone library using error prone PCR to isolation of DOI-high-production mutant DOI synthase gene clones (first-stage, second-stage and third-stage selections) are shown in FIG. 3A to FIG. 3D.

Mutations were randomly introduced into a gene (btrC) encoding the amino acid sequence of the DOI synthase from *Bacillus circulans* shown in SEQ ID NO: 1, using error prone PCR. The PCR was performed under the conditions in which the accuracy of the DNA polymerase decreases (Table 2), using a plasmid pLEX-btrC (a plasmid described in WO 2006/109479, obtained by inserting the btrC gene encoding the 42 kDa subunit of the DOI synthase from *Bacillus circulans* into NdeI-XbaI site in the multi-cloning site of the vector pLEX (Invitrogen)), which includes the entire length of the btrC gene, as a template, and using primer 1 (5'-acgcgtcgacatgacgactaaacaaatttg-3') of SEQ ID NO: 2, which corresponds to a nucleotide sequence obtained by adding a SalI restriction site to an upstream position of the start codon of the btrC gene, and primer 2 (5'-aaaactgcagtta-cagcccttcccgga-3') of SEQ ID NO: 3, which corresponds to a nucleotide sequence obtained by adding a PstI restriction site to an upstream position of the stop codon of the btrC gene, thereby performing introduction of random mutations into the entire region of the btrC gene without limiting the mutation sites.

TABLE 2

| Error-prone PCR Reaction Conditions | |
|---|---|
| Tris-HCl (pH 8.3) | 10 mM |
| KCl | 50 mM |
| MgCl$_2$ | 7 mM |
| MnCl$_2$ | 0.5 mM |
| dATP | 0.2 mM |
| dCTP | 1 mM |
| dGTP | 0.2 mM |
| dTTP | 1 mM |
| Template Plasmid DNA | 10 ng |
| Primer 1 | 20 μM |
| Primer 2 | 20 μM |
| Takara Ex Taq DNA Polymerase | 5 units |
| dH$_2$O | 50 μL |

After holding at 94° C. for 2 minutes and 30 seconds, PCR was carried out for 30 cycles, each of which comprises heat denaturation at 94° C. for 20 seconds, annealing at 50° C. for 25 seconds, and DNA extension reaction at 72° C. for 1 minute and 10 seconds. Then it was held at 72° C. for 3 minutes, and the PCR amplification products obtained were retained at 4° C.

The DNA fragments amplified by the PCR amplification were treated with phenol/chloroform, and then centrifuged. The supernatant was subjected to ethanol precipitation, and the DNA fragments were recovered. The recovered DNA fragments were digested with restriction enzymes SalI and PstI, and purified and isolated by agarose gel electrophoresis, to obtain DNA fragments of mutant DOI synthase genes.

Then, expression vectors for expressing the DNA fragments of the mutant DOI synthase genes in host cells (*Escherichia coli*) were constructed. Specifically, PCR amplification was performed using pLEX vector (Invitrogen) as a template, primer 3 of SEQ ID NO: 4 (5'-atggtaccgagctcggatcc-3') and primer 4 of SEQ ID NO: 5 (5'-ctagtctagactaggagataatttatcaccgcag-3'), the nucleotide sequence of which has an added XbaI restriction site at its 5'-side position. KOD polymerase (TOYOBO) was used for the PCR amplification. After holding at 94° C. for 2 minutes, PCR was carried out for 30 cycles, each of which comprises heat denaturation at 94° C. for 30 seconds, annealing at 52° C. for 30 seconds, and DNA extension reaction at 68° C. for 1 minute. Then it was held at 68° C. for 2 minutes, and the PCR amplification products obtained were retained at 4° C. The DNA fragment obtained by the PCR amplification was treated with phenol/chloroform, and then centrifuged. The supernatant was subjected to ethanol precipitation, and the DNA fragment was recovered. The recovered DNA fragment was digested with restriction enzymes SalI and XbaI, and purified and isolated by agarose gel electrophoresis, to obtain a DNA fragment of the expression vector.

Subsequently, gadA promoter was obtained as a promoter for expressing the DNA fragment of the mutant DOI synthase gene in a host cell (*Escherichia coli*). Specifically, gadA promoter was obtained as follows. PCR amplification was performed using the chromosomal DNA of *Escherichia coli* as a template, primer 5 (5'-ctagtctagagtcgtttttctgct-3') of SEQ ID NO: 6, the nucleotide sequence of which has an added XbaI restriction site at its 5'-side position, and primer 6 (5'-acgcgtcgacttcgaactccttaaatttatttgaaggc-3') of SEQ ID NO: 7, the nucleotide sequence of which has an added SalI restriction site at its 5'-side position. KOD polymerase (TOYOBO) was used for PCR amplification. After holding at 94° C. for 2 minutes, PCR was carried out for 30 cycles, each of which comprises heat denaturation at 94° C. for 30 seconds, annealing at 50° C. for 30 seconds, and DNA extension reaction at 68° C. for 1 minute. Then it was held at 68° C. for 2 minutes, and the PCR amplification products obtained were retained at 4° C. The DNA fragment amplified by the PCR amplification was treated with phenol/chloroform, and then centrifuged. The supernatant was subjected to ethanol precipitation, and the DNA fragment was recovered. The recovered DNA fragment was digested with restriction enzymes SalI and XbaI, and purified and isolated by agarose gel electrophoresis, to obtain a DNA fragment of gadA promoter.

Figure 4:
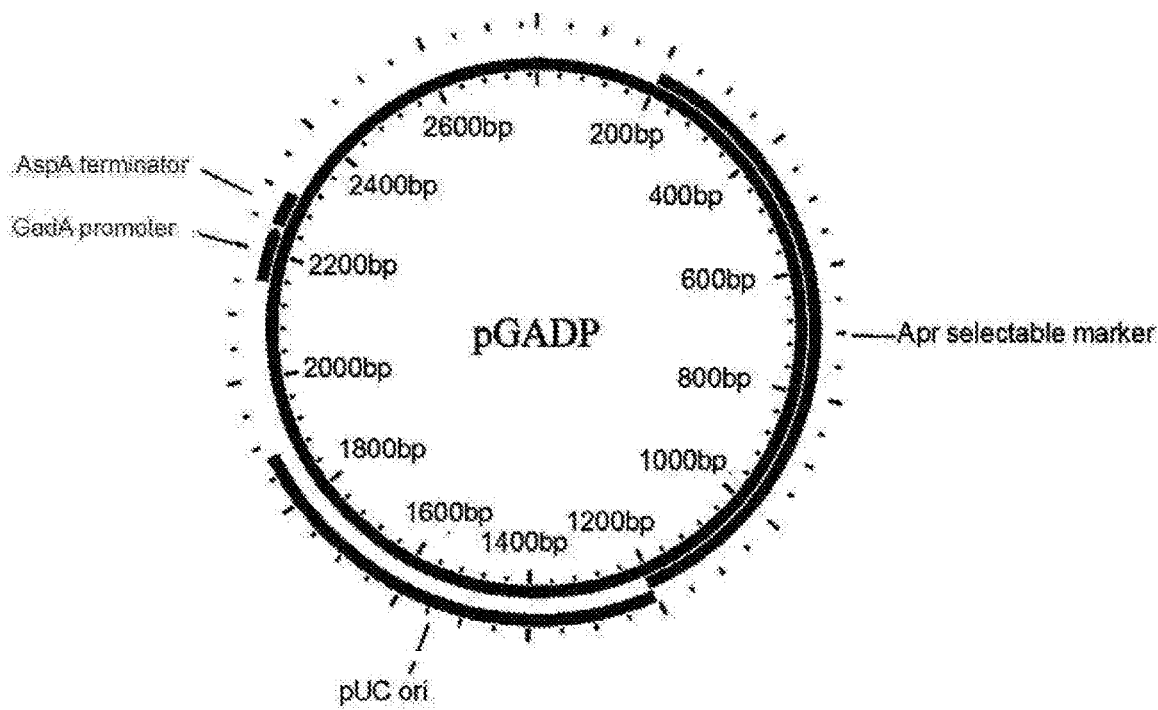
FIG. 4 illustrates the structure of pGADP.

Then, the DNA fragment of the expression vector and the DNA fragment of gadA promoter, which were amplified as described above, were subjected to a reaction at 16° C. for 30 minutes using 2×Ligation Mix, thereby inserting the DNA fragment of gadA promoter into the DNA fragment of the expression vector by ligation. As a result, an expression vector pGADP (FIG. 4) was obtained.

The expression vector pGADP obtained by the above operation was digested with restriction enzymes SalI and PstI, and purified and isolated by agarose gel electrophoresis. Further, the DNA fragments of the mutant DOI synthase genes were inserted thereinto by ligation, whereby a population of molecules of the modified DOI synthase genes (mbtrC) were obtained.

Competent cells of Escherichia coli DH5α were transformed with the population of molecules obtained by the above operation, thereby constructing a mutant DOI synthase gene clone library.

Example 2

<Isolation of DOI-High-Production Mutant DOI Synthase Gene Clone>

Figure 5:
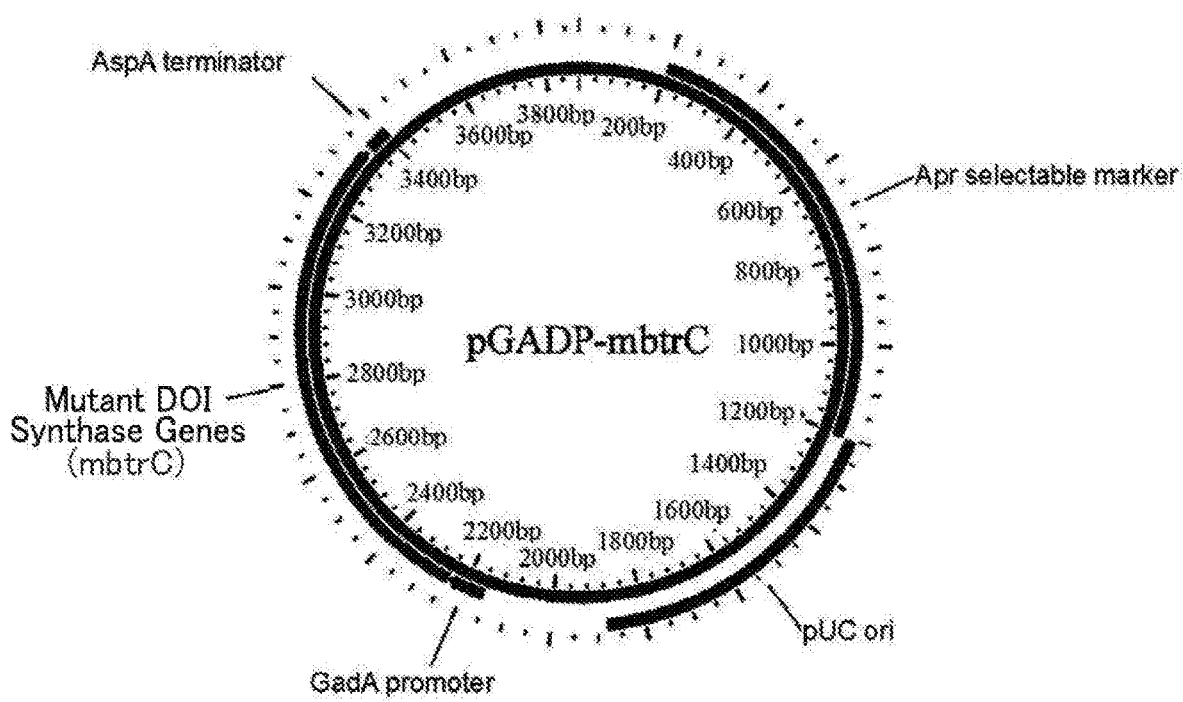
FIG. 5 illustrates the structure of pGADP-mbtrC.

A mutant DOI synthase gene library (pGADP-mbtrC, FIG. 5) was extracted from the mutant DOI synthase gene clone library obtained by the above operation, and competent cells of Escherichia coli GI724Δpgi strain (the strain obtained by disrupting the pgi gene in Escherichia coli GI724 strain, described in WO 2006/109479 and Kakinuma et al., Tetrahedron Letters, vol. 41(2000), p. 1935), which is a strain highly accumulating glucose 6-phosphate (a substrate of the DOI synthase), were transformed with the mutant DOI synthase gene library. The transformed cells were cultured on an L agar culture medium (1% tryptone, 0.5% yeast extract, 0.5% NaCl, 2% agar, 100 µg/mL ampicillin), and grown clones were used for selection and isolation of mutant DOI synthase gene clones.

In the first-stage selection, first, the obtained clones from which selection was to be made were inoculated into wells of a 96-well deep well plate each having a round bottom and each containing 1 mL of RM liquid culture medium (2% casamino acids, 1% glycerol, 0.6% $Na_2HPO_4$, 0.3% $KH_2PO_4$, 0.05% NaCl, 0.1% $NH_4Cl$, 1 mM $MgCl_2$, 100 µg/mL ampicillin), and pre-cultured while shaking at 30° C. for 24 hours. Next, 10 µL of each of the pre-culture liquid was inoculated into wells of a 96-well deep well plate each having a round bottom and each containing 1 mL of 2×YT liquid culture medium (1.6% tryptone, 1% yeast extract, 0.5% NaCl, 1% glucose, 100 µg/mL ampicillin) for first-stage selection, and main-cultured while shaking at 30° C. for 15 hours. Each of the culture liquids after main culture was centrifuged to remove the bacterial cells, and 10 µL of the supernatant, 90 µL of sterile distilled water, 100 µL of methanol, and an oximation reagent NBHA (20 mg/mL) were mixed and subjected to oximation reaction at 60° C. for 1 hour. After the oximation reaction, the reaction solution was dried to solid using a centrifugal evaporator, and re-dissolved in 200 µL of methanol. Thereafter, HPLC analysis was performed under the conditions indicated in Table 3, the DOI concentration was determined, and candidate clones that exhibited a greater DOI production amount than that of a clone having the wild type DOI synthase gene were selected.

TABLE 3

| HPLC Analysis Conditions in Measurement of DOI Amount | |
|---|---|
| Column | PHENOMENEX KINETEX XB-C18 100 Å |
| Eluent | $H_2O$/Methanol (80/20) |
| Flow Rate | 0.7 mL/min |
| Column Temperature | 40° C. |
| Detection | UV262 nm |
| Charge Amount | 2 µL |

The candidate clones obtained by the first-stage selection were subjected to second-stage selection. In the second-stage selection, the candidate clones obtained in the first-stage selection were inoculated into test tubes each containing 3 mL of RM liquid culture medium, and pre-cultured while shaking at 30° C. for 24 hours. Next, the pre-culture liquids were inoculated into 500 mL Erlenmeyer flasks each containing 50 mL of 2×YT liquid culture medium (1.6% tryptone, 1% yeast extract, 0.5% NaCl, 2% glucose, 100 µg/mL ampicillin) for second-stage selection such that the turbidity OD600 became 0.1, and main culture was performed while shaking at 30° C. for 36 hours. Culture liquids obtained at 0, 12, 24, and 36 hours after the start of the main culture were centrifuged to remove the bacterial cells, and the same operation as the DOI concentration measurement operation in the first-stage selection was performed on 10 µL of each supernatant to determine a DOI concentration using HPLC. Candidate clones that exhibited a greater DOI production amount than that of a clone having the wild type DOI synthase gene of the amino acid sequence of SEQ ID NO: 1 were selected.

Figure 6:
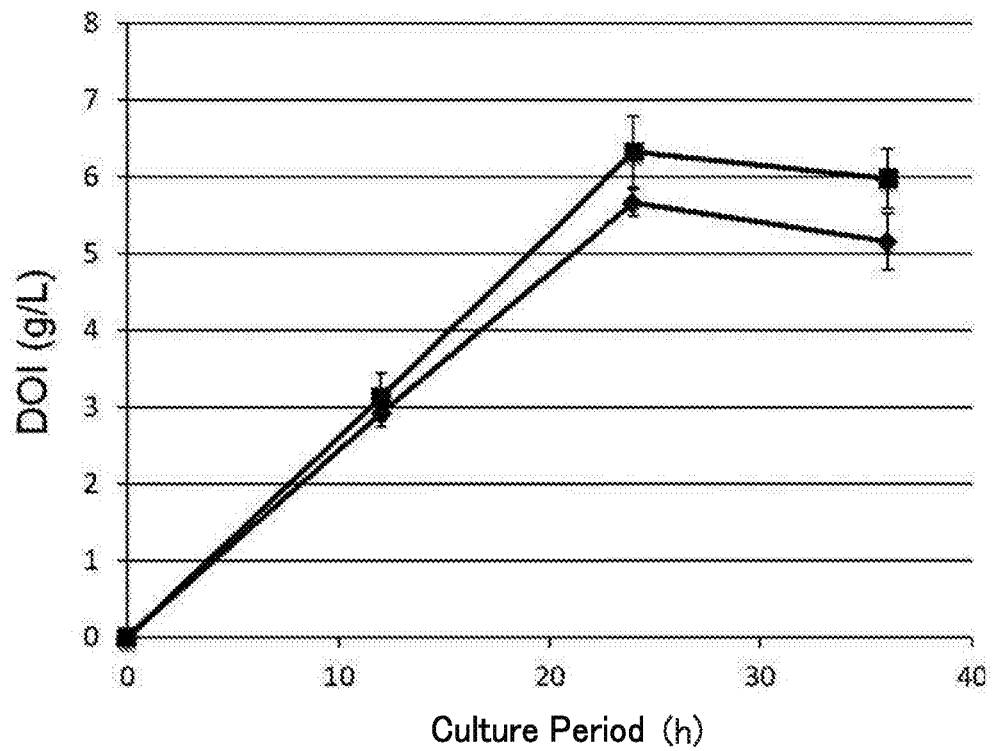
FIG. 6 shows a time course of DOI production amount in the culture medium during cultivation (2×YT+2% glucose+2% mannitol, 50 mL, 30° C.) of an *Escherichia coli* GI724ΔpgiΔzwfΔpgm strain that harbors pGADP-btrC (♦) and an *Escherichia coli* GI724ΔpgiΔzwfΔpgm strain that harbors one species of pGADP-mbtrC (, which was later identified to be pGADP-btrC (W293R)) (■).

Third-stage selection was performed on the candidate clones obtained by the second-stage selection. Plasmid vectors were purified and isolated from the clones obtained by the second-stage selection, and competent cells of Escherichia coli GI724ΔpgiΔzwfΔpgm strain (the strain obtained by disrupting the pgi gene, the zwf gene, and the pgm gene in Escherichia coli GI724 strain, described in WO 2006/109479 and Kakinuma et al., Tetrahedron Letters, vol. 41 (2000), p. 1935), which is a strain highly accumulating glucose 6-phosphate (a substrate of DOI synthase), were transformed with the plasmid vectors. The transformed cells were cultured on an L agar culture medium (1% tryptone, 0.5% yeast extract, 0.5% NaCl, 2% agar, 100 µg/mL ampicillin), and grown clones were used for third-stage selection. In the third-stage selection, first, the obtained clones from which selection was to be made were inoculated into test tubes each containing 3 mL of RMM liquid culture medium (2% casamino acids, 0.5% mannitol, 0.6% $Na_2HPO_4$, 0.3% $KH_2PO_4$, 0.05% NaCl, 0.1% $NH_4Cl$, 1 mM $MgCl_2$, 100 µg/mL ampicillin), and pre-cultured while shaking at 30° C. for 24 hours. Next, each of the pre-culture liquids was inoculated into a 500 mL baffled Erlenmeyer flask each containing 50 mL of 2×YT liquid culture medium (1.6% tryptone, 1% yeast extract, 0.5% NaCl, 2% glucose, 2% mannitol, 100 µg/mL ampicillin) for third-stage selection such that the turbidity OD600 became 0.1, and main-cultured while shaking at 30° C. for 36 hours. Culture liquids obtained at 0, 12, 24, and 36 hours after the start of the main culture were centrifuged to remove the bacterial cells, and the same operation as the DOI concentration measurement operation in the first-stage selection was performed on 10 µL of each supernatant to determine the DOI concentration using HPLC. A candidate clone that exhibited a greater DOI production amount than that of a clone having the wild type DOI synthase gene of the amino acid sequence of SEQ ID NO: 1 was selected (FIG. 6). In FIG. 6, the data series represented by ♦ indicates the amount of DOI produced by the clone having the wild type DOI synthase gene of the amino acid sequence of SEQ ID NO: 1, and the data series represented by ■ indicates the amount of DOI produced by the candidate clone that exhibited a greater DOI production amount than that of the clone having the wild type DOI synthase gene.

Example 3

<Analysis of Base Sequence of Mutant DOI Synthase Gene>

In order to determine the mutation point of the DOI synthase gene, analysis of the base sequence of the DOI synthase gene of the clone obtained by the third-stage selection was performed. PCR reaction was performed using four primers of primer 7 of SEQ ID NO: 8 (5'-ggagc-caaccgaagaacc-3'), primer 8 of SEQ ID NO: 9 (5'-ctagtctagagtcgttttctgct-3'), primer 9 of SEQ ID NO: 10 (5'-acctgatgcccgaacatg-3') and primer 10 of SEQ ID NO: 11 (5'-agatcgaatccgggtccg-3') as primers for analysis, and using DTCS Quick Start Kit manufactured by Beckman Coulter Inc. The resultant reaction sample was analyzed using a CEQ 8000 Genetic Analyzer manufactured by Beckman Coulter Inc. As a result of the analysis, it was found that a base substitution occurred to substitute T that is 877th residue from the start codon of the DOI synthase gene (btrC) with A. That is, amino acid substitution occurred to substitute tryptophan that is the 293rd residue from the N-terminal with arginine. Thus, a gene (btrC (W293R)) encoding a mutant DOI synthase that improves the efficiency of DOI production as compared to a wild type DOI synthase of the amino acid sequence of SEQ ID NO: 1 was obtained.

Example 4

<Production and Purification of Wild Type DOI Synthase and Mutant DOI Synthase>

The nucleotide sequence of btrC gene was amplified by PCR using plasmid vector pLEX-btrC (described in WO 2006/109479), which harbors a wild type DOI synthase of the amino acid sequence of SEQ ID NO: 1, as a template, and using primer 11 of SEQ ID NO: 12 (5'-cgcggatc-catgacgactaaacaaattt-3'), which corresponds to a nucleotide sequence obtained by adding a BamHI restriction site to a position upstream of the start codon of the btrC gene, and primer 12 of SEQ ID NO: 13 (5'-cccaagctttacagcccttcccc-gatc-3'), which corresponds to a nucleotide sequence obtained by adding a HindIII restriction site to a position upstream of the stop codon of the btrC gene. The amplified product was ligated to pQE80L (QIAGEN), which is a vector for high expression of a recombinant protein in *Escherichia coli*, and *Escherichia coli* DH5α was transformed with the ligation product, to obtain plasmid pQE80L-btrC. Ligation to pQE80L vector enables production of a recombinant DOI synthase in which a histidine tag sequence and a DOI synthase are fused. The *Escherichia coli* that highly expressed the DOI synthase as a recombinant protein was collected by centrifugation, and then suspended in Lysis Buffer (500 mM Phosphate Buffer (pH 7.7), 300 mM NaCl, 0.2 mM $CoCl_2.6H_2O$). The suspension liquid was processed with an ultrasonic crusher to crush the *Escherichia coli*, and then centrifuged to recover the recombinant DOI synthase in the supernatant. The supernatant and Ni-NTA agarose, which specifically binds to the histidine tag sequence, were mixed to allow the DOI synthase to bind to the Ni-NTA agarose, and, thereafter, a Wash Buffer (500 mM phosphate buffer (pH 7.7), 30 mM imidazole, 0.2 mM $CoCl_2.6H_2O$) was added for washing, followed by centrifugation and discarding of the supernatant. An elution buffer (50 mM phosphate buffer (pH 7.7), 200 mM imidazole, 0.2 mM $CoCl_2.6H_2O$) was added to the Ni-NTA agarose having the recombinant DOI synthase bound thereto, thereby causing elution of the recombinant DOI synthase. As a result, the recombinant DOI synthase was purified to high purity.

Similarly, also for the mutant DOI synthase (btrC (W293R)), the nucleotide sequence of the btrC (W293R) gene was amplified by PCR using the above-obtained plasmid vector harboring the mutant DOI synthase (btrC (W293R)) as a template, and using primer 11 of SEQ ID NO: 12 (5'-cgcggatccatgacgactaaacaaattt-3'), which corresponds to a nucleotide sequence obtained by adding a BamHI restriction site to a position upstream of the start codon of the btrC gene, and primer 12 of SEQ ID NO: 13 (5'-cccaagctttacagcccttcccgatc-3'), which corresponds to a nucleotide sequence obtained by adding a HindIII restriction site to a position upstream of stop codon of btrC. The amplified product was ligated to pQE80L (QIAGEN), which is a vector for high expression of a recombinant protein in *Escherichia coli*, and *Escherichia coli* DH5α was transformed with the ligation product, and plasmid pQE80L-btrC (W293R) was obtained. The recombinant mutant DOI synthase was produced and purified in the same manner as above.

Example 5

<Measurement of Activity of Wild Type DOI Synthase and Mutant DOI Synthase>

Figure 7:
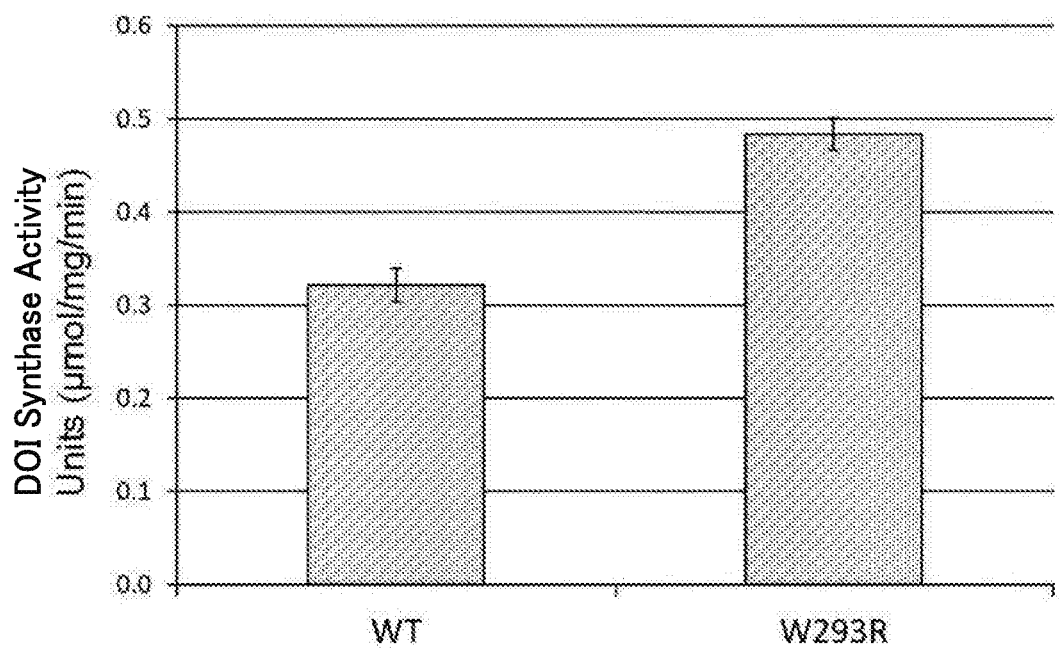
FIG. 7 shows the DOI synthase activity of the wild type DOI synthase (WT) (left) and the DOI synthase activity of the mutant DOI synthase (W293R) (right).

The enzymatic activity of the wild type DOI synthase and the mutant DOI synthase purified in Example 4 was measured using glucose 6-phosphate and $NAD^+$. The composition of the reaction solution for the assay included 50 mM Phosphate Buffer (pH 7.7), 5 mM glucose 6-phosphate, 5 mM β-$NAD^+$, 0.2 mM $CoCl_2.6H_2O$, and 10 µg of the wild type or mutant DOI synthase, and the reaction was allowed to proceed at 46° C. for 5 minutes. After the reaction, the reaction solution was subjected to phenol/chloroform treatment for deproteinization, and subjected to centrifugation. Thereafter, the amount of DOI was measured according to the method involving HPLC used for the measurement of DOI concentration in the first-stage selection in Example 2, using 10 µL of the aqueous layer fraction after centrifugation as a sample. Activity was calculated therefrom, and the amount of DOI synthesized by 1 mg of DOI synthase per minute was taken as specific activity. The DOI synthase activity of the mutant DOI synthase (W293R) was 1.5 times higher than the activity of the wild type DOI synthase of the amino acid sequence of SEQ ID NO: 1 (FIG. 7).

Example 6

Figure 8:
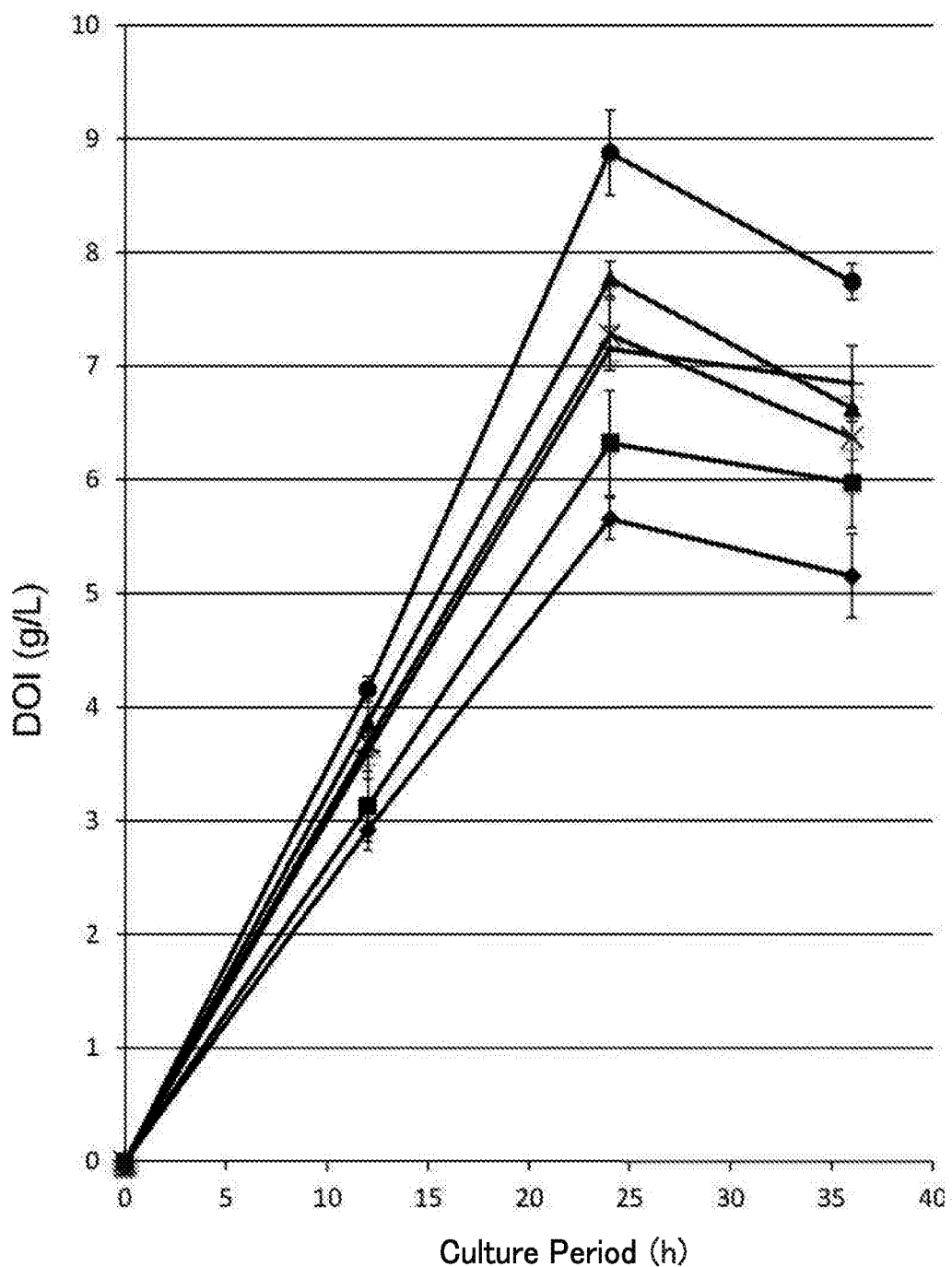
FIG. 8 shows a time course of DOI production amount in the culture medium during cultivation (2×YT+2% glucose+2% mannitol, 50 mL, 30° C.) of an *Escherichia coli* GI724ΔpgiΔzwfΔpgm strain that harbors pGADP-btrC (♦), an *Escherichia coli* GI724ΔpgiΔzwfΔpgm strain that harbors pGADP-btrC (W293R) (■), an *Escherichia coli* GI724ΔpgiΔzwfΔpgm strain that harbors pGADP-mbtrC (, which was later identified to be pGADP-btrC (W293R/N14T)) (▲), an *Escherichia coli* GI724ΔpgiΔzwfΔpgm strain that harbors pGADP-mbtrC (, which was later identified to be pGADP-btrC (W293R/Y37F)) (x), an *Escherichia coli* GI724ΔpgiΔzwfΔpgm strain that harbors pGADP-mbtrC (, which was later identified to be pGADP-btrC (W293R/A290T)) (+), and an *Escherichia coli* GI724ΔpgiΔzwfΔpgm strain that harbors pGADP-mbtrC (, which was later identified to be pGADP-btrC (W293R/H319R)) (●).

In order to obtain a mutant DOI synthase gene that further improves the efficiency of DOI production, a new mutant DOI synthase gene clone library was constructed by the error prone PCR method described in Example 1, using the plasmid containing the mutant DOI synthase gene (W293R) as a template. Subsequently, the first-stage, second-stage, and third-stage selections explained in the isolation of the mutant DOI synthase gene clone of Example 2 were carried out, and clones that exhibited a further improved efficiency of DOI production compared to the clone containing the mutant DOI synthase gene (W293R) were obtained (FIG. 8). In FIG. 8, the data series represented by ♦ represents the amount of DOI produced by *Escherichia coli* GI724ΔpgiΔzwfΔpgm strain that contained pGADP-btrC, the data series represented by ■ represents the amount of DOI produced by *Escherichia coli* GI724ΔpgiΔzwfΔpgm strain that contained pGADP-btrC(W293R), and the data series represented by ▲, the data series represented by x, the data series represented by +, and the data series represented by ● represent the amounts of DOI produced by *Escherichia coli* GI724ΔpgiΔzwfΔpgm strains that contained respectively different mutant DOI synthase genes.

Next, analysis of the base sequences was performed in the same manner as the analysis of the base sequence of the mutant DOI synthase gene of Example 3. As a result, as shown in Table 4, the following four mutant DOI synthase genes were obtained.

A mutant DOI synthase gene (btrC(W293R/N14T)) includes: a base substitution of T that is the 877th residue from the start codon of the DOI synthase gene (btrC) with A, which leads to an amino acid substitution of tryptophan that is the 293rd residue from the N-terminal of SEQ ID NO: 1 with arginine; and a base substitution of A that is the 41st residue from the start codon of the DOI synthase gene (btrC) with C, which leads to an amino acid substitution of asparagine that is the 14th residue from the N-terminal of SEQ ID NO: 1 with threonine.

A mutant DOI synthase gene (btrC (W293R/Y37F)) includes: a base substitution of T that is the 877th residue from the start codon of the DOI synthase gene (btrC) with A, which leads to an amino acid substitution of tryptophan that is the 293rd residue from the N-terminal of SEQ ID NO: 1 with arginine; and a base substitution of A that is the 110th residue from the start codon of the DOI synthase gene (btrC) with T, which leads to an amino acid substitution of tyrosine that is the 37th residue from the N-terminal of SEQ ID NO: 1 with phenylalanine.

A mutant DOI synthase gene (btrC (W293R/A290T)) includes: a base substitution of T that is the 877th residue from the start codon of the DOI synthase gene (btrC) with A, which leads to an amino acid substitution of tryptophan that is the 293rd residue from the N-terminal of SEQ ID NO: 1 with arginine; and a base substitution of G that is the 868th residue from the start codon of the DOI synthase gene (btrC) with A, which leads to an amino acid substitution of alanine that is the 290th residue from the N-terminal of SEQ ID NO: 1 with threonine.

A mutant DOI synthase gene (btrC (W293R/H319R)) includes: a base substitution of T that is the 877th residue from the start codon of the DOI synthase gene (btrC) with A, which leads to an amino acid substitution of tryptophan that is the 293rd residue from the N-terminal of SEQ ID NO: 1 with arginine; and a base substitution of A that is the 956th residue from the start codon of the DOI synthase gene (btrC) with G, which leads to an amino acid substitution of histidine that is the 319th residue from the N-terminal of SEQ ID NO: 1 with arginine.

TABLE 4

Mutation Positions in Mutant DOI Synthase Genes

| Name of Mutant DOI Synthase Gene | Mutation Positions [Base (amino acid)] |
| --- | --- |
| btrC (W293R/N14T) | T877A (W293R)/A41C (N14T) |
| btrC (W293R/Y37F) | T877A (W293R)/A110T (Y37F) |
| btrC (W293R/A290T) | T877A (W293R)/G868A (A290T) |
| btrC (W293R/H319R) | T877A (W293R)/A956G (H319R) |

The numerical values of the DOI production (shown in FIG. 8) by the clone containing the wild type DOI synthase gene, the clone containing the mutant DOI synthase gene having the W293R mutation, and the clones indicated in Table 4 are shown in Table 5 below.

TABLE 5

| DOI Synthase Gene | Culture Period | | |
| --- | --- | --- | --- |
| | 12 h | 24 h | 36 h |
| WT | 2.92 (±0.18) | 5.66 (±0.18) | 5.16 (±0.37) |
| W293R | 3.13 (±0.31) | 6.32 (±0.46) | 5.97 (±0.39) |
| W293R/N14T | 3.87 (±0.30) | 7.77 (±0.15) | 6.63 (±0.01) |
| W293R/Y37F | 3.69 (±0.05) | 7.28 (±0.31) | 6.37 (±0.20) |
| W293R/A290T | 3.61 (±0.24) | 7.15 (±0.19) | 6.85 (±0.33) |
| W293R/H319R | 4.16 (±0.11) | 8.88 (±0.37) | 7.74 (±0.16) |

The numbers in the table indicate the DOI concentrations (g/L) in the culture medium. Each DOI concentration indicated is an average value of three measurements, and the number in the parentheses indicate standard deviation.

Figure 9:
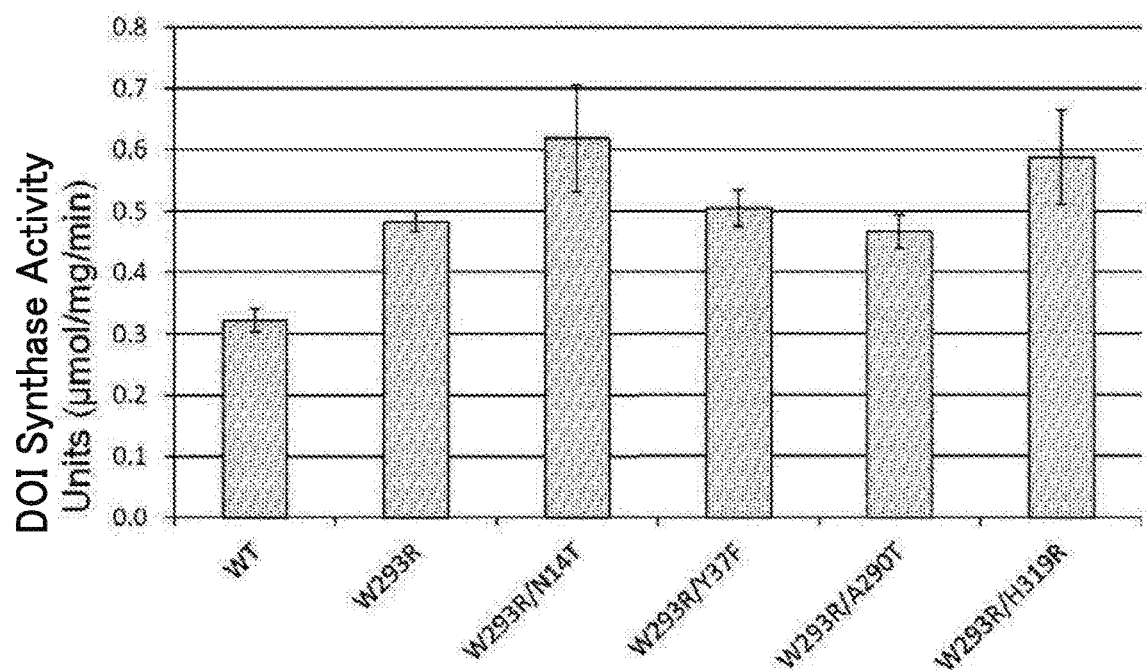
FIG. 9 shows the DOI synthase activity of a wild type DOI synthase (WT), a mutant DOI synthase (W293R), a mutant DOI synthase (W293R/N14T), a mutant DOI synthase (W293R/Y37F), a mutant DOI synthesis (W293R/A290T) and a mutant DOI synthase (W293R/H319R), in the order from left to right.

Next, the four types of mutant DOI synthase (btrC (W293R/N14T)), (btrC (W293R/Y37F)), (btrC (W293R/A290T)), and (btrC (W293R/H319R)) were produced and purified in the same manner as that in Example 4. Thereafter, the wild type DOI synthase and each mutant DOI synthase were assayed in the same manner as that in Example 5, and the activities were compared. As a result, it was found that:

The DOI synthase activity of the mutant DOI synthase (W293R/N14T) was 1.92 times higher than the activity of the wild type DOI synthase of the amino acid sequence of SEQ ID NO: 1 (FIG. 9);

the DOI synthase activity of the mutant DOI synthase (W293R/Y37F) was 1.57 times higher than the activity of the wild type DOI synthase of the amino acid sequence of SEQ ID NO: 1 (FIG. 9);

the DOI synthase activity of the mutant DOI synthase (W293R/A290T) was 1.45 times higher than the activity of the wild type DOI synthase of the amino acid sequence of SEQ ID NO: 1 (FIG. 9); and the DOI synthase activity of the mutant DOI synthase (W293R/H319R) was 1.83 times higher than the activity of the wild type DOI synthase of the amino acid sequence of SEQ ID NO: 1 (FIG. 9).

All of the four mutant DOI synthase genes exhibited higher activity than that of the wild type DOI synthase of the amino acid sequence of SEQ ID NO: 1.

Example 7

<Efficiency of DOI Production by Fermentation of Transformant to which Mutant DOI Synthase Gene (btrC (W293R/H319R)) has been Introduced>

An expression vector for expressing a DNA fragment of a mutant DOI synthase gene (btrC (W293R/H319R)) in a host cell (*Escherichia coli*) was constructed. Specifically, PCR amplification was performed using pLEX vector (Invitrogen) as a template, and using primer 3 of SEQ ID NO: 4 (5'-atggtaccgagctcggatcc-3') and primer 13 of SEQ ID NO: 14 (5'-cgcggatccgagataatttatcaccgcag-3') having a BamHI restriction site at a 5'-side position. For the PCR amplification, KOD polymerase (TOYOBO) was used. The reaction conditions for PCR included holding the temperature at 94° C. for 2 minutes, performing 30 cycles, and holding the temperature at 68° C. for 2 minutes, each cycle including performing heat denaturation at 94° C. for 30 seconds, performing annealing at 50° C. for 30 seconds, and performing DNA extension reaction at 68° C. for 1 minute. The PCR amplification product obtained was retained at 4° C. The DNA fragment amplified by the PCR amplification was treated with phenol/chloroform, and then centrifuged. The supernatant was subjected to ethanol precipitation, and the DNA fragment was recovered. The recovered DNA fragment was digested with restriction enzymes BamHI and PstI, and purified and isolated by agarose gel electrophoresis, to obtain a DNA fragment of the expression vector.

Next, gapA promoter was obtained as a promoter for expressing the DNA fragment of the mutant DOI synthase gene (btrC (W293R/H319R)) in a host cell (*Escherichia coli*). Specifically, gapA promoter was obtained as follows. PCR amplification was performed using the chromosomal DNA of *Escherichia coli* as a template, and using primer 14 of SEQ ID NO: 15 (5'-cgcggatccgcgggaagagtgaggcgagtc-3') having a BamHI restriction site at a 5'-side position and primer 15 of SEQ ID NO: 16 (5'-atattccaccacctatttg-3') to which a phosphate group has been added at the 5'-side thereof. For the PCR amplification, KOD polymerase (TOYOBO) was used. The reaction conditions for PCR included holding the temperature at 94° C. for 2 minutes, performing 30 cycles, and holding the temperature at 68° C. for 2 minutes, each cycle including performing heat denaturation at 94° C. for 30 seconds, performing annealing at 50° C. for 30 seconds, and performing DNA extension reaction at 68° C. for 1 minute. The PCR amplification product obtained was retained at 4° C. The DNA fragment amplified by the PCR amplification was treated with phenol/chloroform, and then centrifuged. The supernatant was subjected to ethanol precipitation, and the DNA fragment of the gapA promoter was recovered.

Then, PCR amplification was performed using a plasmid containing a mutant DOI synthase gene (btrC (W293R/H319R)) as a template, and using a primer 16 of SEQ ID NO: 17 (5'-atgacgactaaacaaatttgttttgcgg-3') having a phosphate group added at its 5'-side thereof and primer 17 of SEQ ID NO: 18 (5'-aaaactgcagttacagccctcccggatc-3') having a PstI restriction site at a 5'-side position. For the PCR amplification, KOD polymerase (TOYOBO) was used. The reaction conditions for PCR included holding the temperature at 94° C. for 2 minutes, performing 30 cycles, and holding the temperature at 68° C. for 2 minutes, each cycle including performing heat denaturation at 94° C. for 30 seconds, performing annealing at 50° C. for 30 seconds, and performing DNA extension reaction at 68° C. for 1 minute. The PCR amplification product obtained was retained at 4° C. The DNA fragment amplified by the PCR amplification was treated with phenol/chloroform, and centrifuged. The supernatant was subjected to ethanol precipitation, and the DNA fragment of the mutant DOI synthase gene (btrC (W293R/H319R)) was recovered.

Figure 10:
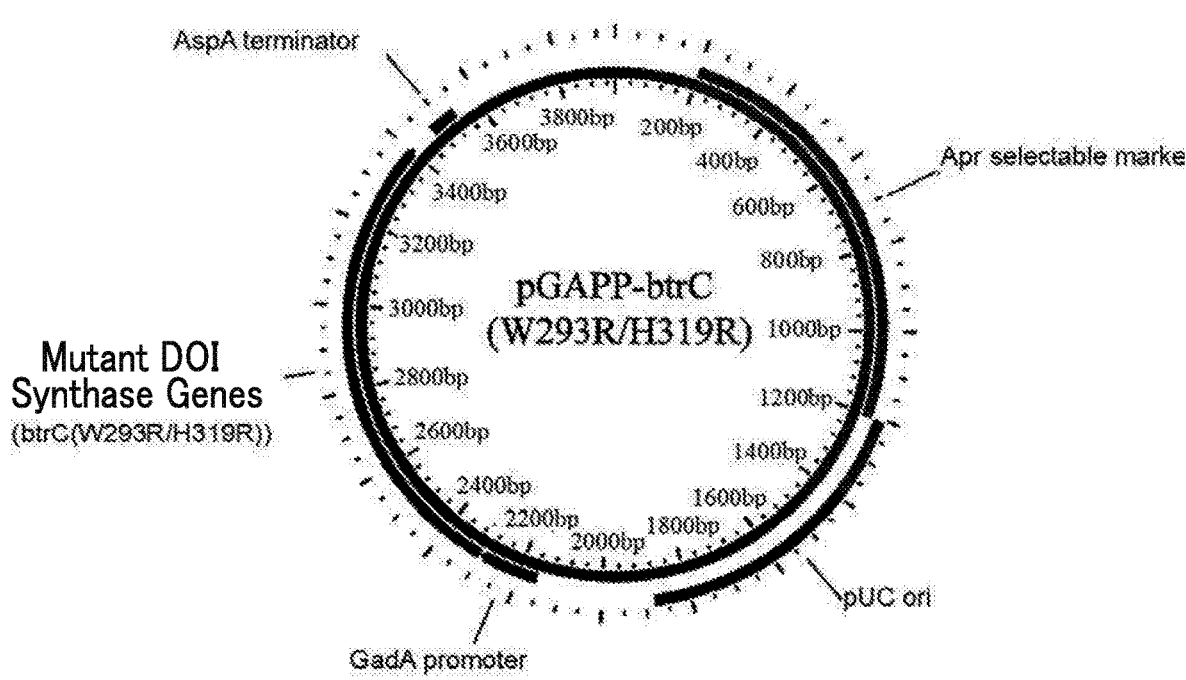
FIG. 10 illustrates the structure of pGAPP-btrC (W293R/H319R).
Figure 11:
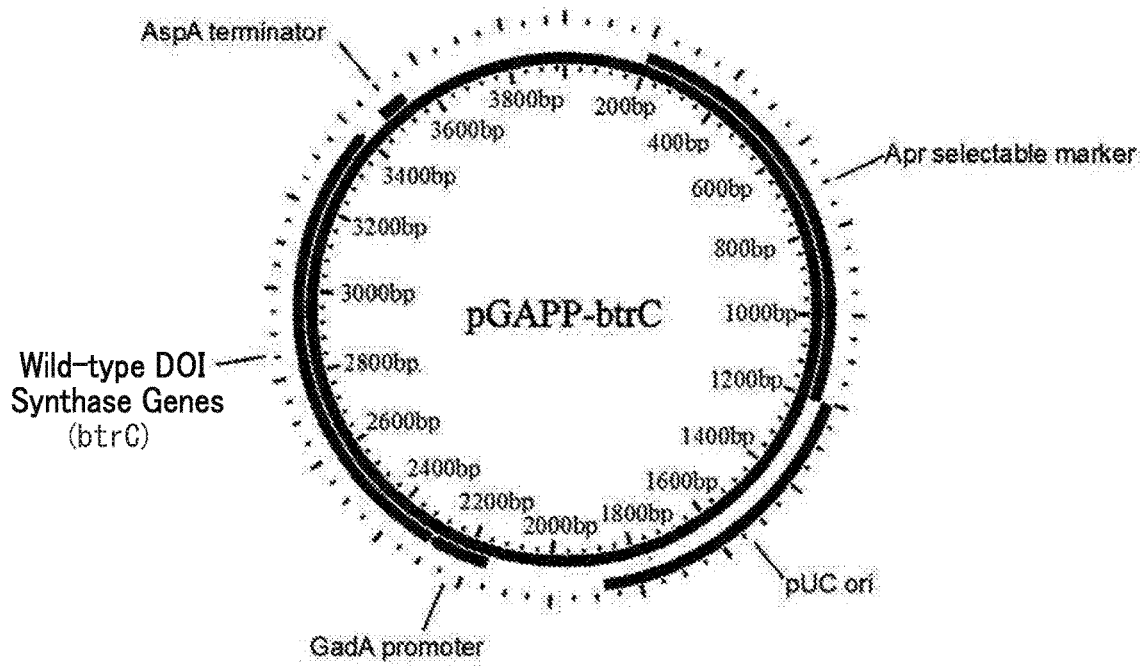
FIG. 11 illustrates the structure of pGAPP-btrC.

Next, the DNA fragment of the gapA promoter amplified above and the DNA fragment of the mutant DOI synthase gene (btrC (W293R/H319R)) were allowed to react at 16° C. for 30 minutes using 2×Ligation Mix. PCR amplification was performed using the obtained ligation product as a template and using primer 14 of SEQ ID NO: 15 and primer 17 of SEQ ID NO: 18. For the PCR amplification, KOD polymerase (TOYOBO) was used. The reaction conditions for PCR included holding the temperature at 94° C. for 2 minutes, performing 30 cycles, and holding the temperature at 68° C. for 2 minutes, each cycle including performing heat denaturation at 94° C. for 30 seconds, performing annealing at 50° C. for 30 seconds, and performing DNA extension reaction at 68° C. for 1 minute. The PCR amplification product obtained was retained at 4° C. The DNA fragment amplified by the PCR amplification was treated with phenol/chloroform, and centrifuged. The supernatant was subjected to ethanol precipitation, and a DNA fragment was recovered. The recovered DNA fragment was digested with restriction enzymes BamHI and PstI, and purified and isolated by agarose gel electrophoresis, thereby obtaining a DNA fragment of the expression vector. This DNA fragment was inserted into the above-described DNA fragment of the expression vector by ligation, thereby obtaining a plasmid pGAPP-btrC (W293R/H319R) (FIG. 10). In addition, pGAPP-btrC into which the wild type DOI synthase gene of the amino acid sequence of SEQ ID NO: 1 was inserted was also obtained in a similar manner (FIG. 11).

Plasmid pGAPP-btrC (W293R/H319R) and plasmid pGAPP-btrC were purified and isolated, and each used for transforming competent cells of *Escherichia coli* GI724ΔpgiΔzwfΔpgm strain (described in WO 2006/109479 and Kakinuma et al., *Tetrahedron Letters*, vol. 41 (2000), p. 1935), which is a strain highly accumulating glucose 6-phosphate (a substrate of the DOI synthase). The transformed cells were inoculated into test tubes each containing 3 mL of 2×YT liquid culture medium (1.6% tryptone, 1% yeast extract, 100 μg/mL ampicillin), and pre-cultured while shaking at 30° C. for 24 hours. Next, the pre-culture liquids were inoculated into 500 mL baffled Erlenmeyer flasks each containing 50 mL of 2×YT liquid culture medium for culture for evaluation (1.6% tryptone, 1% yeast extract, 0.5% NaCl, 5% glucose, 5% mannitol, 100 μg/mL ampicillin) such that the turbidity OD 600 became 0.1, and main-cultured while shaking at 30° C. for 60 hours. Culture liquids obtained at 0, 12, 24, 36, 48, and 60 hours after the start of the main culture were centrifuged to remove the bacterial cells, and the same operation as the DOI concentration measurement operation in the first-stage selection in Example 2 was performed on 10 μL of each supernatant to determine a DOI concentration using HPLC. In addition, cell turbidity, glucose concentration, and mannitol concentration in the culture medium were also measured. Cell turbidity was measured by measuring absorbance at 600 nm using a spectrophotometer, glucose concentration was measured using Glucose CII-Test Wako manufactured by Wako Pure Chemical Industries, Ltd., and mannitol concentration was measured using Mannitol Assay Kit manufactured by Megazyme.

Figure 12A:
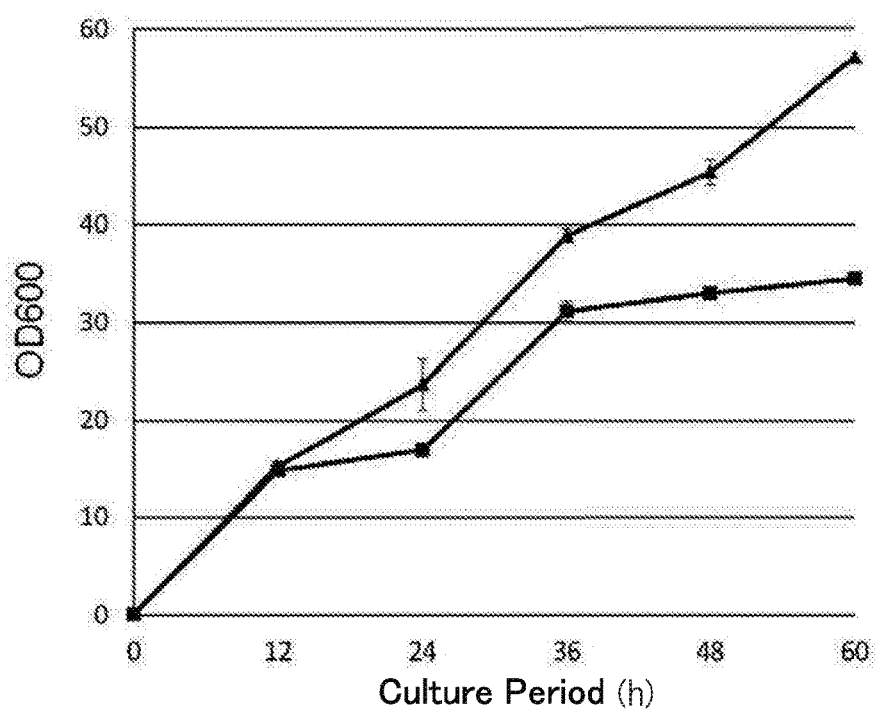
FIG. 12A shows a time course of turbidity of the culture medium during cultivation (2×YT+5% glucose+5% mannitol, 50 mL, 30° C.) of an *Escherichia coli* GI724ΔpgiΔzwfΔpgm strain that harbors pGAPP-btrC (■) and an *Escherichia coli* GI724ΔpgiΔzwfΔpgm strain that harbors pGAPP-btrC (W293R/H319R) (▲).
Figure 12B:
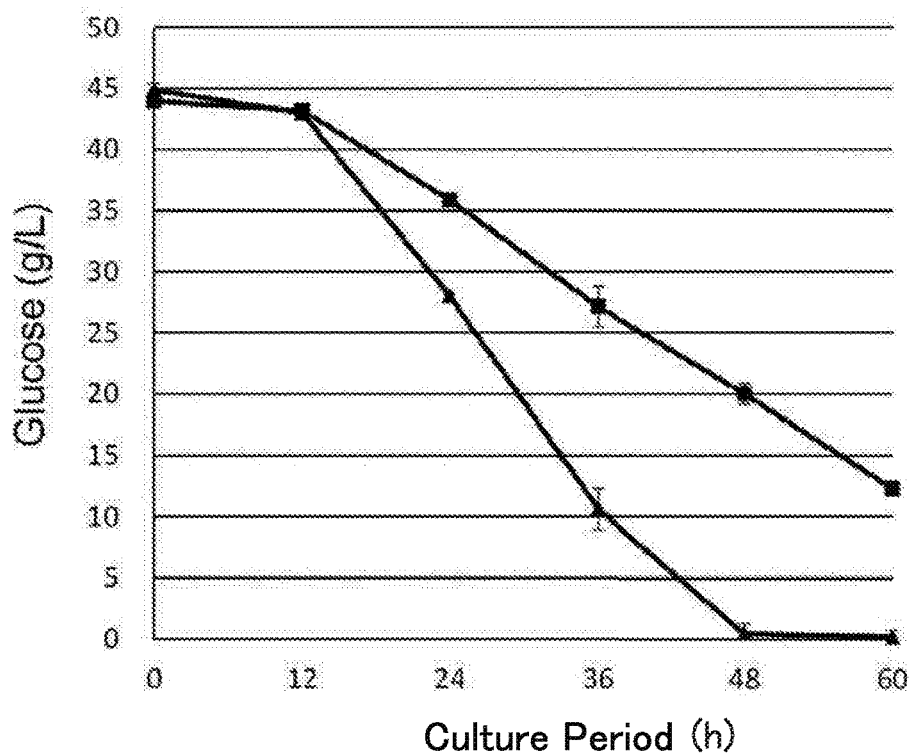
FIG. 12B shows a time course of glucose concentration in the culture medium during cultivation (2×YT+5% glucose+5% mannitol, 50 mL, 30° C.) of an *Escherichia coli* GI724ΔpgiΔzwfΔpgm strain that harbors pGAPP-btrC (■) and an *Escherichia coli* GI724ΔpgiΔzwfΔpgm strain that harbors pGAPP-btrC (W293R/H319R) (▲).
Figure 12C:
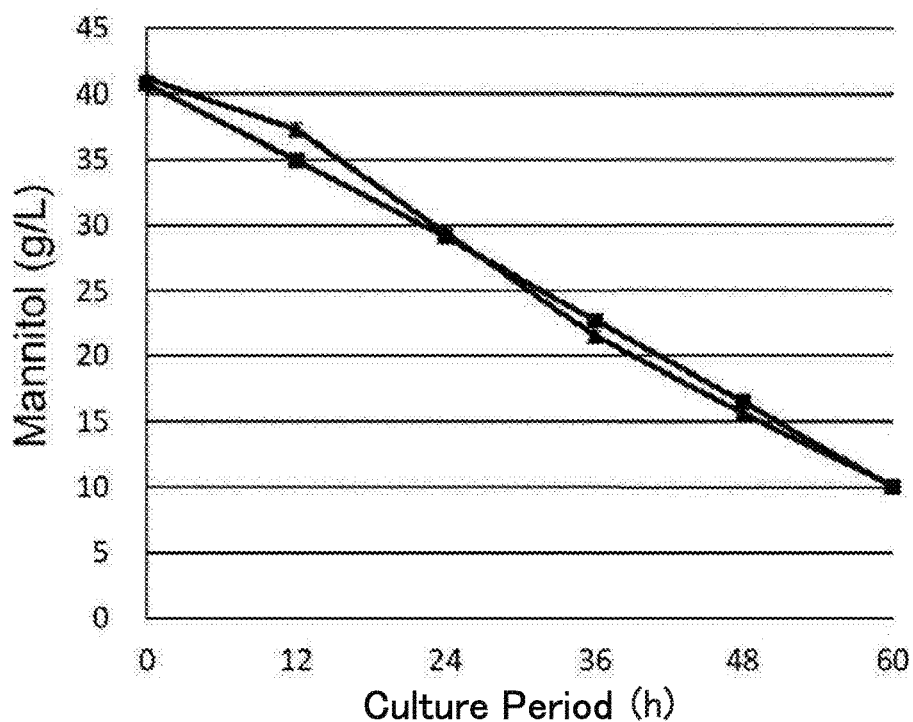
FIG. 12C shows a time course of mannitol concentration in the culture medium during cultivation (2×YT+5% glucose+5% mannitol, 50 mL, 30° C.) of an *Escherichia coli* GI724ΔpgiΔzwfΔpgm strain that harbors pGAPP-btrC (■) and an *Escherichia coli* GI724ΔpgiΔzwfΔpgm strain that harbors pGAPP-btrC (W293R/H319R) (▲).
Figure 12D:
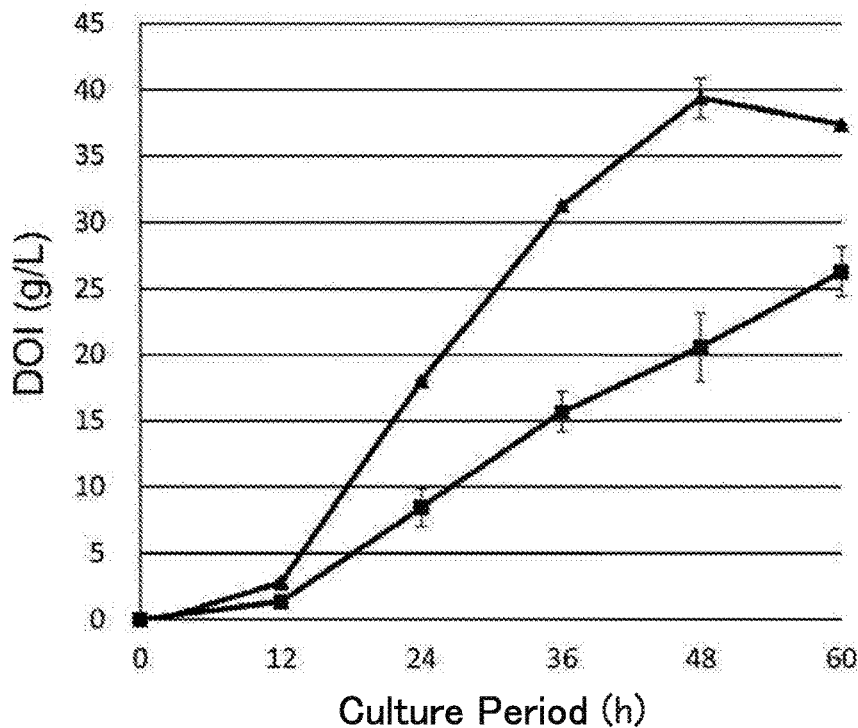
FIG. 12D shows a time course of DOI production amount during cultivation (2×YT+5% glucose+5% mannitol, 50 mL, 30° C.) of an *Escherichia coli* GI724ΔpgiΔzwfΔpgm strain that harbors pGAPP-btrC (■) and an *Escherichia coli* GI724ΔpgiΔzwfΔpgm strain that harbors pGAPP-btrC (W293R/H319R) (▲).

FIG. 12A shows the time course of turbidity of the culture medium, FIG. 12B shows the time course of glucose concentration in the culture medium, FIG. 12C shows the time course of mannitol concentration in the culture medium, and FIG. 12D shows the time course of DOI production amount. The *Escherichia coli* GI724ΔpgiΔzwfΔpgm strain that contained pGAPP-btrC (W293R/H319R) (the data series indicated by ▲ in FIGS. 12A to 12D) exhibited a DOI production speed that is about 2 times higher than that of the

*Escherichia coli* GI724ΔpgiΔzwfΔpgm strain that contained pGAPP-btrC (the data series indicated by ■ in FIGS. 12A to 12D).

Example 8

<DOI Production Amount by Fermentation of Transformant into which Mutant DOI Synthase Gene (btrC (H319R)) has been Introduced>

Figure 13:
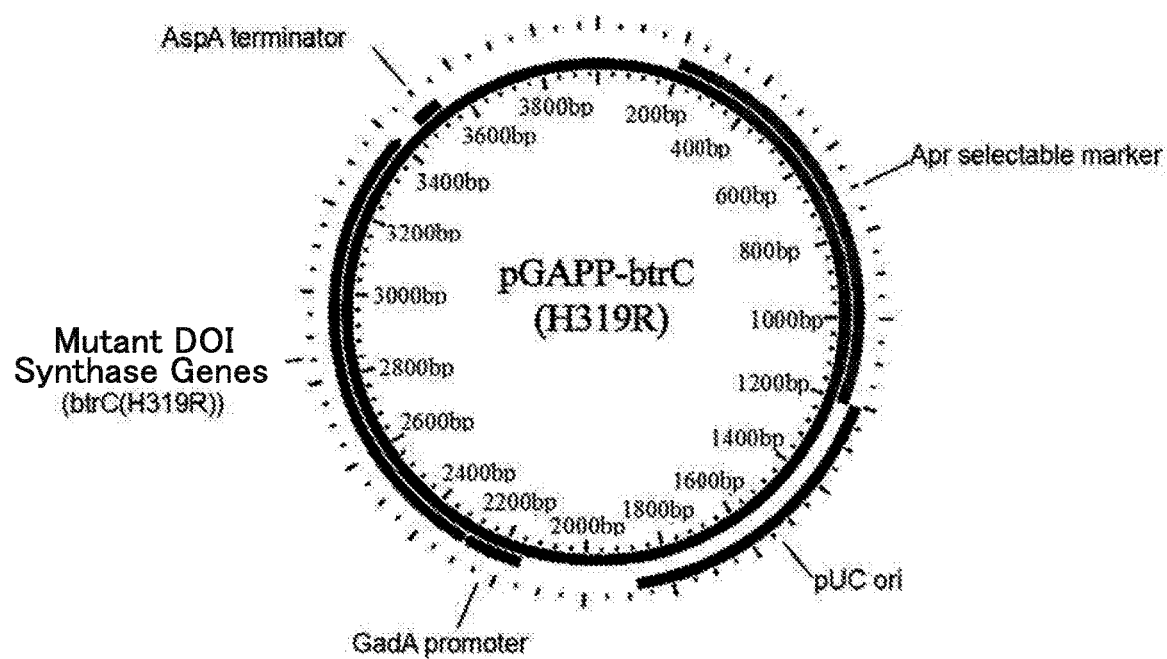
FIG. 13 illustrates the structure of pGAPP-btrC (H319R).

An expression vector for expressing a DNA fragment of a mutant DOI synthase gene (btrC (H319R)) in a host cell (*Escherichia coli*) was constructed. Specifically, PCR amplification was performed using, as a template, pGAPP-btrC to which the wild type DOI synthase gene of the amino acid sequence of SEQ ID NO: 1 was inserted (FIG. 11), and using primer 18 of SEQ ID NO: 19 (5'-ttccattatttaatccgcgataacaagagg-3') and primer 19 of SEQ ID NO: 20 (5'-cctcttgttatcgcggattaaataatggaa-3'). For the PCR amplification, KOD polymerase (TOYOBO) was used. The reaction conditions for PCR included holding for 2 minutes at 94° C., performing 20 cycles, and holding the temperature at 68° C. for 3 minutes, each cycle including performing heat denaturation at 98° C. for 15 seconds, performing annealing at 55° C. for 30 seconds, and performing DNA extension reaction at 68° C. for 6 minutes. The obtained PCR amplification product was retained at 4° C. The DNA fragment amplified by the PCR amplification was digested with a restriction enzyme DpnI, and used for transforming *Escherichia coli* DH5α, thereby obtaining plasmid pGAPP-btrC (H319R) (FIG. 13).

Plasmid pGAPP-btrC (H319R) and plasmid pGAPP-btrC were purified and isolated, and competent cells of *Escherichia coli* GI724ΔpgiΔzwfΔpgm strain (described in WO 2006/109479 and Kakinuma et al., *Tetrahedron Letters*, vol. 41(2000), p. 1935), which is a strain highly accumulating glucose 6-phosphate (a substrate of DOI synthase), were transformed with the plasmids. The transformed cells were inoculated into test tubes each containing 3 mL of 2×YT liquid culture medium (1.6% tryptone, 1% yeast extract, 100 g/mL ampicillin), and pre-cultured while shaking at 30° C. for 24 hours. Next, the pre-culture liquids were inoculated into 200 mL baffled Erlenmeyer flasks each containing 30 mL of 2×YT liquid culture medium for culture for evaluation (1.6% tryptone, 1% yeast extract, 0.5% NaCl, 3% glucose, 4% mannitol, 100 μg/mL ampicillin) such that the turbidity OD 600 became 0.1, and main-cultured while shaking at 30° C. for 48 hours. Culture liquids obtained at 0, 12, 24, 36, and 48 hours after the start of the main culture were centrifuged to remove the bacterial cells, and the same operation as the DOI concentration measurement operation in the first-stage selection in Example 2 was performed on 10 μL of each supernatant to determine the DOI concentration using HPLC. In addition, cell turbidity, glucose concentration, and mannitol concentration in the culture medium were also measured. Cell turbidity was measured by measuring absorbance at 600 nm using a spectrophotometer, glucose concentration was measured using Glucose CII-Test Wako manufactured by Wako Pure Chemical Industries, Ltd., and mannitol concentration was measured using Mannitol Assay Kit manufactured by Megazyme.

Figure 14B:
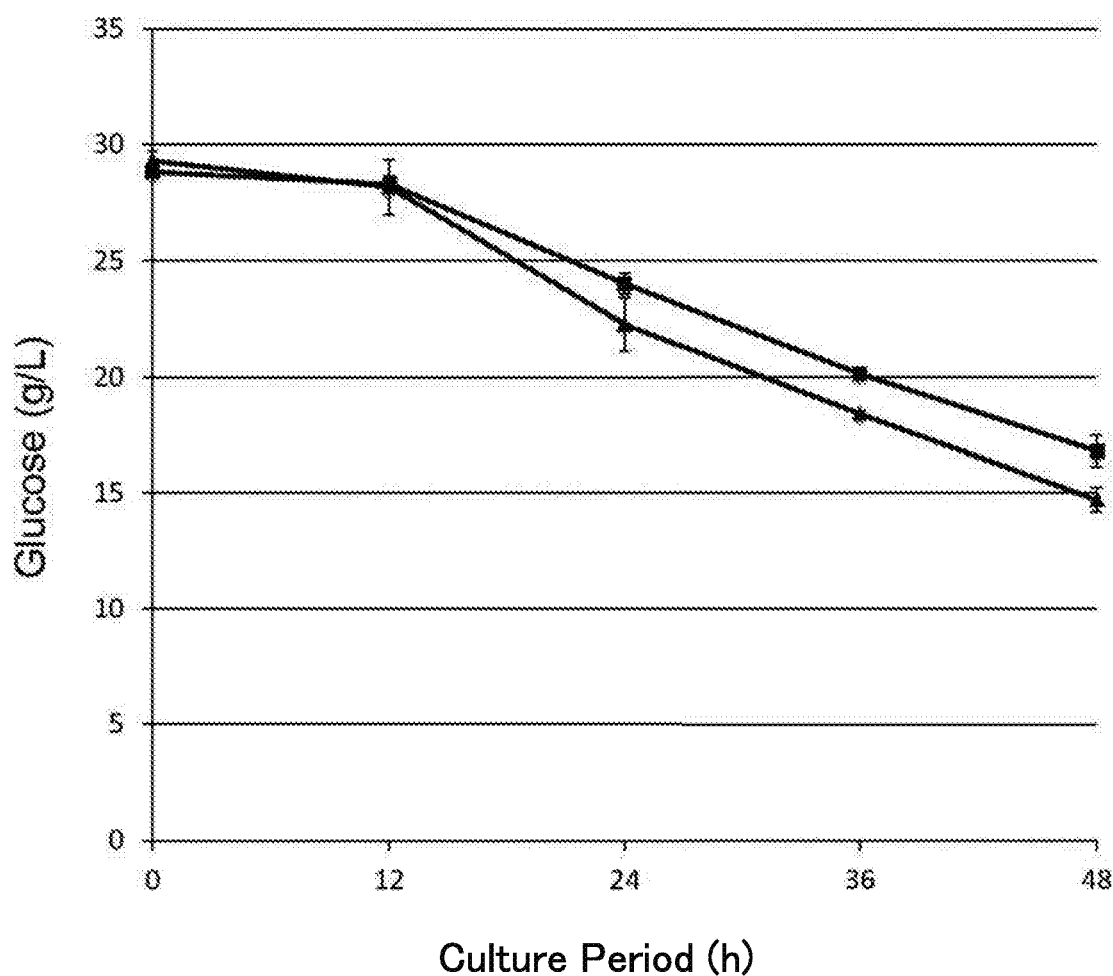
FIG. 14B shows a time course of glucose concentration of the culture medium during cultivation (2×YT+3% glucose+4% mannitol, 30 mL, 30° C.) of an *Escherichia coli* GI724ΔpgiΔzwfΔpgm strain that harbors pGAPP-btrC (■) and an *Escherichia coli* GI724ΔpgiΔzwfΔpgm strain that harbors pGAPP-btrC (H319R) (▲).
Figure 14C:
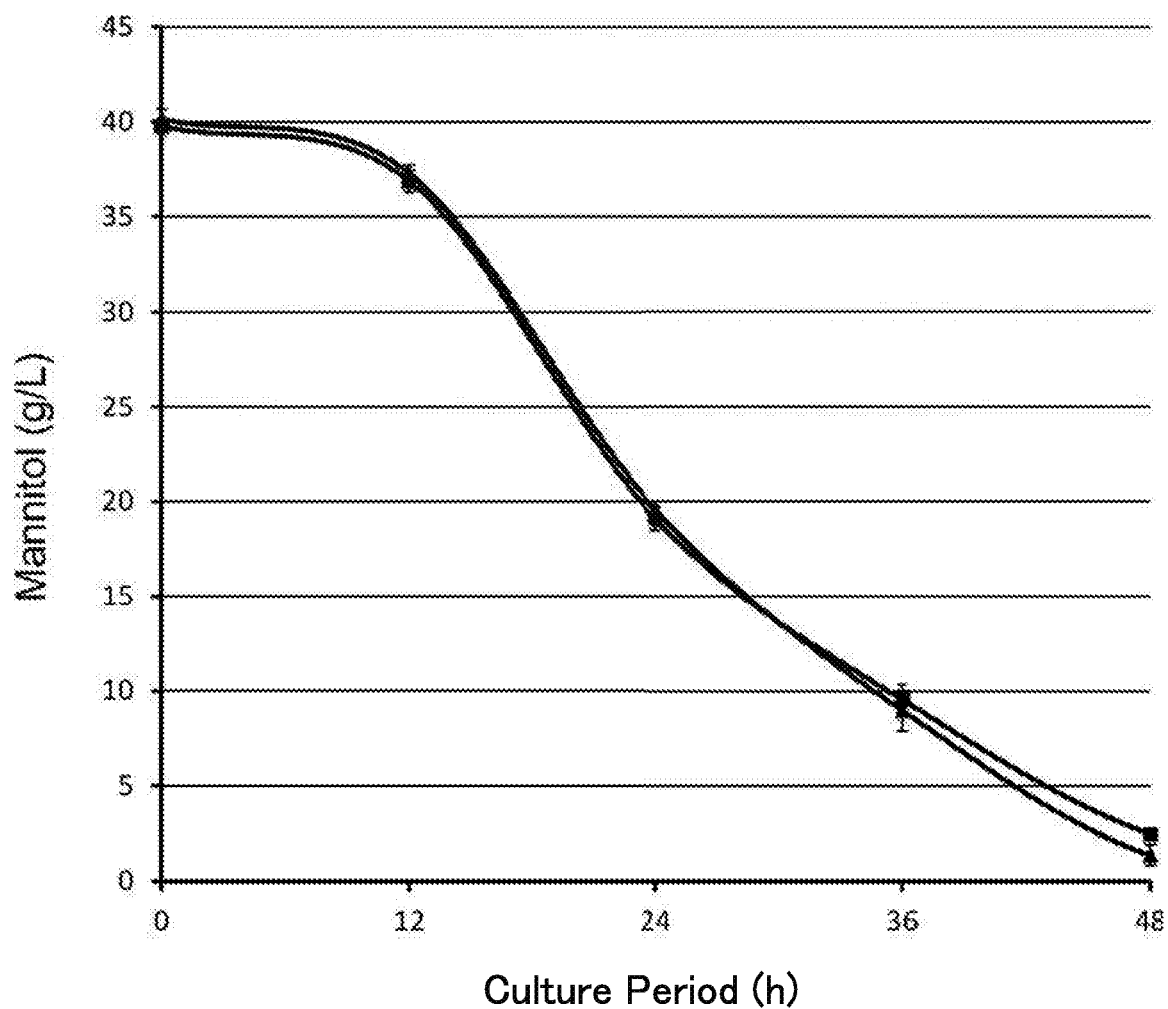
FIG. 14C shows a time course of mannitol concentration of the culture medium during cultivation (2×YT+3% glucose+4% mannitol, 30 mL, 30° C.) of an *Escherichia coli* GI724ΔpgiΔzwfΔpgm strain that harbors pGAPP-btrC (■) and an *Escherichia coli* GI724ΔpgiΔzwfΔpgm strain that harbors pGAPP-btrC (H319R) (▲).
Figure 14D:
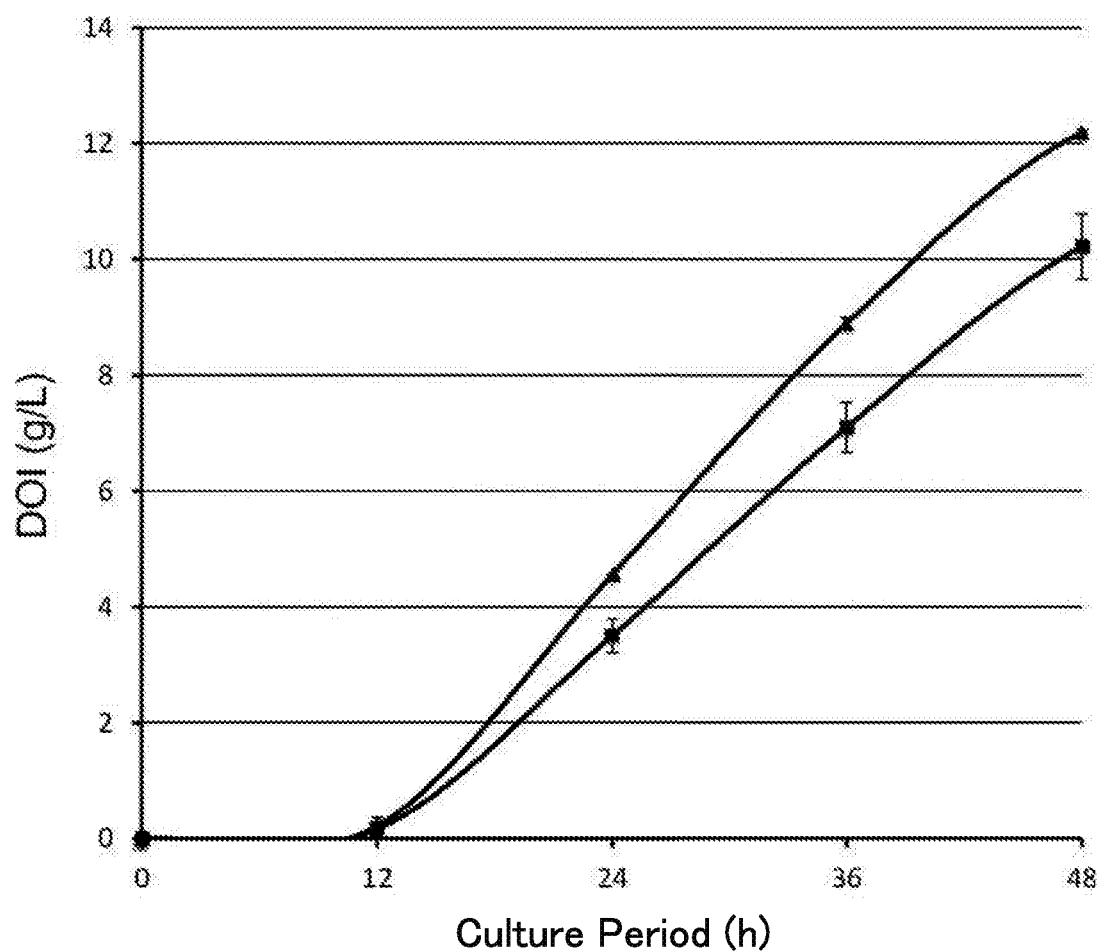
FIG. 14D shows a time course of DOI production amount during cultivation (2×YT+3% glucose+4% mannitol, 30 mL, 30° C.) of an *Escherichia coli* GI724ΔpgiΔzwfΔpgm strain that harbors pGAPP-btrC (■) and an *Escherichia coli* GI724ΔpgiΔzwfΔpgm strain that harbors pGAPP-btrC (H319R) (▲).

FIG. 14A shows the time course of turbidity of the culture medium, FIG. 14B shows the time course of glucose concentration in the culture medium, FIG. 14C shows the time course of mannitol concentration in the culture medium, and FIG. 14D shows the time course of DOI production amount. The *Escherichia coli* GI724ΔpgiΔzwfΔpgm strain that contained pGAPP-btrC (H319R) (the data series indicated by ▲ in FIGS. 14A to 14D) exhibited a DOI production speed that is about 1.2 times higher than that of the *Escherichia coli* GI724ΔpgiΔzwfΔpgm strain that contained pGAPP-btrC (the data series represented by ■ in FIGS. 14A to 14D).

Example 9

<Evaluation of Efficiency of DOI Production by Fermentation in a Jar Fermenter of Transformant to which Mutant DOI Synthase Gene (btrC (W293R/N14T)) has been Introduced and Transformant to which Mutant DOI Synthase Gene (btrC (W293R/H319R)) has been Introduced)

For cultivation in a jar fermenter, a host and an expression vector that are different from those in Example 8 were used. *Escherichia coli* MG1655ΔpgiΔzwf strain (a strain obtained by disrupting the pgi gene and the zwf gene in *Escherichia coli* MG1655 strain, described in WO 2010/053052), which is a strain highly accumulating glucose 6-phosphate (a substrate of DOI synthase), was used as the host. The expression vector was prepared as follows.

Figure 15:
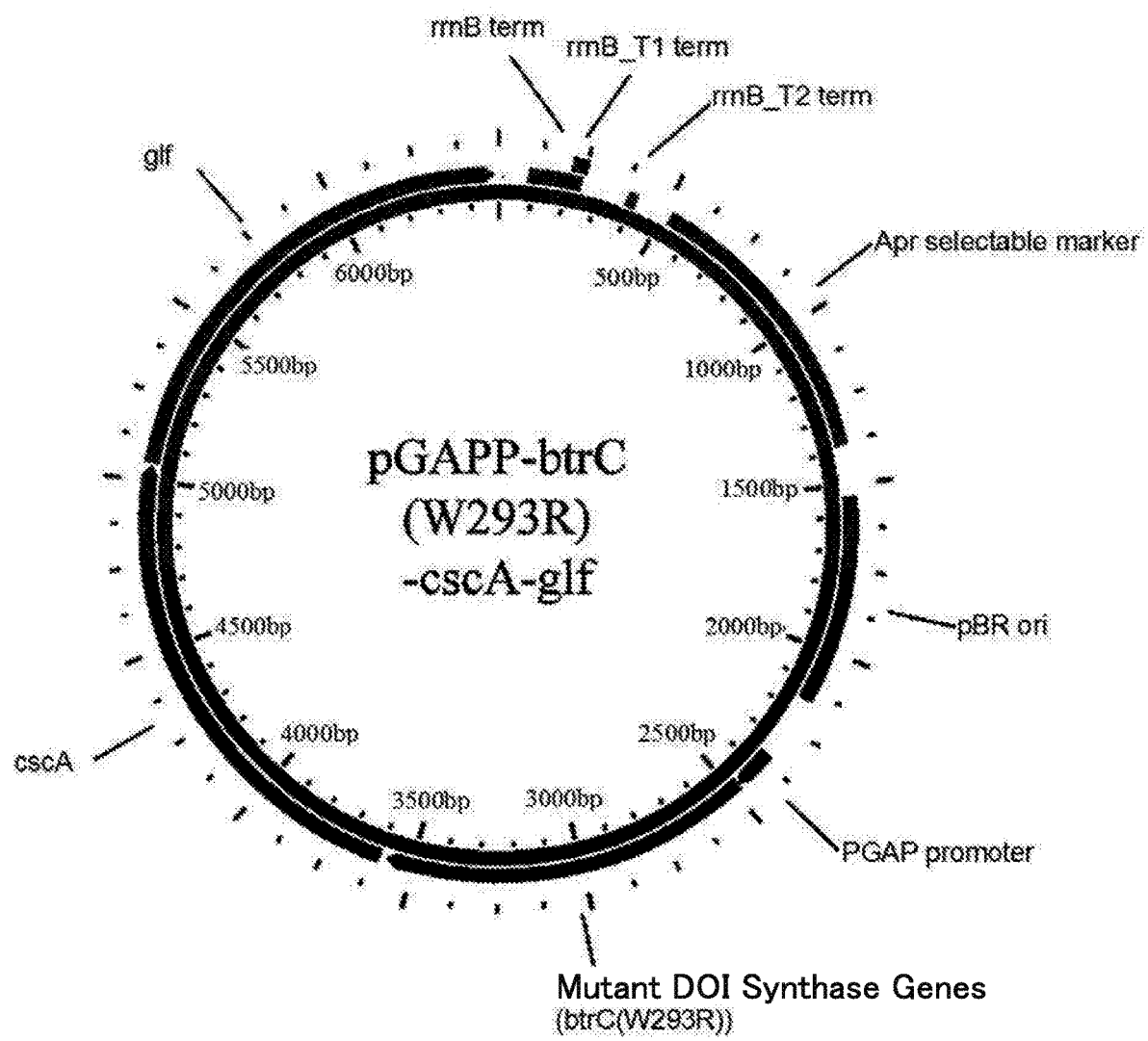
FIG. 15 illustrates the structure of pGAPP-btrC (W293R)-cscA-glf.

PCR amplification was performed using plasmid vector pGAP-btrC-cscA-glf containing a DOI synthase gene (btrC) (a plasmid vector obtained by incorporating an expression unit including GADPH promoter, btrC, which is a DOI synthase gene from *Bacillus circulance*, cscA, which is a sucrose hydrolase gene from *Escherichia coli* O-157, and glf, which is a glucose transport promoting protein gene from *Zymomonas mobilis*, into pBR322 (Genbank accession No. J01749), described in WO 2010/053052) as a template, and using primer 20 of SEQ ID NO: 21 (5'-cattacaggcttttaaataaaatcggg-3') and primer 21 of SEQ ID NO: 22 (5'-taaaagcctgtaatgggcggacacgtc-3'). For the PCR amplification, PRIMESTAR Max DNA Polymerase (TAKARA) was used. The reaction conditions for PCR included 30 cycles each including performing heat denaturation at 98° C. for 10 seconds, performing annealing at 55° C. for 15 seconds, and performing DNA extension reaction at 72° C. for 40 seconds. *Escherichia coli* DH5α was transformed with the PCR product thus amplified, to obtain plasmid vector pGAPP-btrC (W293R)-cscA-glf (FIG. 15), which contained the mutant DOI synthase gene (btrC (W293R)).

Figure 16:
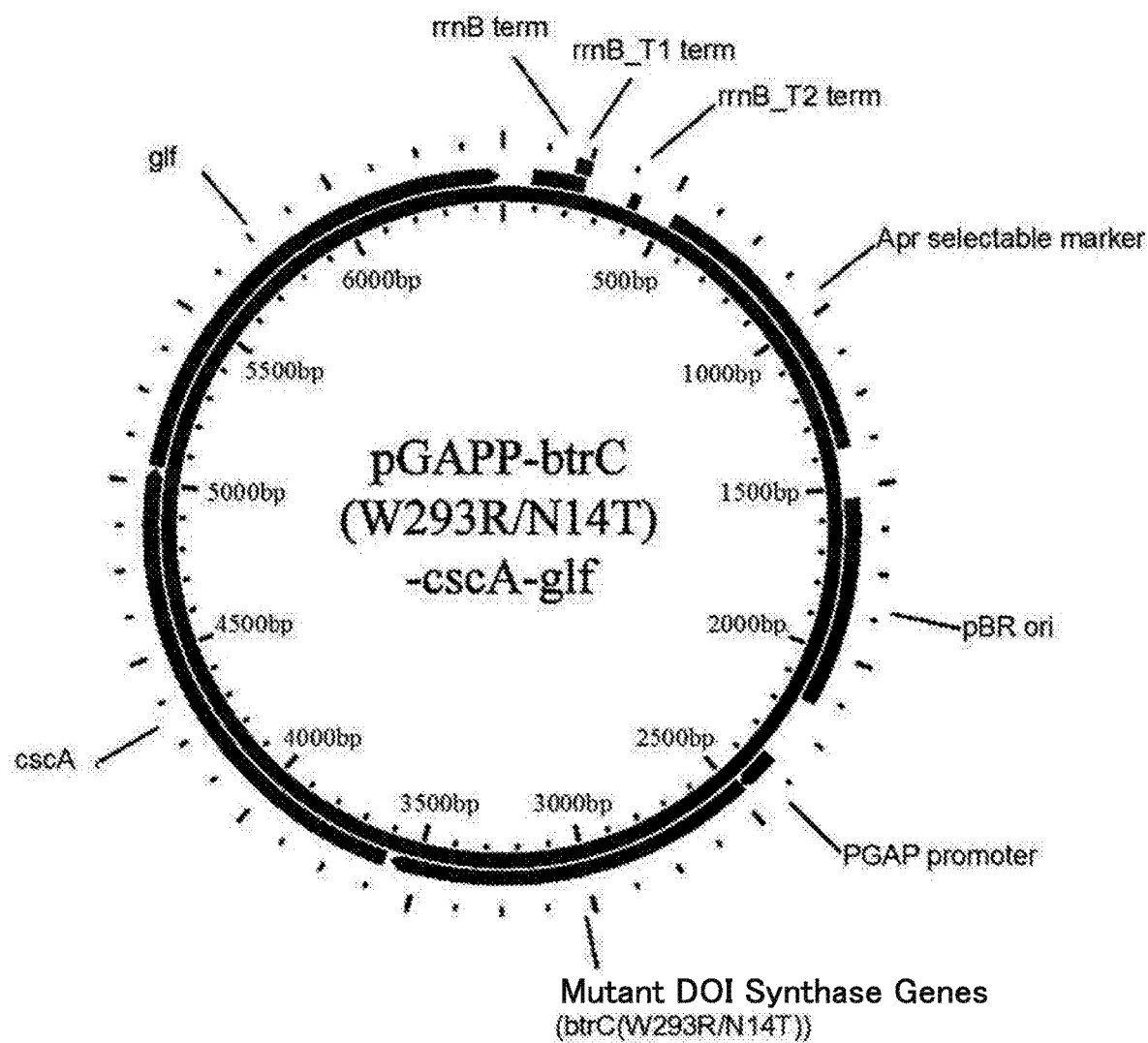
FIG. 16 illustrates the structure of pGAPP-btrC (W293R/N14T)-cscA-glf.

PCR amplification was performed using plasmid vector pGAPP-btrC (W293R)-cscA-glf containing a mutant DOI synthase gene (btrC (W293R)) as a template, and using primer 22 of SEQ ID NO: 23 (5'-tgttttacctttgcattcggcgaacat-3') and primer 23 of SEQ ID NO: 24 (5'-tgcaaaggtaaaacaccggtccgcaaa-3'). For the PCR amplification, PRIMESTAR Max DNA Polymerase (TAKARA) was used. The reaction conditions for PCR included 30 cycles, each including performing heat denaturation at 98° C. for 10 seconds, performing annealing at 58° C. for 15 seconds, and performing DNA extension reaction at 72° C. for 40 seconds. *Escherichia coli* DH5α was transformed with the PCR product thus amplified, to obtain plasmid vector pGAPP-btrC (W293R/N14T)-cscA-glf (FIG. 16) containing a mutant DOI synthase gene (btrC (W293R/N14T)).

Figure 17:
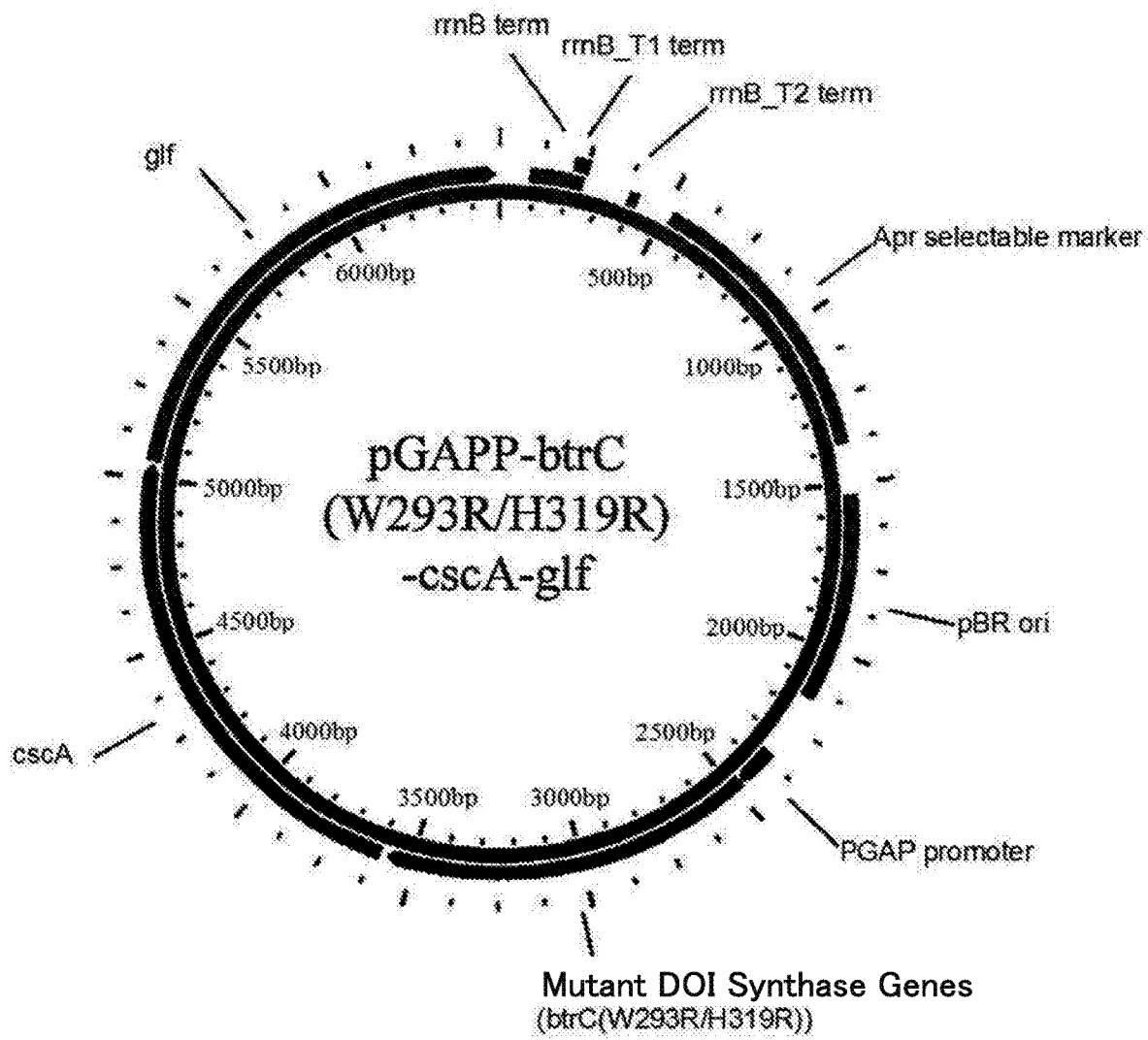
FIG. 17 illustrates the structure of pGAPP-btrC (W293R/H319R)-cscA-glf.

PCR amplification was performed using plasmid vector pGAPP-btrC (W293R)-cscA-glf containing a mutant DOI synthase gene (btrC (W293R)) as a template, and using primer vector 24 of SEQ ID NO: 25 (5'-ttaatccgcgataacaagagggggctac-3') and primer 25 of SEQ ID NO: 26 (5'-ttatcgcggattaaataatggaagat-3'). For the PCR amplification, PRIMESTAR Max DNA Polymerase (TAKARA) was used. The reaction conditions for PCR included 30 cycles, each including performing heat denaturation at 98° C. for 10 seconds, performing annealing at 54.4° C. for 15 seconds, and performing DNA extension reaction at 72° C. for 40 seconds. *Escherichia coli* DH5α was transformed with the PCR product thus amplified, to obtain plasmid vector pGAPP-btrC (W293R/H319R)-cscA-glf (FIG. 17) containing a mutant DOI synthase gene (btrC (W293R/H319R)).

Plasmid pGAPP-btrC (W293R)-cscA-glf, plasmid pGAPP-btrC (W293R/N14T)-cscA-glf, and plasmid pGAPP-btrC (W293R/H319R)-cscA-glf were purified and isolated using MONARCH® Plasmid Miniprep kit (New England Biolabs). Competent cells of *Escherichia coli* MG1655ΔpgiΔzwf strain (described in WO 2010/053052), which highly accumulates glucose 6-phosphate (a substrate of DOI synthase), were transformed with the plasmids, and cultured on LB agar plates containing 100 μg/mL of ampicillin at 37° C. overnight, thereby obtaining three MG1655ΔpgiΔzwf strains containing plasmid pGAPP-btrC (W293R)-cscA-glf, plasmid GAPP-btrC (W293R/N14T)-cscA-glf, and plasmid pGAPP-btrC (W293R/H319R)-cscA-glf, respectively.

DOI production efficiency evaluation using ajar fermenter was performed on the MG1655ΔpgiΔzwf strains respectively containing the three plasmids pGAPP-btrC (W293R)-cscA-glf, pGAPP-btrC (W293R/N14T)-cscA-glf, and pGAPP-btrC (W293R/H319R)-cscA-glf. As pre-culture, 0.1 mL of 100 mg/mL ampicillin was added to 500 mL baffled Erlenmeyer flasks each containing 100 g of LB culture medium (1% high polypeptone N, 0.5% yeast extract, 0.5% NaCl, 0.01% $FeSO_4 \cdot 7H_2O$), and three MG1655ΔpgiΔzwf strains containing three plasmids pGAPP-btrC (W293R)-cscA-glf, pGAPP-btrC (W293R/N14T)-cscA-glf, and pGAPP-btrC (W293R/H319R)-cscA-glf, respectively, were individually inoculated, in an amount of 0.1 mL, into the baffled Erlenmeyer flasks, and cultured with agitation at 120 rpm and 28° C. overnight.

A 1-liter culture vessel (culture vessel BML-01KP3, manufactured by ABLE Corporation) containing 350 g of culture medium component 1 (0.2% $K_2HAPO_4$, 0.2% $KH_2PO_4$, 0.01% $FeSO_4 \cdot 7H_2O$, 0.03% adecanol) was sterilized, 15 g of culture medium component 2 (10% $(NH_4)_2SO_4$, 4.6% $NH_4Cl$, 4.6% $MgSO_4 \cdot 7H_2O$), 5 g of 50% Corn Steep Liquor, and 700 μL of 50% phytic acid were added thereto, and 10 g of the preculture liquid was inoculated thereto, to start cultivation. Simultaneously with the start of the cultivation, a reagent sugar solution (21% Glc, 21% Fru, 1% Xyl) was fed at a rate of 0.13 g/min for 30 hours. The reagent sugar solution was prepared by separately sterilizing a glucose solution, a fructose solution and a xylose solution using high-temperature steam, and mixing the solutions.

Figure 18A:
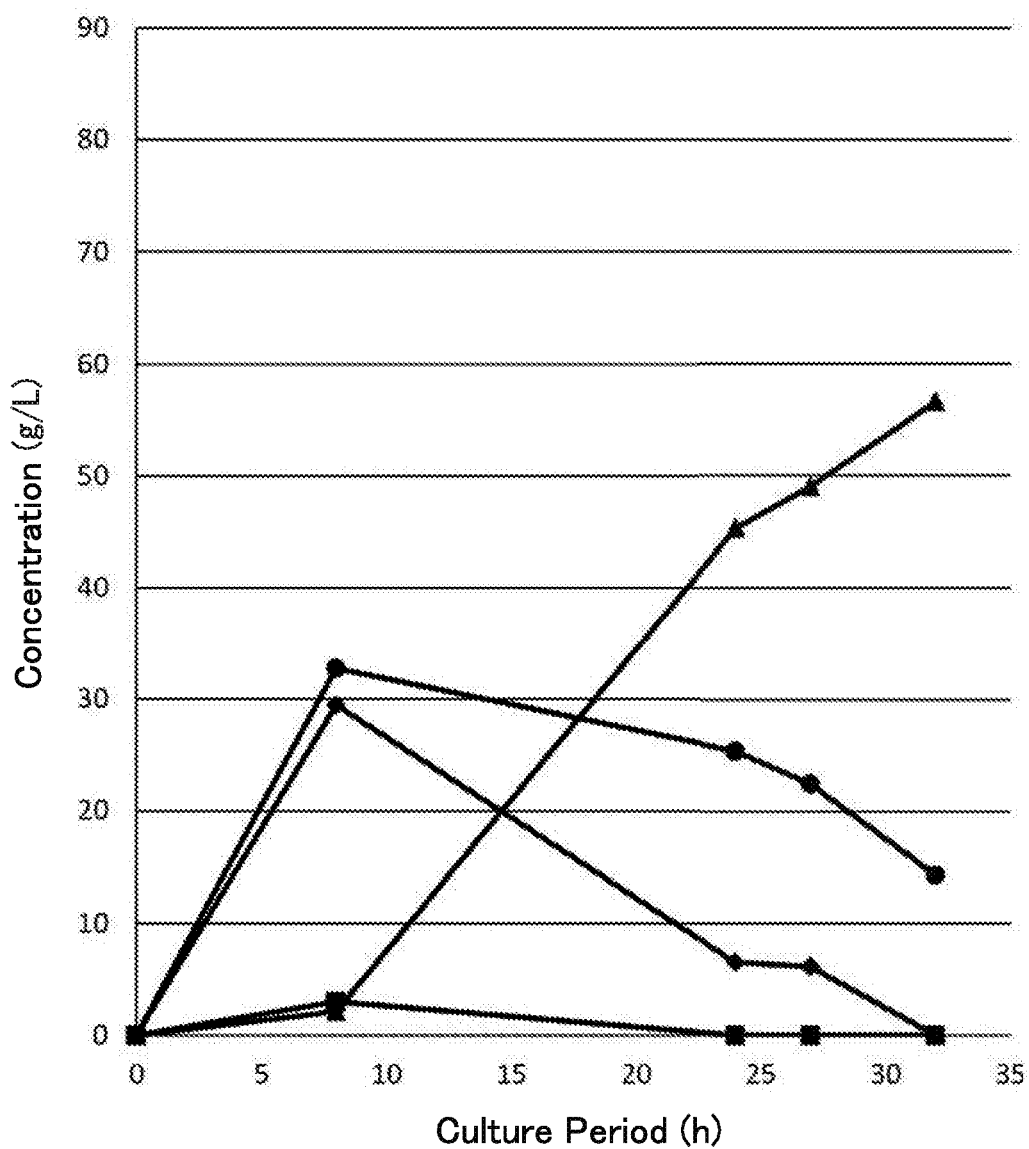
FIG. 18A shows time courses of DOI production amount (▲), glucose concentration (●), fructose concentration (♦), and xylose concentration (■) in the case of an *Escherichia coli* MG1655ΔpgiΔzwf strain that harbors pGAPP-btrC (W293R)-cscA-glf.
Figure 18B:
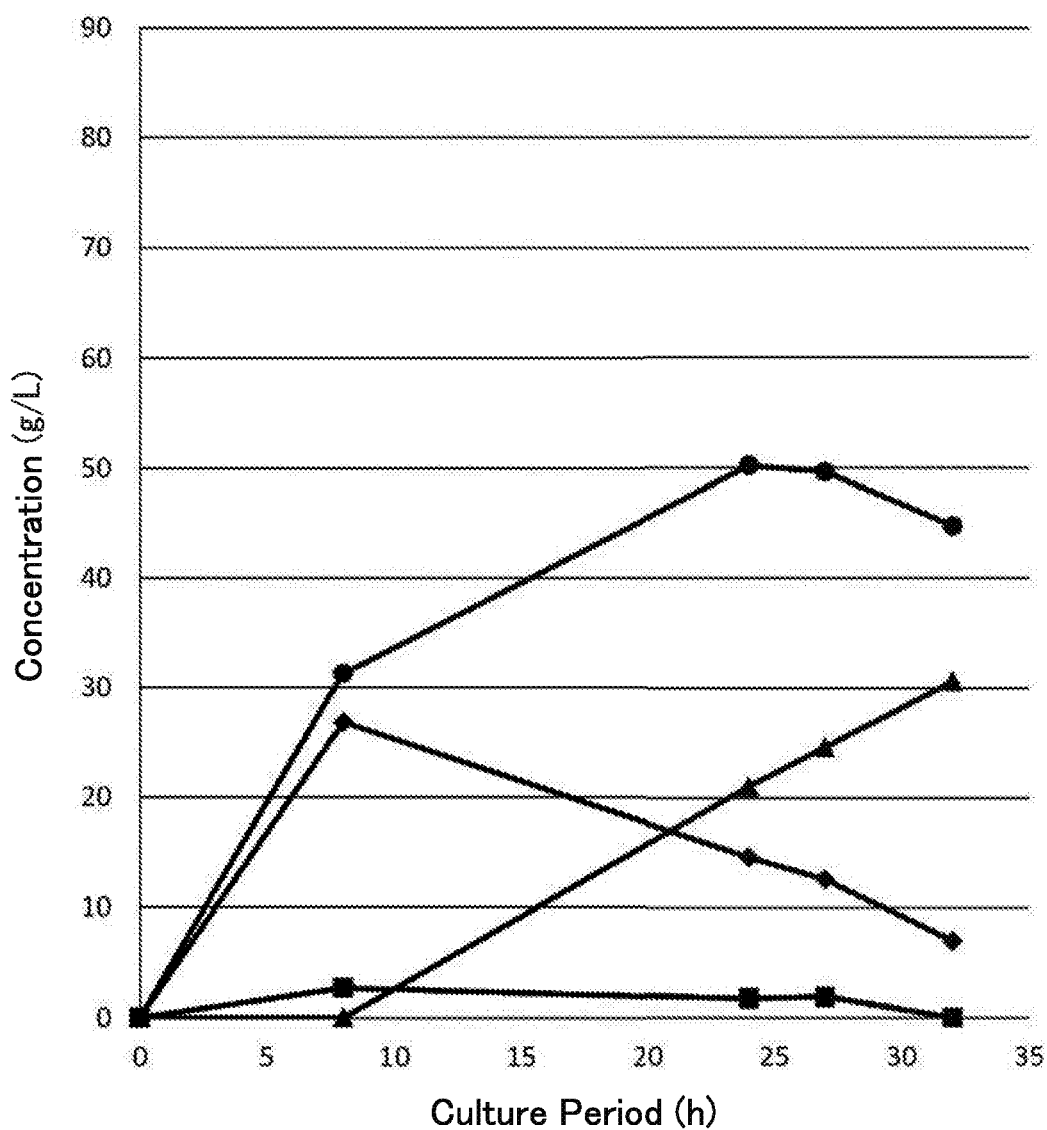
FIG. 18B shows time courses of DOI production amount (▲), glucose concentration (●), fructose concentration (♦), and xylose concentration (■) in the case of an *Escherichia coli* MG1655ΔpgiΔzwf strain that harbors pGAPP-btrC (W293R/N14T)-cscA-glf.
Figure 18C:
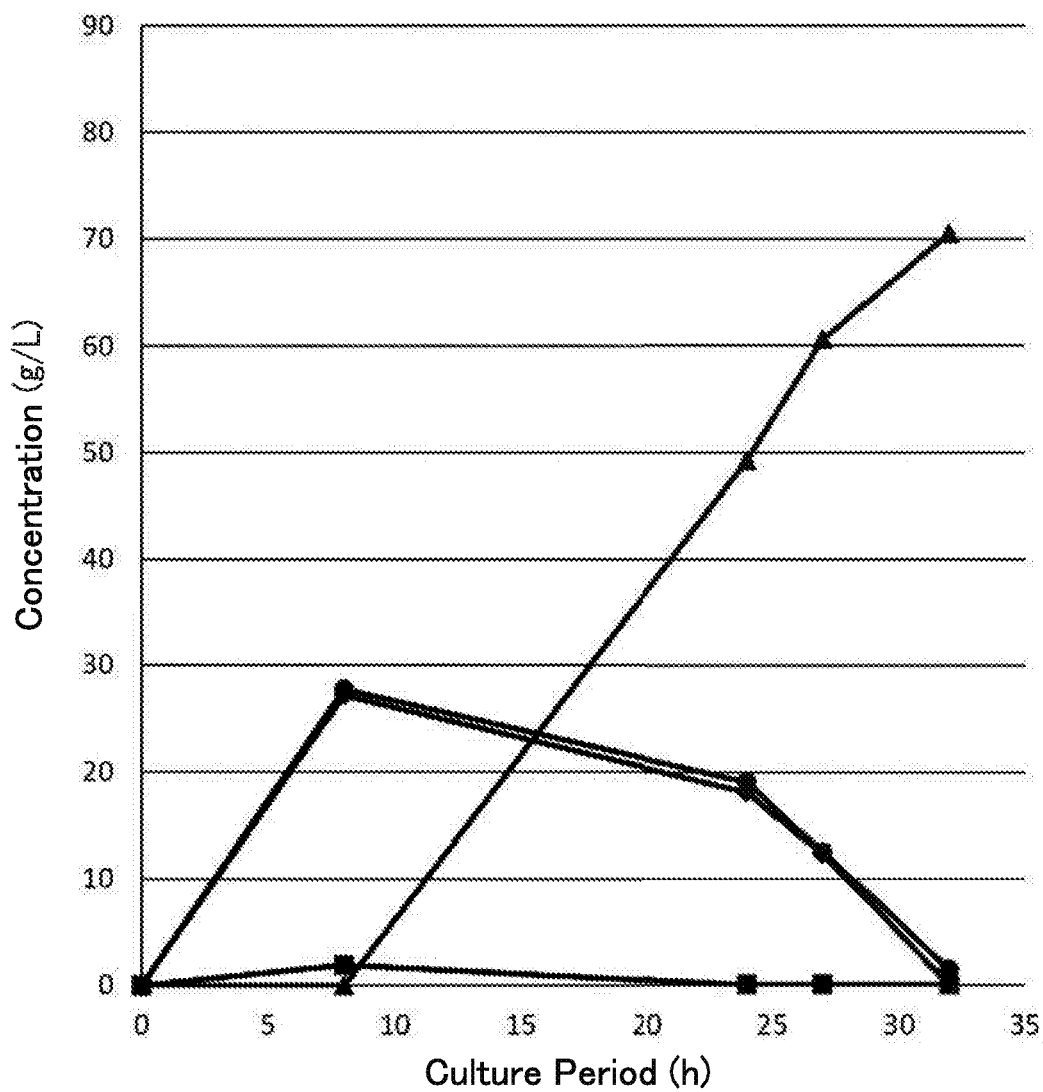
FIG. 18C shows time courses of DOI production amount (▲), glucose concentration (●), fructose concentration (♦), and xylose concentration (■) in the case of an *Escherichia coli* MG1655ΔpgiΔzwf strain that harbors pGAPP-btrC (W293R/H319R)-cscA-glf.

Cultivation was carried out at a culture temperature of 30° C., pH 6.0 (adjusted with 12.5% ammonia solution), an agitation rate of 800 rpm, and an aeration rate of 0.5 L/min for 32 hours under atmospheric pressure. Culture liquids obtained at 0, 8, 24, 27, and 32 hours after the start of culture were centrifuged, and the supernatants from which the bacterial cells have been removed were diluted 100-fold with sterile distilled water, and filtered (MILLEX-GV, 0.22 m, PVDF, 4 mm). Measurement of the concentrations of DOI, glucose, fructose, and xylose was performed using HPLC following the conditions indicated in Table 7. FIG. 18A shows the time courses of DOI production amount (▲), glucose concentration (●), fructose concentration (♦), and xylose concentration (■) in the case of the MG1655ΔpgiΔzwf strain containing pGAPP-btrC (W293R)-cscA-glf. FIG. 18B shows the time courses of DOI production amount (▲), glucose concentration (●), fructose concentration (♦), and xylose concentration (■) in the case of the MG1655ΔpgiΔzwf strain containing pGAPP-btrC (W293R/N14T)-cscA-glf. FIG. 18C shows the time courses of DOI production amount (▲), glucose concentration (●), fructose concentration (♦), and xylose concentration (■) in the case of the MG1655ΔpgiΔzwf strain containing pGAPP-btrC (W293R/H319R)-cscA-glf.

Table 6 shows DOI concentration at 32 hours observed for the MG1655ΔpgiΔzwf strains containing the three plasmids of pGAPP-btrC (W293R)-cscA-glf, pGAPP-btrC (W293R/N14T)-cscA-glf, and pGAPP-btrC (W293R/H319R)-cscA-glf, respectively. That is, Table 6 shows the DOI concentrations observed after 32 hours of cultivation of the *Escherichia coli* MG1655ΔpgiΔzwf strain containing pGAPP-btrC (W293R)-cscA-glf, the *Escherichia coli* MG1655ΔpgiΔzwf strain containing pGAPP-btrC (W293R/N14T)-cscA-glf, and the *Escherichia coli* MG1655ΔpgiΔzwf strain containing pGAPP-btrC (W293R/H319R)-cscA-glf.

TABLE 6

| | DOI Concentration (g/L) |
|---|---|
| MG1655ΔpgiΔzwf strain containing pGAPP-btrC (W293R)-cscA-glf | 56.6 |
| MG1655ΔpgiΔzwf strain containing pGAPP-btrC (W293R/N14T)-cscA-glf | 30.6 |
| MG1655ΔpgiΔzwf strain containing pGAPP-btrC (W293R/H319R)-cscA-glf | 70.5 |

The DOI concentration at 32 hours was 56.6 g/L in the case of the MG1655ΔpgiΔzwf strain containing pGAPP-btrC (W293R)-cscA-glf, 30.6 g/L in the case of the MG1655ΔpgiΔzwf strain containing pGAPP-btrC (W293R/N14T)-cscA-glf, and 70.5 g/L in the MG1655ΔpgiΔzwf strain containing pGAPP-btrC (W293R/H319R)-cscA-glf. Thus, the MG1655ΔpgiΔzwf strain containing pGAPP-btrC (W293R/H319R)-cscA-glf showed about 1.2 times higher DOI production efficiency than that of the MG1655ΔpgiΔzwf strain containing pGAPP-btrC (W293R)-cscA-glf.

TABLE 7

| HPLC Analysis Conditions in Measurement of DOI Amount | |
|---|---|
| Column | AMINEX HPX-87P Column |
| Eluent | Ultrapure Water |
| Flow Rate | 0.6 mL/min |
| Column Temperature | 50° C. |
| Detection | UV200 nm, RI |
| Charge Amount | 10 μL |

The disclosure of Japanese Patent Application No. 2017-061572, filed Mar. 27, 2017, is incorporated herein by reference in its entirety. All publications, patent applications, and technical standards mentioned in this specification are herein incorporated by reference to the same extent as if each individual publication, patent application, or technical standard was specifically and individually indicated to be incorporated by reference.

The invention claimed is:

1. A polypeptide having 2-deoxy-scyllo-inosose (DOI) synthesis activity, wherein the polypeptide comprises an amino acid sequence that has at least 95% sequence identity to the amino acid sequence of SEQ ID NO: 1, and has an amino acid substitution selected from the group consisting of:

(a) the asparagine corresponding to position 14 of SEQ ID NO: 1 is substituted with threonine;

(b) the tyrosine corresponding to position 37 of SEQ ID NO: 1 is substituted with phenylalanine;

(c) the alanine corresponding to position 290 of SEQ ID NO: 1 is substituted with threonine;

(d) the histidine corresponding to position 319 of SEQ ID NO: 1 is substituted with arginine; and (e) a combination of any of the substitutions (a), (b), (c), and (d), wherein the polypeptide has a higher DOI synthesis activity than a wild-type DOI synthase having the amino acid sequence of SEQ ID NO: 1.

2. The polypeptide according to claim 1, wherein the polypeptide has the amino acid substitution (d), and optionally further has the substitution (a), the substitution (b), the substitution (c), or a combination of any of the substitutions (a), (b), and (c).

3. The polypeptide according to claim 1, wherein the polypeptide has an additional amino acid substitution, wherein the tryptophan corresponding to position 293 of SEQ ID NO: 1 is substituted with arginine.

4. A polynucleotide comprising a nucleotide sequence encoding the polypeptide according to claim 1.

5. An expression cassette comprising the polynucleotide according to claim 4, a promoter, and a terminator, wherein the promoter and the terminator are linked to the polynucleotide, and wherein the promoter is upstream of the polynucleotide, and the terminator is downstream of the polynucleotide.

6. A vector comprising the expression cassette according to claim 5.

7. An isolated transformant that is transformed with the vector according to claim 6.

8. A method of producing a polypeptide having DOI synthesis activity, the method comprising culturing the transformant according to claim 7 under suitable conditions for production of the polypeptide.

9. A method of producing DOI, the method comprising contacting the polypeptide according to claim 1 with glucose or glucose 6-phosphate, thereby converting the glucose or glucose 6-phosphate into DOI.

10. A method of producing DOI, the method comprising contacting glucose or glucose 6-phosphate with the transformant according to claim 7, a culture product of the transformant, wherein the culture product comprises the polypeptide, or a processed product of the transformant or the culture product, wherein the processed product comprises the polypeptide, thereby converting the glucose or glucose 6-phosphate into DOI.

11. A polypeptide having DOI synthesis activity, wherein the polypeptide comprises an amino acid sequence that has at least 80% sequence identity to the amino acid sequence of SEQ ID NO: 1, and has an amino acid substitution selected from the group consisting of:
  (a) the asparagine corresponding to position 14 of SEQ ID NO: 1 is substituted with threonine;
  (b) the tyrosine corresponding to position 37 of SEQ ID NO: 1 is substituted with phenylalanine;
  (c) the histidine corresponding to position 319 of SEQ ID NO: 1 is substituted with arginine; and
  (d) a combination of any of the substitutions (a), (b), and (c),
  wherein the polypeptide has a higher DOI synthesis activity than a wild-type DOI synthase having the amino acid sequence of SEQ ID NO: 1.

12. The polypeptide according to claim 11, wherein the polypeptide has the amino acid substitution (c) and optionally further has the substitution (a) or the substitution (b), or a combination of the substitutions (a) and (b).

13. The polypeptide according to claim 11, wherein the polypeptide has an additional amino acid substitution, wherein the tryptophan corresponding to position 293 of SEQ ID NO: 1 is substituted with arginine.

* * * * *

SEQUENCE LISTING

<160> NUMBER OF SEQ ID NOS: 26

<210> SEQ ID NO 1
<211> LENGTH: 368
<212> TYPE: PRT
<213> ORGANISM: Bacillus circulans SANK72073

<400> SEQUENCE: 1

Met Thr Thr Lys Gln Ile Cys Phe Ala Asp Arg Cys Phe Asn Phe Ala
1               5                   10                  15

Phe Gly Glu His Val Leu Glu Ser Val Glu Ser Tyr Ile Pro Arg Asp
            20                  25                  30

Glu Phe Asp Gln Tyr Ile Met Ile Ser Asp Ser Gly Val Pro Asp Ser
        35                  40                  45

Ile Val His Tyr Ala Ala Glu Tyr Phe Gly Lys Leu Ala Pro Val His
    50                  55                  60

Ile Leu Arg Phe Gln Gly Gly Glu Glu Tyr Lys Thr Leu Ser Thr Val
65                  70                  75                  80

Thr Asn Leu Gln Glu Arg Ala Ile Ala Leu Gly Ala Asn Arg Arg Thr
                85                  90                  95

Ala Ile Val Ala Val Gly Gly Leu Thr Gly Asn Val Ala Gly Val
            100                 105                 110

Ala Ala Gly Met Met Phe Arg Gly Ile Ala Leu Ile His Val Pro Thr
            115                 120                 125

Thr Phe Leu Ala Ala Ser Asp Ser Val Leu Ser Ile Lys Gln Ala Val
        130                 135                 140

Asn Leu Thr Ser Gly Lys Asn Leu Val Gly Phe Tyr Tyr Pro Pro Arg
145                 150                 155                 160

Phe Val Phe Ala Asp Thr Arg Ile Leu Ser Glu Ser Pro Pro Arg Gln
                165                 170                 175

Val Lys Ala Gly Met Cys Glu Leu Val Lys Asn Met Leu Ile Leu Glu
            180                 185                 190

Asn Asp Asn Lys Glu Phe Thr Glu Asp Asp Leu Asn Ser Ala Asn Val
        195                 200                 205

Tyr Ser Pro Lys Gln Leu Glu Thr Phe Ile Asn Phe Cys Ile Ser Ala
    210                 215                 220

Lys Met Ser Val Leu Ser Glu Asp Ile Tyr Glu Lys Lys Lys Gly Leu
225                 230                 235                 240

Ile Phe Glu Tyr Gly His Thr Ile Gly His Ala Ile Glu Leu Ala Glu
                245                 250                 255

Gln Gly Gly Ile Thr His Gly Glu Ala Ile Ala Val Gly Met Ile Tyr
            260                 265                 270

Ala Ala Lys Ile Ala Asn Arg Met Asn Leu Met Pro Glu His Asp Val
        275                 280                 285

Ser Ala His Tyr Trp Leu Leu Asn Lys Ile Gly Ala Leu Gln Asp Ile
    290                 295                 300

Pro Leu Lys Ser Asp Pro Asp Ser Ile Phe His Tyr Leu Ile His Asp
305                 310                 315                 320

Asn Lys Arg Gly Tyr Ile Lys Leu Asp Glu Asp Asn Leu Gly Met Ile
                325                 330                 335

Leu Leu Ser Gly Val Gly Lys Pro Ala Met Tyr Asn Gln Thr Leu Leu
            340                 345                 350

Thr Pro Val Arg Lys Thr Leu Ile Lys Glu Val Ile Arg Glu Gly Leu
        355                 360                 365

```
<210> SEQ ID NO 2
<211> LENGTH: 30
<212> TYPE: DNA
<213> ORGANISM: Artificial
<220> FEATURE:
<223> OTHER INFORMATION: Primer

<400> SEQUENCE: 2
acgcgtcgac atgacgacta aacaaatttg                                      30

<210> SEQ ID NO 3
<211> LENGTH: 27
<212> TYPE: DNA
<213> ORGANISM: Artificial
<220> FEATURE:
<223> OTHER INFORMATION: Primer

<400> SEQUENCE: 3
aaaactgcag ttacagccct tcccgga                                         27

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
atggtaccga gctcggatcc                                                 20

<210> SEQ ID NO 5
<211> LENGTH: 34
<212> TYPE: DNA
<213> ORGANISM: Artificial
<220> FEATURE:
<223> OTHER INFORMATION: Primer

<400> SEQUENCE: 5
ctagtctaga ctaggagata atttatcacc gcag                                 34

<210> SEQ ID NO 6
<211> LENGTH: 24
<212> TYPE: DNA
<213> ORGANISM: Artificial
<220> FEATURE:
<223> OTHER INFORMATION: Primer

<400> SEQUENCE: 6
ctagtctaga gtcgtttttc tgct                                            24

<210> SEQ ID NO 7
<211> LENGTH: 38
<212> TYPE: DNA
<213> ORGANISM: Artificial
<220> FEATURE:
<223> OTHER INFORMATION: Primer

<400> SEQUENCE: 7
acgcgtcgac ttcgaactcc ttaaatttat ttgaaggc                             38

<210> SEQ ID NO 8
<211> LENGTH: 18
<212> TYPE: DNA
<213> ORGANISM: Artificial
<220> FEATURE:
<223> OTHER INFORMATION: Primer
```

```
<400> SEQUENCE: 8
ggagccaacc gaagaacc                                                    18

<210> SEQ ID NO 9
<211> LENGTH: 24
<212> TYPE: DNA
<213> ORGANISM: Artificial
<220> FEATURE:
<223> OTHER INFORMATION: Primer

<400> SEQUENCE: 9
ctagtctaga gtcgtttttc tgct                                             24

<210> SEQ ID NO 10
<211> LENGTH: 18
<212> TYPE: DNA
<213> ORGANISM: Artificial
<220> FEATURE:
<223> OTHER INFORMATION: Primer

<400> SEQUENCE: 10
acctgatgcc cgaacatg                                                    18

<210> SEQ ID NO 11
<211> LENGTH: 18
<212> TYPE: DNA
<213> ORGANISM: Artificial
<220> FEATURE:
<223> OTHER INFORMATION: Primer

<400> SEQUENCE: 11
agatcgaatc cgggtccg                                                    18

<210> SEQ ID NO 12
<211> LENGTH: 28
<212> TYPE: DNA
<213> ORGANISM: Artificial
<220> FEATURE:
<223> OTHER INFORMATION: Primer

<400> SEQUENCE: 12
cgcggatcca tgacgactaa acaaattt                                         28

<210> SEQ ID NO 13
<211> LENGTH: 28
<212> TYPE: DNA
<213> ORGANISM: Artificial
<220> FEATURE:
<223> OTHER INFORMATION: Primer

<400> SEQUENCE: 13
cccaagcttt tacagcccctt ccccgatc                                        28

<210> SEQ ID NO 14
<211> LENGTH: 29
<212> TYPE: DNA
<213> ORGANISM: Artificial
<220> FEATURE:
<223> OTHER INFORMATION: Primer

<400> SEQUENCE: 14
cgcggatccg agataattta tcaccgcag                                        29
```

```
<210> SEQ ID NO 15
<211> LENGTH: 30
<212> TYPE: DNA
<213> ORGANISM: Artificial
<220> FEATURE:
<223> OTHER INFORMATION: Primer

<400> SEQUENCE: 15
cgcggatccg cgggaagagt gaggcgagtc                                       30

<210> SEQ ID NO 16
<211> LENGTH: 19
<212> TYPE: DNA
<213> ORGANISM: Artificial
<220> FEATURE:
<223> OTHER INFORMATION: Primer

<400> SEQUENCE: 16
atattccacc acctatttg                                                   19

<210> SEQ ID NO 17
<211> LENGTH: 28
<212> TYPE: DNA
<213> ORGANISM: Artificial
<220> FEATURE:
<223> OTHER INFORMATION: Primer

<400> SEQUENCE: 17
atgacgacta aacaaatttg ttttgcgg                                         28

<210> SEQ ID NO 18
<211> LENGTH: 29
<212> TYPE: DNA
<213> ORGANISM: Artificial
<220> FEATURE:
<223> OTHER INFORMATION: Primer

<400> SEQUENCE: 18
aaaactgcag ttacagccct tcccggatc                                        29

<210> SEQ ID NO 19
<211> LENGTH: 30
<212> TYPE: DNA
<213> ORGANISM: Artificial
<220> FEATURE:
<223> OTHER INFORMATION: Primer

<400> SEQUENCE: 19
ttccattatt aatccgcga taacaagagg                                        30

<210> SEQ ID NO 20
<211> LENGTH: 30
<212> TYPE: DNA
<213> ORGANISM: Artificial
<220> FEATURE:
<223> OTHER INFORMATION: Primer

<400> SEQUENCE: 20
cctcttgtta tcgcggatta ataatggaa                                        30

<210> SEQ ID NO 21
<211> LENGTH: 27
<212> TYPE: DNA
<213> ORGANISM: Artificial
<220> FEATURE:
<223> OTHER INFORMATION: Primer
```

```
<400> SEQUENCE: 21
cattacaggc ttttaaataa aatcggg                                      27

<210> SEQ ID NO 22
<211> LENGTH: 27
<212> TYPE: DNA
<213> ORGANISM: Artificial
<220> FEATURE:
<223> OTHER INFORMATION: Primer

<400> SEQUENCE: 22
taaaagcctg taatgggcgg acacgtc                                      27

<210> SEQ ID NO 23
<211> LENGTH: 27
<212> TYPE: DNA
<213> ORGANISM: Artificial
<220> FEATURE:
<223> OTHER INFORMATION: Primer

<400> SEQUENCE: 23
tgttttacct ttgcattcgg cgaacat                                      27

<210> SEQ ID NO 24
<211> LENGTH: 27
<212> TYPE: DNA
<213> ORGANISM: Artificial
<220> FEATURE:
<223> OTHER INFORMATION: Primer

<400> SEQUENCE: 24
tgcaaaggta aaacaccggt ccgcaaa                                      27

<210> SEQ ID NO 25
<211> LENGTH: 27
<212> TYPE: DNA
<213> ORGANISM: Artificial
<220> FEATURE:
<223> OTHER INFORMATION: Primer

<400> SEQUENCE: 25
ttaatccgcg ataacaagag gggctac                                      27

<210> SEQ ID NO 26
<211> LENGTH: 26
<212> TYPE: DNA
<213> ORGANISM: Artificial
<220> FEATURE:
<223> OTHER INFORMATION: Primer

<400> SEQUENCE: 26
ttatcgcgga ttaaataatg gaagat                                       26
```